United States Patent
Su et al.

(10) Patent No.: US 12,188,029 B2
(45) Date of Patent: Jan. 7, 2025

(54) METHOD FOR THE TRANSIENT EXPRESSION OF NUCLEIC ACIDS IN PLANTS

(71) Applicant: SYNGENTA CROP PROTECTION AG, Basel (CH)

(72) Inventors: Pei Su, Research Triangle Park, NC (US); Kasimalai Azhakanandamn, Research Triangle Park, NC (US); Michele Yarnall, Research Triangle Park, NC (US); Rachel Whinna, Research Triangle Park, NC (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/557,847

(22) Filed: Dec. 21, 2021

(65) Prior Publication Data

US 2022/0195444 A1 Jun. 23, 2022

Related U.S. Application Data

(60) Provisional application No. 63/128,917, filed on Dec. 22, 2020.

(51) Int. Cl.
*C12N 15/82* (2006.01)
(52) U.S. Cl.
CPC ................ *C12N 15/8205* (2013.01)
(58) Field of Classification Search
CPC .................................................. C12N 15/8205
See application file for complete search history.

(56) References Cited

U.S. PATENT DOCUMENTS

| | | | | |
|---|---|---|---|---|
| 5,457,041 A | * | 10/1995 | Ginaven | A61M 37/0015 435/285.1 |
| 2012/0174262 A1 | * | 7/2012 | Azhakanandam | C12N 15/8216 800/278 |
| 2012/0185969 A1 | | 7/2012 | Debrecht et al. | |

FOREIGN PATENT DOCUMENTS

WO 2019/027789 A1 2/2019

OTHER PUBLICATIONS

Andrieu et al. Rice, 2012, 5:23.*
International Search Report for International Application No. PCT/US21/64343 mailed May 5, 2022.
AC215994 GenBank Accession No. AC215994, *Zea mays* cultivar B73 chromosome 2 clone CI 1201 158D20, Sep. 13, 2014 [online]. [Retrieved on Apr. 1, 2022]. Retrieved from the Internet <URL: https://www.ncbi.nlm.nih.gov/nuccore/AC215994> Entire document.
AF544126 GenBank Accession No. AF544126, *Zea mays* subsp. mays cultivar W153R endosperm-specific sucrose synthase (shrunken1) gene, partial sequence, [online], [Retrieved on Apr. 1, 2022]. Retrieved from the Internet <URL: https://www.ncbi.nlm.nih.gov/nuccore/AF544126> Entire document.

* cited by examiner

*Primary Examiner* — David H Kruse
(74) *Attorney, Agent, or Firm* — Dale Skalla

(57) ABSTRACT

Compositions and methods for transiently expressing proteins in a plant are provided. The compositions comprise plants, seeds, plant tissues, and plant parts expressing a protein, wherein the protein is expressed transiently and the transient expression of the protein can be used as a predictive model of how said protein will be expressed in stable transgenic plants in regards to qualitative and quantitative data. The predictive model may be used but is not limited to: promoter evaluation, evaluation of expression cassette construction for best performance (e.g. addition of enhancers or gene silencing suppressors), evaluation of best ways to express heterologous genes.

10 Claims, 3 Drawing Sheets

Specification includes a Sequence Listing.

SEQUENCE LISTING

```
<160> NUMBER OF SEQ ID NOS: 104

<210> SEQ ID NO 1
<211> LENGTH: 1181
<212> TYPE: DNA
<213> ORGANISM: Zea mays

<400> SEQUENCE: 1
cggtgaggga ttgacgcata acagaaataa ctagtacctt tctataaggc aaaattgagc     60
acagtgattc actgattgtg tccectaget tctctttccc cacctacagg ttgcaacgca    120
aaagcaagca ggaaaaaaag aaacacattt agcagtctag actctaacat catccaacga    180
ttcatggcct gttggcatgt tgctggaccg tcactggttc acaggccttt agaggatact    240
tggccagagc gggcgcgcgt gcgcggcggc ggagtgctgt ggtatccagt gcgtgtgcgc    300
cgatgtggag gccaacgcag cgggcctggg ctttgaggcc gggatgggga gcctcaggga    360
gtgcggcgac ggctgcgcat ctgcgccgtc atgtgggaac cgacggactc agcgcggcgt    420
cgctgtgcgg ctgtgcgtct tgcgccacct gcacaaggtg gtttgtgtgc gagtacgccg    480
gtaaagcagg gcatatgcct ctctctctgg attctttgcg cttgcatact aattgttggt    540
ttgcattttg agctgaacca atctattaaa atcgctggac gactattaaa atcgctggac    600
gacgtagttc tgtacttctg ttccatgacg gacgaaatga ttccggatga agctgtgcgc    660
ccgtgctgca ttccaaactg caaaaattgc tgattgctgg acgcggctcc gtccgacggc    720
gtacaaactg attctatatg gaccgatgag gcgatccaaa cagactacta aactcctact    780
taccaagcaa acaattgat caatgattac ccgagtgcca aacgggcact atgaacacag    840
aacccataac ataataagct aaactgtact aatgcacaag atgcattaaa aaatgccgtt    900
ttagtagatt gttaaccatg tttgtgctct ccacatgtca tagatatatt cttataattt    960
gttcacctgt gtttccggtt agttgttcat ctatgcctag ctttgctttg gttctgttct   1020
tgtcatagct gaaaaagaa gcgaattcat tgggcaaagc cttatatata gttgatacat   1080
aaggattcat gtaaaataca tttgcagtcc ggtacagttt ttacttttta gccttgtgcc   1140
ctttgcaaaa aggactacaa gaatcatgcc tttttcagc g                        1181

<210> SEQ ID NO 2
<211> LENGTH: 1499
<212> TYPE: DNA
<213> ORGANISM: Zea mays

<400> SEQUENCE: 2
ttggtttgga tatttgaaaa ttggaaatta gaaattcaaa tagaaaagga atttagaaaa     60
gaaatggggg gaaattcgtg tatttgggtc gtaattgtcc agacagccca aatccaccgc    120
gctgccctgg gtgtgggtct ctgaccggtg gctcccgctc ctgctcactg gcctcccctt    180
cccgcgtgtg gttgttgcgc tcactggcac gcgggcctac tgctcagtct ccagtcgcgc    240
```

```
tcaggaatct attctcacgg acgcgtgggc aatgtggcc aaccagaaca cttccccatc    300
gctcgcgtgg cccatcccct tacgctttcg cgcctgctga catcgcggcc caatcaccag    360
cctcctcacc ctcacatgcg ctggagaacc ctggtcgcag ttaaatggga ccacactctc    420
aggtcgcctt ccccaactcg ccgcagatct tgcacggtaa caccatgctt gaccgatgtc    480
tacctgcccc gcttgcttcg atcgtggctg ttacgccctc gcctctgggc tataagaccc    540
caagcctcgc gccgctcacc tcccaaacac catggccgtg atctcgctc tccggtgaac    600 ggcgcccacc cttcgtcctc ctccctctgg ccctgtgact agcggacggg ccattggttc    660
tcgctaaggt cgttggtgtc ggcgtcctcg cgattgatgc tctccagcag cgcacccgag    720
tcctgtcgcc gctgcccttg cttggcctcg tcgcatcctc gacccaggcg cgcccaccgt    780
cgagctttgg ggagggaatc tgtgcgcata cgccggtgta cgcctgcgcc ggttcccaac    840
ccttggaaga ccacctgtga tgctccattg cggtgctcgg atggtgctcg cggcatcgca    900
ctgagtcgtc cgtgtcttgg gagcacgtga tttctcgcta tggttaagtc gccgcctcgg    960
tgccgctctt ctccctgggc cgcgtcgcac atgatctagt ttctggtaag ttgttacccg   1020
ctccattcgc cttgcactga gcaacgtgta gcatctgttt gaactagaaa tagggcgccg   1080
gagcatgtag aagggggtcc gtccatgggc gccgccgtgc cctgttgggc ggggtgggag   1140
aagcgttggt ggccgttgat cccagaccga ctgtggcaat catatctcgc atacccttt    1200 gcttggatga gtattgaccg ttcgatctag atgtgcgtac gagattagaa accgcgtac    1260 cgcttttag ataaaatccg agccgtagat tgtagatctg agggctaggt cgagtcgtag   1320
acatggaact ccctcgacca tcaatctcgt atccaaggca cccgagagcg taccgataca   1380
ttaagttgta tggtttaatc tgggccgtag gattagatat gagtggtcgt ggttggcaga   1440 tacccccttcg ccgagcctta tttgcaaaag acaccccgta gaatttaata acaaacccg   1499
```

<210> SEQ ID NO 3
<211> LENGTH: 915
<212> TYPE: DNA
<213> ORGANISM: Zea mays

<400> SEQUENCE: 3

```
gttcaaagct tgcgtgcaga tactcccgta aaacacgcat ccgctcgtgt gcagttcaat     60
cacaagtttg tggatggttg gaacgcagtc acccgtcacc ccacggcccc acgtggccgt    120
gacacggtcg gttcaaagtc cacggtgtac cacttccacc cgtccccacc ccaccatcct    180
tctctacttc tctcctctct ctcccaacgg acccgatctc gtacctcact tccgtcccgc    240
ccagcttcgc ttcacggcgc gccgaccggc ttggacgcgc cgaccggctc gtgatcagct    300
cggtcggatc cgacggtcgc tcgctgctgc agcgggcgct tgctgtgcgt cgcgtgggct    360
cggccggagc ccggagggag gcggagcctt ccccgggtct cgaagatggc ggcgccgccg    420
gcgagggccc gggccgacta cgactacctc atcaagctgc tcctcatcgg cgatagcggt    480
gagtgccttc accatcacgc ctcctccccc tctcgctctc cgtccggatc gattggctgc    540
ggtgagatct gagtgcgaaa tcgaagttcg gttctgattc gtccggatcg actgtgaaac    600
gcggatgctc ctgggccctg ctcctcccaa aagctgccgc tgtttgcctg tttcgtcgat    660
gacgtgcaac ggttttatgt atataggaat gatatgctga aaactcaccc accatcgggt    720
gatgactact ttgctagttg atgcttgaga gctacattta caaccacaca gacaagtgaa    780
ccgaaattcc atttggaaac cgggatgcga caacggacgc taattacaaa ataaacagcc    840
```

```
tttgccgtct tatctaactg ttacattgga atggtgattg tcggtgctca cagaaaagga    900
aatgcatgga ttttg                                                     915

<210> SEQ ID NO 4
<211> LENGTH: 1145
<212> TYPE: DNA
<213> ORGANISM: Zea mays

<400> SEQUENCE: 4
gggcgtagca gtgagcggga cacggagcgg cggcggcggc gccatcgagc gcgagcagga     60
acaggcaaac aggagctagc gcgagtgcgt gacctaggga cctagcgcga cccagtgggc    120
agcagcgtct tgacgtattc gtattcgata tccgaagcaa gtatccgaat ccatatccga    180
tatccagaaa aaacgttcga atatccgaaa aaaatatcca aatcattatt tgctctcttt    240
ggatacggat acgacgggt ttacatccct agctggtggg cacgcggacg cggtggggtg    300
gggtggggtg gggtggtggg gtgcgttgcg gtgcggctag acgggacgga gccttgccgt    360
taacttgaga cggcggtttg ataggatccg agccgacatg gtgcgtcgga tcgaaaccag    420
gaccgacctt ggtgtctcgt tttccaggtc gaaacggcta gcggttcctt ttaaaccgcc    480
gtcagcgtct ctcggcgtcg tggcgaagaa accgacgac tcgtcggtct ctgtgagctg    540
tgacgcaagc tactgatcac catcacctgc tggcgcgggg acggcggcga cccggcctgc    600
gacgggcaca cgcccacacg cggacgcgga gctgtttgct gcgcctgcgc ggcaggacac    660
cggcggtttg gatgctcctg ccacctgctc gccggtaggc gggcggcgca ccgcgcgcgt    720
gtcccaaagt cagccgcaaa atgaagagaa acacggagga cgcaacacgt cgtcgacgcg    780
aaggctgatc tcgctagcac ggagcacgcc catcatcatc cgcctcgatc tgctaacccg    840
cgccatggcc ccatttcgcc cgtccgtcca atgggatgga tcttttttttt tttttgaacg    900 gaccccggac ccggagggag tcgatcggaa cgaggtacag taacaggacc acatatgtgt    960
ggtctcgcag ttccgataag accagacacc ggcccatctc ggaccggacg tgctcctcta   1020
cgaactatgg gcggattccc gctttccgga ggaagtaaat ccctccgtta aaaaaaaact   1080
gtgcttgtat tcctttgatc acaggagtat ggacccgctt gtttcaactt tagctttttc   1140
aaccg                                                              1145

<210> SEQ ID NO 5
<211> LENGTH: 1163
<212> TYPE: DNA
<213> ORGANISM: Zea mays

<400> SEQUENCE: 5
ggtgcagcag aagcaacaag ccccaaagtg gatagcggcc aaagcaacca gcggaagctt     60
cttaattacg gctaggcttc ttaattaagt gcccatcaaa tcaagctgcc aacgcaggca    120
gccagccact ctcgagaagc gtatccgggg cccacaaggt ggaatcaacg ttcaccctgc    180
cgtgacgcct tgtccccagc taccccgccg tctgcctacc ccattcaccg cacctccatg    240
gcccacgcgt cagtggtcct gtgactgggt gggcaggtga gcgtgagtcc gtgagaagga    300 agcaagccc gttccgccgt tcgctcgtcc catccgataa ctttaccgtg tgtactgtga    360
ttgtcgctct gacccgcggc accgtgctg aagcctccca cgaccctcgt ggcacggtgg    420
gacatagcga caggcgcctc acgctcctcc ccctcccct ctcttccccc ctgccaggca    480
agagagaaga aacgcacgcg agccgcgagc agaatacagc agcacgggcg ccagcgccat    540
cctgatctcg ctatctccct tctcttctcc cccgatgcga tctcgccaaa ccctaatccc    600
```

```
gccgcccgcc gcgcggccgt cgccggagcc ctagcccga atgtggcggt gacgcccgtg      660
ctgctgtatt ctgctcgcac tggtcctgct cgtggagcac ggcatcggtg agcggggcca      720
gcgccgcggg cggtgcgcgc acggagaagt ccgccggagg ctgccgaggc agcgtcaatg      780
agggagatga gcgcgggctt ggccttgaac gccgcgacgc ggaggagctt gtagaggcac      840
gggaggagcc cccggaggta cacggcgagg tcgtcggtgg gctccgaggc ctcgacggcg      900
gcggcggcag cgagcgcggc ggccagctgc gcgcacttgt cctgctcgtg gagcacgacg      960
tcggtgagcg gggccagcgc cgcgggcggt gcgcgcacgg aggagggacg cagcgcagcg     1020
cggcggctag gagcctggtc acgagcggcg cgacggcatc ccgcgggtgc tccccagcga     1080
cgagcgccag cagccgaagc gagtgatgtc ggatgcggag gtggttggaa gcgcggcggg     1140
gtttgcggga ggacgtgcgg gca                                            1163

<210> SEQ ID NO 6
<211> LENGTH: 4230
<212> TYPE: DNA
<213> ORGANISM: Zea mays

<400> SEQUENCE: 6
tgtactgacg gtgtctgact aaatcaccaa aaaatcgttt ggcactcgtc gaattgctcc       60
tgctcatggt taggaggggg cagagtagct accgttgctc gctctggtta gctttcgctg      120
aggtggtcag cagtcagcac agtggagttc tctcaggcaa ttacgcccct gttgtacagt      180 tcctttttt ctctcttcgg ttccgtggaa gttgttagca aatttttctgc agtatgtttc      240 tcttcgacgc ttatacggtc cgctctgtaa aagctgggca gctgcactga aggtctgaag      300
cagcatacaa ccttgcggct ctcaaaacat gtttgctcca ttttacagct tctaacaaac      360
tacaattccc aacttacagc ttgcaactta ggagggaaga cggtttcact ggacaacaat      420
gagagaaagc aagagcaccg aatgggaatg tcacacacaa acgcacacgt gacgcacccc      480
ggcgacgatc aacatggatg accccaggcc cggcaacagc attaacgcgt cacattgcgc      540
cggccgaaag aaccgatgga tgattccttg cgttcgcagc aaaccttga cacggcggcg      600 agcgaccacc tcggcccggc ccggccccgt accaccacgt cggtgcctac acctgcgcct      660
gcgcctgcgc gtctgcactg tccgagacgg ggacgaatgg gcctggtcca gccggtggac      720
cacctgatca taaccaactc aaaaggcatg gtccctacgc accgtgtttt ttccccctc      780 cacccttttt tttcccacg gacgcgacgg gtgccgtgcc gtgccgcgac gccacgtacg      840
tccggtccac gccgaaccca gctcccgctg tctgttgctg gctggtgcga cgcgacgccg      900
aaatatcctg gcctggcccc gacccgacgc atcgcgtgcg tcgtgctcgc gcacaactca      960 cccccatcc cgcgccccat gcgcactgca gctgtggtgg ccggacgcga ggggcgcacg     1020
gcagggcacg agacgaccgc ccacgggggg aatctgttcc atgcatgcac cagtaggaga     1080
aacagaaact gttcgacgt ctctgcaagc aggagcgcga tgctgttgac gccgttggaa     1140
agacgacgcg cgcgacacgg caacacaaca gaacatactc ccgtagctag cgcacgtagt     1200
agtagtaggc cgctgcaaga ttcgatcttt catcgtgctg gttgcacgct atcgttgttc     1260
gctagtacgt attcctacta catacataat agctagccag cgtcgcctag ggcgatgcaa     1320 caccctagtag gtgcctaaaa gcgtaggcgc ggacgcgcgc gtcgagtcga ctcgactcgg     1380
accttccact tccaaccaac taaaactctg cgcggttgcg gtgcgccccc ggcgggcatc     1440
aaagagcctc cttccaaacc catgcccgag cccgacgacg acagccaccc gagactcaga     1500
```

```
agcacggcac atacgatcgt gacaagtgat ggagaggcag acacgaaatc tgcttgccga    1560
aaagcctact agcggtggca gataatggga aacctaacac cactctcgaa acatcagaa    1620 ggaaattaca acaaaaaaag gagctttcgc tcccgctcca gcgatacacg ccgtgatctc    1680
gaccagagcg ccccccttg ccccagtttg acaacagctg cctgctgctg ctagcaactc    1740
gtgccggcct gttcgtttcg caacagtgaa agcgtggatg gccggtgcaa atgcaatgca    1800
actcatcacc gatcgccaca aaaagtccag gcgcttttgg ctccctgctc ttagtgctct    1860
agtgccccct cctgcaaggc tgcaatttgc gattcgcgag cagtgaccgt gaccgtgacc    1920
gtgaccgtga aaacgcgcga gctccccggc caccgcactg cacggagcac acacacaact    1980
agcccgcgcc tttgccaaca gctcgaaacc cttgcgggct gccgcggcc gcgcgcgcgt    2040 tttcacctct gatctcgtgc gcggcgcggc cgggtcggac cggaacgaaa gggccaaagg    2100
ggtagcgacg ctacgtcgct actccgccgt acgtccgcgc caccgcctgc gcaggaagga    2160
aggaagggaa cccggccgtc cgtccggccg ggcactaggg tggtgcctgc ctgtggcgtt    2220
gccgcttcgg gttggctcgt gctccgtgct tgcaattcca gtgccgtact gccgtccatg    2280
gatggacgga cgtcggcaga aaaggcgaa gatggaccag agcggaaaag gagccgagct    2340
ccagcagcga gcagcgtcgt ccgtcccca caggccacgc caaaggcaac cctgctggct    2400
cgcatcgctt tcctagccgc cctaggcggg ggggtcgcct gtgtctttcg ggcaggtgct    2460
gtgccttggc ttgtcgcccc attccctcac cgccagcgcc cagcagccag cacctcgttt    2520
gggttttgga tgcagcactg cacgattccc tgacagctcg gaaagggtac agagcctgcg    2580
gttggggata gaacagtgg tgagccaaaa aggttgggta gctcgttcaa ccagcggaac    2640
cagtattttt tatattagtt catattgtta gttaacgagc ctatcaagtc aaagctgtcg    2700
agcttaaatt tatattaatc tcatattgta ctatgtctcg gttgattgtt agacctagtc    2760 ctataaaga acattatcat gacaatcaat ctattttctt taaactggta agaagataac    2820 tatgagccc tagatagact agtccgtcgt tattcctccc tccttcctcc gggacaggta    2880
gctcgcgtcg tgggggcagc gcaagcacgc ggtcccggtc tttgaatatg tccggggatt    2940
tcagcggacg catgtggcgt ccagtacgtg agcagggtac tatgtttcac tttcaaggga    3000
tgagcaactt tcagtttaac caagccttat taccgaagta gacagaagta aaacacaagt    3060
taccgaaggc tgtttccacc actcgaaaag actccgtggc acgcagagga ggacagaatt    3120
ctcaaatcag tacgcgctgc ctgctgccct gtgctgtgct tcatcggagc aagagcatgt    3180
gctgggctgg aatctcgtcc cgtaacgatt cggttcctcg tcatgttctg ggattttgt    3240 tcatcctttt attttattta ttttttacc gcgacgcgag atcacctttg gtcccccctc    3300 cccccggtcct ctcctcctgc tggctgccat ctgccaagcc aagggcgctg ccgctactgt    3360
gcctgaacgc tgccgcgcca cagcggcagc ctcgcagtga gatcccaggc acccattcaa    3420
ttctgcagtt ctcgctgccg ccttccctc tctgtcttct ccgcacgcg aacagtgcgt    3480 tctcgtccgc tgaggccgag gctgtgctga tcgagtttgg tcgcttgtgt tagtgtccac    3540
tccaagttgt tgagtcgcga ccgtccattg gccacctgct gacaagctag cggagcggcg    3600
gcatcccgcg atcaagacga tatctgacga acacatgaat cgaggttcgc ctgatcgatc    3660
gctggcctgg cgcgacgaca acgactacga ctacgccgtg aacctaaaag atctcgacac    3720
cgccggtgga gcttcacaca ggtaggaaaa aggggcatgg aactgcgtga aagtgagcct    3780
cacgcaccca acctccacgg gaacatgatc gacggctcga cgccgccgcc ggctagagtc    3840
tagagcagcc ggcgcccgac gcccgaggcg agcggcatgg ctgggcgagc gaaaaggcag    3900
```

```
gtaggggtag gcgtagcgga ctatgggagg gacaggggag cgcggtggtg gggcgcatgt      3960
ggctttcacc tcctggccac acacacagac ggcgacaccg agctgagcag agctgatgcc      4020
gtggcccggg gaccatcgct gcggtgctgc ctgccgcgcc cgcgctcccg cgcgctaccc      4080
gtcctcctgt gccgtagccc ctgcctgttc agactgcgcg agccgggatg cgcgcacgtc      4140
accggtttgc ggccggcaca gacgcaaacc acccgattgg ttcgctgcac gcgagaggcc      4200
aaagctttgc acgagcctgg tcggggatac                                       4230

<210> SEQ ID NO 7
<211> LENGTH: 993
<212> TYPE: DNA
<213> ORGANISM: Zea mays

<400> SEQUENCE: 7
gtaagcctac attcagatct aaaaaccttc actctaggag ttggatgtgg ataaagctac        60
gaaccatact tgtaaccatc tcactaacca acccaaaact tctgtacctg catcgtatat       120
gtgtttatcg tgaatgtatc tacttgtatt tatatatcaa taaaactgaa tcaaaatcag       180
cagcacgtcg ttgaacaaac aaggacaaag acacactaaa ctcatccatc aattcttcca       240
ctcatccatc ttcttggaac acaatcaagg tagctaacaa gctccggagc tccaatccgt       300
gccttgcctg aacggagctg aaccgacctc atcctagtcg gtcatgtatc gcaagttgca       360
aggcaaggtc ataaacctag caaaaataaa cagaacaggc ccgggctgga agcagccgag       420
ctggacgccc ggacccctcg atggaaaaag aagagaaggg gaaaaagggg taagaagctg       480
ggcctcgatt acccaccccg aagcgcttcg gatcggtcgg cggtctcttc cccatcgatc       540
acgcgcgcgg ccgcggcctg cccgaaccga cgccgagcga cacgccgggc gatgcggtca       600
gcaacccggc cctacactgc aaaggaacgc gagcgtcaga acgtcctgag gcagcggcgg       660 ggtcggggc ggaggtggag gaaggggatc cggcgaaccc tcgaggtcgc ggcggtggac       720
ggcgacgcac gccaagcggg ccgttactgg gttggcgacg gagaggggaa cggacagaaa       780
agggtgttgg ccggacaccc ttttttatcca gcgtggcatg ggcgcttttc cacgtggacg       840
tacgacgctg cgatagacac ctggcagata atatctgacg ggcggatgga caggacgggc       900
gggccgagcg ctggcgccag caggccgcag tacctggagg ctggggcccc ctccgtggtc       960
aggcacgccg tcgcctgtcg gagtcggact atc                                    993

<210> SEQ ID NO 8
<211> LENGTH: 484
<212> TYPE: DNA
<213> ORGANISM: Zea mays

<400> SEQUENCE: 8
gaaatggctg ttaacaggca cgaaatgacc cgaatcgaag cctacagtca ccactcgact        60
gccaatcaca cgaccaccaa tcccttccct tgtccacggc ctgcacgaaa agttgtattc       120
attgtccacg gcccgtaggc gaaggcgagg cccatttagc tttatgtctt gcctagccag       180
aaaccctaaa acgccaccaa tcccttccct tatccgctgt ccgcctgtcc ggttctccct       240
gaccctgagc cgctcccgta gtcccgtccc aagtggccag gtccagctcc aggagctcca       300
ggcctccagc gcgcgtcgcc gccactttac gcccgtgccc agcgcccagg tagcttacg       360 cccgtgccta gcgccgccac cttacgcccg tgccagcgc tctaggcccc taggtagctt       420
acgctccagg cctccaggct ccagacctcc agtgcccagg atacatattt gattatatgt       480
``` ttcc                                                                      484

<210> SEQ ID NO 9
<211> LENGTH: 2273
<212> TYPE: DNA
<213> ORGANISM: Zea mays

<400> SEQUENCE: 9

| | |
|---|---:|
| cgaaaataga gggtaagtta aaatctgtca tagaatagac aatctccggc agttctgaga | 60 |
| atcaagacgt tggctttatg gaagccctgc gtggaagtgg gattagacaa tctccggcag | 120 |
| ttctgctatt ccatttctta tcccatctta tttgaagctc tagtatgcaa gtggcaaaac | 180 |
| attgttttgt atagacatat acacaatcgc tggacacagc ccagcctacg acggggtcgt | 240 |
| actctactca cactgtaaac gaaacaacgc aggtctttgc tggtgccgat gattccggtc | 300 |
| aagagtcatc aaactccctg tctgtaatcg ttgcaattgc taacgtgtgc atcgtcattc | 360 |
| gacaaaaccg caacaccgta ccccaggcag cattcttctt cgcgcaagag cagagcttat | 420 |
| tttaggaagc ccgcaaacct cacctctgca acagccagca ggcggaccaa caacagcct | 480 |
| gcactgcaga agctgcaatc ggcaccatac acgtaccaat tcaaattcgg ctgcaatggc | 540 |
| ggggaattta atacgaatgc atacacacgc cccatagcgt acgacagcag tagatccaat | 600 |
| cagcaatcac cactactcat gccaaattgt aaagtttcag gcgctatccg atcaaggaca | 660 |
| gtgctaaaat taccgtcggt gctagctgct gccctgccca atctgttaac gttccatttt | 720 |
| attcacccgt ttgactcgac gaaggtaggc actatggtcc cacatgtcat ccatgtgcat | 780 |
| gcatgccacc acatccgtta ttgtccattg caaaatcgtg tagagagaag cgggccacga | 840 |
| cagtctatct agtctttgat tgcttctttt ctgaatgaat accacggtac ggtatccccc | 900 |
| gtagcatgag cattaaaact ttttaaaaaa gagagacaga gagaagaggt tcaataatca | 960 |
| atactacaga agataacgta acatgacccc ttgtagccta ttttccccca gattagccgg | 1020 |
| tgcccgcggt cacccctttca aacttgcttc gccaatcgcc atgggggggtg cggcgtgcct | 1080 |
| tgtggaggac catttgcatt ccaatcgcgc tagatgttcg cgccatgcgc tggcactggc | 1140 |
| agtggcaagc aaaccgcgct ccttcaaaaa ataaaatgcc gcatttcgct gctacgaaca | 1200 |
| acggacatgg ctggcccagc gggccttgtg cctccttcct ccggtaacca cccaaccaac | 1260 |
| ctcaataaaa cagcaccccc gatctccatc cgtgcgcagg tgtcttgaaa agaaagaagc | 1320 |
| ttctccgttc gcacgcagac gcagcgactc gcaggcagat agatgcggcc aggccaggcg | 1380 |
| cccggcacag ctggagcgct tgctgcgcc tgcacggctc ggctcggctg gccctggcct | 1440 |
| gcctctgctc tgcctgcctg gcacaccact gccgctcgcc tgctccagcg cagcggcagg | 1500 |
| gcacgtgcgc gcgccagcca gcccggcgcg atccgtctaa tcgccgcgat tgggagggac | 1560 |
| ctgctctggc tgtggctgga atccgagccg gtgggcgatg gcgcacaact tgcactgcag | 1620 |
| tactagtacg agccacgtgg gtgccgtccc gccggcccc attagctgtg cccagcctgg | 1680 |
| acggagtacg gacggacacc aggagtccag gacatggaca ctcgcactcc gctccgtcct | 1740 |
| ctctcgcgta acagcgcacg cctctcatcc ttcgctgcct cgtggggggcc acaggcgggt | 1800 |
| gctctggtct ctgtgggcga cgccgagctg gctgaccgga ccggattagt taacggcagc | 1860 |
| cggggaatgg aattaacgcg cgtgttttt ataattgagg tggcggatac catacgtgca | 1920 |
| ggcccgccgt ggacggagct gcggctgctg gacagcacag cgtcggcctt tttcttttc | 1980 |
| tctcggtact agtacaaagt acaaagataa aaatacattt gttttcgaga tcagcgatga | 2040 |
| gtcatcgcca tgcagtgcgc gctgttcact gcacgtccac tccagcagtg ggcagtggcc | 2100 |

```
cgctggtggc gttctcccgc tgagtcagcc gagtccgcgc ccgtgcgtct ctgtctcgtg    2160
acgaatccgg ccctctgtgg ctgtcacatg acggatccgg ccctcggaca ccctggatta    2220
gctccagtat ttaaagaaag gttggtttag tggatgaggg caccagctga gct           2273
```

<210> SEQ ID NO 10
<211> LENGTH: 1213
<212> TYPE: DNA
<213> ORGANISM: Zea mays

<400> SEQUENCE: 10

```
tgattcactg atatccaaca tgttatcagc acgatcgcaa gattacagaa gaggaatctg      60
aaactcgcta gatggatcgc aggggccatg ctctcacttc tgacttgagg acagtaacca    120
gtgcggttgg ccattgttga tgcgacacga ggtatatcag tcatccatca tcatgattaa    180
tgattaaggc tagaaaaatt gcctctgcat catcacgtcg ccgagaactg ggaaagtcct    240
tgtgcgcgct acaggtcgac gtggccagtg gggccggcac cgccaaggcc gtcgcggcta    300
tgcccatgcc gacggatgcc ggaggcagtc acgccgtggg aatccacacc gtgcgcgcca    360
cgaagggcct cgcacccgt gtcacgccgc cggaccgcgc tttcgcgcca tggccgtatc     420
tgcgcaaggg tacggcaccc gcgtgccggg ggctgtaacc gtacgcgcct gggaccgcgc    480
gcccgtgccg ccacacctgg ccgttacagc acaccagggc tccgtcgtcg cgtgcggagg    540
atgcggtcgt gcacgcagat cggggcctag gccggtgccc gcgcgcctgc gctgccaggg    600
ggctgtgccc cgtgcagccg agcccggacc gccgtcgggg ctgcctcacc cgcccgccg    660 ccgaggctgg gggccgcgtc gcctccggtg ccgaggctgg gtgccacgca cccgcctggc    720
tgcctgcacc gccggagccg ccaggggcga gaccgtgacc gctcctggtc gggccgacca    780
ccggcgagtc ggggctaggg cccgcgcgcg cctggccgag gccggggaag gaggccgcgc    840
ccgccgctcc tggccgggcc acccgctggc gagccggggc tggggctgc gccagccgca     900 atgagaccgc gccatggccg ggtctggccc gtcgccgggg ccgaagcgct cggctgctca    960
ggctcgagca ccgcgcgagg ccgcgctgtg gcctgcctgt gcgcccgcgt ggcagcggct    1020
tgcgcacccg cgaggcggcg gcggtggcgg cgccctgctg ctggtggaag agagagaggg    1080
ccgcgacaag acgagttagg aaaccctaac tgcttgccca cctcctatag gccgcaaatg    1140
ggctggctgt tttggcccat ttcgacaagg attattttttt ttggctgaat atatttacaa    1200
ttattatcat cac                                                        1213
```

<210> SEQ ID NO 11
<211> LENGTH: 1393
<212> TYPE: DNA
<213> ORGANISM: Zea mays

<400> SEQUENCE: 11

```
gcctgggccg ccactgctca ttttcggccc acttcattaa cccgccgcgt ggcccgatta      60
cccccacgcc cgcgcgcgca gtcaccctac cgggtccttc gctgaccagc ggggcccaat    120
cgtcatcttc ttccccccact tactcgacgg ctcgacgcag acccaatctc aacagaaatc    180
gccgcatgac tcggatcccg ctactgcttc cctggccgtg cggctgtagc gctactgacg    240
ggcaggcccg ctgaccaacc ttcccatcgc gcacggactt cttttcgcacg cctagcgagt    300 ggagcgcgga ttggtcatcg ggtgagatcc gctgcaagct cgtcttcatc ctctcgtgat    360
taccgtggac tccgcgcaac agaaatccaa gcatcgcggc ctagcaaatc ccatcagagt    420
```

```
tcgattccaa cctgcatata attgtgccct catactaccg cacccagatg cataggacgt    480
tcgggtcttc gcgtgcgcca gggagacatc taccgccatg aaacagagag accgaaggag    540
gaagaattgt tgttcctgtt tcttgggatt cttctactat tcaggcgttc atccctcttt    600
ctctcgtggc gacgaagacg accgacgccg acgccctgcg cctggtgcca ggttccgtcg    660
ggtcttcgcc ggcgatggac atccaccatg gccgactggc gagagagaga aaggcaacaa    720
gagcgagaga cgggtgtgt tgccatcggg agggagttca acggagccgt gcactggacg     780
tccaagactt ccctgtgcgt gcggtgtaga gcagacctgg cctcctcgcc gggcgtgaag    840
actgcgcgaa cgccgtcgag tcgtggacct gggcgtgctt caaagagcgc cgcggtttgg    900
ccttgccatc ttgatcgacc ggtaaaattc tttccaccct gttcgcatta acacccctc    960 cgcgtagcac tcttcagatc cgggttttgg gaaccagaga gggaaactat gcatctccgg    1020
cgaacttcat tgtcgtgagc ttggcagcgc cgccgcgcgt gggctgcttg atggggttgt    1080
agctggagaa aggaacagtg gctgtcggat aggcgatgga tggacgagat tatggcatcg    1140 tataccccctt cgcgcgatcg gatttgggcc gtagatgcga aatcgggccg ttctgatttg    1200
gttagggcgt ggcaagtcat cgaccgttga tcccatatcc aatggaccta gttgcataca    1260
gattcgttat atttgagatc taaccctagc ccttgatttt taatccaacg gctcagaact    1320
acagataccc tttcggcctg gaagacttgc ataagagcca ctctgctttt ctagaataaa    1380
cccgcagtcc acg                                                       1393

<210> SEQ ID NO 12
<211> LENGTH: 1201
<212> TYPE: DNA
<213> ORGANISM: Zea mays

<400> SEQUENCE: 12
ggcccaactc tgccattggt gcctctcacc tgggagcctg gcatgtcggc ccagcttgtc     60
agggtcgtct tcaagctgga ggctcacccg agatctgctc ggtgattttc actacttcgt    120
ccacctttcc cctcggccat gtgcgctctc tgttgcccgg atggctgacc gcgagatggg    180
ggcgctagac attctttccc ctctcaatct cgcacatgga gtaaacatcg ggttgttttt    240
gttgtggtaa cagcccaaaa atcccgccta tcaagcaccc ttaggctcgg actgtcctac    300
cccggtgata aatacctggg tacgcacccc ccttggcga actcctgtcg agccccgcct     360
tagagcacgt cgttgcggcg agtagctggg aaggagatgg agggccacca tgcagggtgg    420
gtgaagatct ggttcaccgg cattgtgccc tcggcgttg gcaggggtc ttcctcgtgt      480 ctcatggggg acgcccatga cctcatcagg tgaacttgaa accgtggtg catggaattg     540 ctcaacggaa tgtatggcca ccaccatgtc gcaggtcctc gaggccatga tcctctgatg    600
ctccagtcct taggtaaggt ccccagacat cttcgctatt ttcgtagcac cgtttagaat    660
caatcggatc gggggtttga tcctgggtgc acggattcgg ctttctctgg cgggccctcc    720
accgtgggca gggcgcctcc accgtcggta agttcgtgt gggagaagac gcgtgggggc     780
catcagatcg aaaatggatg gacacgataa gatctcgcgt atcgttcgga catgggggaa    840
tggtgaccgt ccgatcgtca ggaacaatgt agatttgact aggtatgcgc tctgaactcc    900
gcgtccttcc acctttcgat cttgatcggt ggggcgtggg taattaaggc ttctataaca    960
tcctgaccgt cgatcttcga atcaacaacc tcaagcgtgt accgcttggg ttaaagccag    1020
atctaatcca caccattggg atcggatctg acaattggga gcacgttctg gttcgtctgg    1080
ggtccgatct aatcctgacg gtgggcttgt gatccaacag tcctagtcga agcgtacctc    1140
```

```
ttcggccatg taaatttgca aaagaatcct taaatgtttt aagaatcaac ccgcgctcca    1200
c                                                                   1201
```

<210> SEQ ID NO 13
<211> LENGTH: 1195
<212> TYPE: DNA
<213> ORGANISM: Zea mays

<400> SEQUENCE: 13

```
gacatgccag gcggaccagg caccggccca gcctggctgg ccggcccagg aggcccaaca      60
agggtccaaa acgcctatta tgagggcgg ctagggtttc aaaccctaac cgcccacagc     120
tcctgcagta gccgccacca gggagccgcc gccccgtccg aggccggact gtgccctggc     180
tggggccggt agccgcgacc aggcaagggg cgaccgcgcc ctcgccggga tccaggcgct     240
cgccatgcgc cgtggtccgc gaccgccttg gagagccgcc acggcctccg tcgggccgcc     300
cgcagtctgc tccatccggc gccaggagca gcagcgcctg ggcgtcctcg tcatgcgtgc     360
cggtgtcagc caaccccgca ccaggaggcg ccacgccga actccgcgag aggccgaccg     420
cgcccgacgt gccggatcc gcaccggcgg tcggtgtggc agggacgtgc cgcttgcgca     480
gagatgcaga gcaccgttc aggcgtccac ccgttgacgg ccgagcgtcc gtgcccacgc     540
tggcaactgg ccgcgtccga gccggggac ggccgcagcg tgcccgcgcc ggggcgctcg     600
gcggccgggg cgctcggcgg ccggggcttg cccgcactgg ggctcgaccg cgcgtaaccg     660
aggctgtccc gcgccgtggt cggttcttgc cggactgcgc ttggtcgcga gcggccaagg     720
gctcgcaacg gccgtgccgt gtccattgga ctggccgggg tcgtgcctca cccgcgccga     780
agtgcacctg gcacatgcg gccaagggct cgcagcggcc ggtgccatgt ccggtgggct     840
ggccgcatgg cttcgtgtgg ggagcctgca tggccctccc tgtgcatgag ccgcatggcc     900
ctgtgtaggc aggcagacgc accgcgcatg gccgaggcgc gctgctctgc gcatggcctt     960
gttgtgcatg gcccgcaccg tcggtgcgct ggggacaggg cttgtccgcg ccgagccttg    1020
ccgtcgcggc gccgtccggt gtggtatagt tgtggccacc gacgacataa aaatttcacg    1080
catacagtga aagcggagag gaagagtagg ttccatacca ttatccttct ccaactagga    1140
gcgatctgtt ttcttcctac cagcaatttc tctccgtttt ctcgcgagtc gtgct         1195
```

<210> SEQ ID NO 14
<211> LENGTH: 1176
<212> TYPE: DNA
<213> ORGANISM: Zea mays

<400> SEQUENCE: 14

```
gaacctaagg ttggaccagc acgcaacgct atctgcagga tcaaagatcg acaggctaga      60
ttttaaacac caagatccac tccaatccgt acgatctgag atctatattt gatcccttcg     120
aagcggtcct aattatctaa tcaagaccga tcagatcgag atcgacgact cctactctct     180
ctcccttatt cccctcaatg ccttcggacc gaggccacca tggaggcgcc atggccgaga     240
ccggactatg agctccctca tgaatcccc ttcaaattga aacttagcta cacattgctg     300
agactaaggc gagtagttct agggctctct tacctggagt tggacgacg aggcacccca     360
cccacgtgtt ctgcggttcg gcactggaag gcatgctccg gcgacgaatt cctctatgcc     420
cgaccaccat tcgccttaac gcacgctgct ccccacttcg gtgccctccg tggaacgatt     480
ctgcgcgcac accgagggcc tgacgctgcc atacgtgaat ctatcatagc gactgcttct     540
```

```
ctatgctctt tctctgtttc tactatggcg ccgggtgggt ttgctctcgg ctctagggga       600
tgatgggggg ttgctcggcg tctggtttta tagaccctag cgtgggcaag accgaaagac       660
tcggggtcgg ggtcggggtt acccattttc tggtgaagtt tgttgtggca tctgtgcaat       720
cttgtctagg aagaagactc tggacagctg ggcccgttta tcaggttaa gggaacgtgg        780 cgcggagcgg ctgattaggc tgacgacccg gccccagtcg tcagcggcaa aagacgttcg       840
ggctgaggaa agccagagct gacgaggcgg ggcccgcgcg ccatacacac tggaaaaaga      900
aaaaggaggg aaacgtaatg ggccagcgag gcatatttgg cccatcagga cagggtggac       960
gccgagaggt agttgggtcg aggagaggtt caagcccaa acgaggtat gtcctctctt         1020 tccaatttgt ttagatttct tttagtgttc taaattctaa cttcaagttt tgatttaatc       1080
tgccgttaaa attttgaact caatttaaat gcgcaaccaa aaatacccag catgatgcag      1140
caatattcat atattttgca ttattttaat aattta                                 1176

<210> SEQ ID NO 15
<211> LENGTH: 913
<212> TYPE: DNA
<213> ORGANISM: Zea mays

<400> SEQUENCE: 15
ccctttgtcg cgtgcggccc attcctcact cgccctgcct caccgacgtg tgggtcctag        60
cgctcctcct ctcttggtgt ctatggcatg tgggccgtct ggccagaccg tttcaacacg       120
caagggcgca agcctgtcgc gagtcttgta cacgctgaca tgtggcaccc ggtcgtcatc       180
actaacccct caatcgaaga caccacaaca gaatagcggc gccaggtttc tcggtcgggc       240
cgctccaacc gccgttgccc gggtgtgcgg gtcagactcc atgctataaa gagctgagcc       300
ccgtacccct ggaacccttg gaccatctct cgccacccag aacaaggtaa cctcgtcgcc       360
atcaccatag ttgtggagca ccgccgcagt tggcgaggtg agatcccgcg gggcctcttc       420
aatccgagtc tgggggtggc aggctcccta gcgcaaccaa gtgggttcgg ttgtggggac       480
cggtggcacg cggagtacct cagagtggcg gcaattgctc gccgatgcat gccctctggt       540
gcggactacg cctcttcgtg ggcagcgaac tccacatctc tgacttaggt gagacccctc       600
tccgcatgtt cgccatcttc ccctctaggt ttagcaccgg acaattttag gtttggggtg       660
tttgggcatc ggattgcgtg tccgccggcg aagctccatc gcggcctcgc gggtatgcca       720
tgcggcgctg tcgtgttctt ctgggatggg agatatggtc acgtcagtcg attgctcgct       780
taacggctgc aattagatca aatgtacccc ttcgcgcata cgatccggg ttgccgattc        840 ttgatcaggc ggtcaaaatc aaatccggat atcggtttgg gtaggtgtaa cataagtcat       900
tcgattcaga tca                                                         913

<210> SEQ ID NO 16
<211> LENGTH: 1149
<212> TYPE: DNA
<213> ORGANISM: Zea mays

<400> SEQUENCE: 16
aattttgaag aaaacaata aaaagggga taaagaaaaa gcttaccttc ggttgggccg         60
gcttcctcat cccagggccc aacttggcac accagcgcgg cccactcagt cctccccacc     120
ttttgctacg cgacacacgc tgacaacagg gccccacgcg ccagtccctc accccacgg      180 ccgcagcgcg ccttgtctcg ttgacgcatg ggtccgagcc gtcagcttcc ttttctccag    240
cgttgtagat cccgcggcgc ggccgccgta cctcggaccg ggttttcgcg tgcgtgaatc    300
```

```
tgtctccgtg tgtttctgcc accgtgtggg accatccctg gccatgctgt gccccatccg     360
tgcgtagaaa tcggatcgaa acagactctt ccccgctcaa atcggggatc gcaacagcat     420 tgggcgggc tctcggaggc tataaaaaaa ccgtgtcctt gggctctctt cctccgtctc      480
atcctccgtg attgccatcc atcgccggcg tgtggctcta acatcgcaa tttctcatcg      540 gtctgatgcg ggcaccaccg tgtcgcccta cccgtggcca gcgctcgttt cgtcgcggtt     600
cgccggtaag ccaccccata cagttccctg gcccctgggc atcgtgtcgg tcacttcgga     660
gtagaggata gggctagatc gtctccggcg atgtccgcca ccgtctacac ccacggcgcc     720
accgttcgtc gcccgcttgg gggggctga agcggtgtgt gggattgtcc gtcgtcggat      780
gctcgttcga cgatcgggat cgggtgctgg acctgagagg atatatgaat ctggggtcgt     840
ccgatcgttg ttgagcggat gagattagat cgcacaaaca atgcttcagg tatgtagatc     900
tggagcattg gtctgcgggc tgccagctag gattaggggt cgggtaacga ttcggtatgg     960
ggccatctcg accgttgatc ggctgacgtt cgacccagaa cggaacatgc aatgccgcta    1020
tgttgtattt gctaaagaga ccccgtaga tagttaaatc aacccgcggt ccactgctgt     1080
gtaaaagcaa ttacacttgg gtcttgaaat tcacagatca gaccctgggg tttataagaa    1140
tcgtgtccg                                                             1149
```

<210> SEQ ID NO 17
<211> LENGTH: 2363
<212> TYPE: DNA
<213> ORGANISM: Zea mays

<400> SEQUENCE: 17

```
tttgtatgga attgttgatc ccacgctctt tagttgcacc ggagcacata tatatttgta      60 tggcctttt ctccgtttgc ctctccgcca tcgagcctat atgcttaaca agttgataca     120
actgttgctt cgtaataata gagattagac agggttgttg tatatgcacg tccatttctc    180
tattcgattt tggaaatatg tggcgtcggc gaattaacca tggaatacaa aggctatata    240
attaattaac ctgtatatat gacacgttag gtaataatat aatgcatcga atgaccaata    300
tatggtacag tgaaatgtaa ttatggaggg agggagggag gttttttgttt acatgtcat    360 cacagattcg aaaactgtca cgcatcaaac ttttttctctg catatatatg ctacaaagta   420
gctaggaatt agacaagcag gttgtcgcac atgcacctag ctgagacgtt gtcagatgat    480
tatatattat gcaattatgc acgtacgtcc gtaaaacttt ttttgttctc tctcagcatg    540
catggtagct agagatgact agctgcagag tagcaggaac gttgcactag ctagggtacg    600
tacgatatga aatgggcttt cggccggggt acacgtgata taggccggcc ccacggccac    660
tgcaaggcca tgcatgtttg tcgacttgac attatattat atatattacc ctaggcaggc    720
taattattcc aacaccgatt ggttagcaat acaaaaaaa aaaatcaatg cccagacatg     780
cacgaacacg acgatatcta catgcactcc gacatgtacg catgcatggt ccaccgtcca    840
cactctcgtg aatatcgaga cagcatgcgc gcgtggtagg taacgattgg gaaaaaaaat    900
aatgcgtgaa cgaacggtgc gtggatatga cacaccacca agacgtactg agacatacta    960
tttgtggcta ctaaacaatg tactcaccc atcctaaata agatcccaac cgtacgttgc    1020
tctctgttgg agcctagtgt gttggttggt ggattcatcc aatagggcgc ctaaacaaat    1080
aaataatact ggcaggttcg tgcacgttag atctgtgtgg tccaccaaac aataatatat    1140
atgcaacaaa taaataatat tattgtgtgg tccaagcaat aatatgatgt gacccggccg    1200
```

-continued

```
ggccatgtcg tcgtcgtcga tcggtccctc catcacatgc aatgacgtgt taagttgtcg    1260
gaatatgctg cgtttggtcc cgtaaccatc tatcgtattc ctcagctagc tctcacagac    1320
tatatgtaca aaacacaaca agaagcaagg aaccaacagt gagattcgag gtgtgtggtg    1380
gtgacagcgg cagcttggat ttactctgtg tccgcgctca tattatgata attaattaat    1440
taattaatta ttgcatcgat cgaccgtgca tgtacgcaca cgtacagtac agaggacata    1500
aagaaagaaa gaaagctact ccacgagcgc acatgcatga tgttcgttgc ccatcgatgt    1560
caagctaggc agagtctctg tctcgtgtga ttattgatca gatacgacac gtttgtgtgc    1620
atgaaaaaaa agctgtctcg gtatggtgct gggccaggag agacagcagt ggctacgtat    1680
acgtattata gcatagcata gcagctatat tatattgttg gagagctcac cactccctca    1740
attctctcga tagtgatttt ctatgacact atgataaata atcttaaac cagaacatta    1800 ttttaaatca aagtggctat ataataatac tctacatata tggctagcta gctaggcacc    1860
gattctcttc aacattatat atatgtggct actcataaaa gcgggttgtt acgagcatat    1920
atggcgatta aattaacagt atactctgaa gctggcgatt caattcactg ttcatccgct    1980
atatcccctc ctcgtcgcga cagaagctgc gatggccacc aggggtgacg tggaggccct    2040
cagctgcggc ggcgcggagg agctcgaccg gtcaggagaa ccaccagggc agaggagctc    2100
ggccggcgcc atggaggaaa tctgcggcgg cggcggcacg gagaagcttg aatatgcggg    2160
cgcggaggag cttgaatatg cgaagaagct cttcggcagc atggaagcgt catgttgtta    2220
gccctgctat tagggtcaaa cccacccaaa ccctacaaat gagttatttt cttcaaccaa    2280
acccaccata taataattaa actaaataac ccacctaaat ccacccatag ctactgggtt    2340
aaacccatta cctaaacaca tgg                                           2363
```

<210> SEQ ID NO 18
<211> LENGTH: 1449
<212> TYPE: DNA
<213> ORGANISM: Zea mays

<400> SEQUENCE: 18

```
cgctagatgg gcatgttgat ccttgccaaa acgctcacac agtaggtgac aaaacacata      60
ccatgacatg tacactaatt tttgtttaac agattgcaac caacaggcag ctgcacctaa     120
aaaactcatt gtagcaactt tgatccacac cctatgactc attccataca tggcaaaata     180
atcttcataa tgtttctgcc aaagttttgg gttctcgcca tcgaaactag gaaagttaag     240
gagtggtaat tttcccaact ccaactctaa ccttgccctt ggtggcctag gatcatgata     300
ctcatgtgga tccagatgag aaagtggagg gtgaaacatg aaatcgggcg taccattgat     360
cgggagatgg ttttgggcaa ggagatgccc aaaaccatgc ccccagcgat ttttgtcgaa     420
gcaattccca tctgggctgt cggtgttgta cgcggcagca ggcgagcgct ccgccaccga     480
ctggtacggg ccgagaatac ccgcggcggt atcgagctgt ggcggcggcg cttgggcagc     540
ccacttggac acctcgtcac gcagaagatg cacggaggtg tggatctcgt cgaccgaagc     600
ctccacgtcg ggccgccacg actcgaaggc cgcgtaagcc gacacgaggg caccgaggcg     660
cattacgaaa gcggcctcga cttcatcgag gcgctcgatc gctgcggtga cctgggcgtc     720
gagttccacg tggatcgatg tcagactctc gatggcgatg ttggcttcca gatgttgcgg     780
tgacgcggtg ttccacgcga cggttgtctc gagcgtgcac caacgcgtct cctgagcaaa     840
gaggtggtca cagatgtcgc gaagaagctt ggattgttcc tcgatcgcca tcttcaggtt     900
gggctccatg gatccggatt ccttcgcgcg acgcgtgtag taggtgtgtg ctagcgctta     960
```

```
gatcagtgtc tccgatatca atttgtgagc gtccgctcca agcaacataa tctaggaatg    1020
acgagagtag gagaagggag attctagagg aagaaggaga tctgataggg aggggaagta    1080
gttgttcgat atatttctct gcctaaaatc gtcacagtgc ctgttcacag tatttaagta    1140
tcaactatta caaggctcga cggcccatta tgccacccag tcctctccta ggaacttggc    1200
attgggcttc ctgatgcggc ggcccaactc cagcccagcc acgtccgacg acgacgcctg    1260
cttcttgacg cacgtcacct gggcgatgct gagagtgctg gttacctgta atcggataca    1320
acgtaatcaa tcggatacat gacatatatt tttcttagtg ctcctccggc tccgtgatcg    1380
gatcacgctg ctgcatctta taagctgaaa gaaactggga aggtgatgag ttggaccttg    1440
tgctgcccg                                                             1449

<210> SEQ ID NO 19
<211> LENGTH: 1105
<212> TYPE: DNA
<213> ORGANISM: Zea mays

<400> SEQUENCE: 19
tgaccagcat tgatacacct gatatgtcaa tcgcctttaa cgaaacaaga ataagaagcc      60
tctcgggggt agcaataaga aactccggct cacaagtttt cagtccagag atctagtgtt     120
caatggatgc gccaggatgc aagctcactg aatgaatccc aagaggcttc aggggtttgc     180
atatcgatcg cacttgcgcg gccttatcct gtgacgagac gaggtacagc aggaaggggc     240
aagacacgac catcccatgc ctctctttcc tagcgacgat gtcgcaggca gtggagacga     300
gccacgcggt ctgcgtcacc gtggcgcacg cgccgctagc gtcgagcacg tcggacggtg     360
cctgggtgga gcaacacctc cagagctcca tgccccggtc accggcgcca tggatgctgc     420
cgccgccttt ctcgggcgcc accgcatccc ggatagcgtt gaggcagacc accaggaact     480
tggacagccg gtcgaagtcc ccgtggccct catccacgcc cgtcgccctt cgccatctcg     540
gctgtgctgg ctaggtcgct tcggcgagat agccgccaac cgtcggggag tggaggggtg     600
ggaggtcgac aggagcacga gcagttgggc ggttcttggc ggaatgggag cgcacatcac     660 gaaagagtgcc taaagaagat gcacagttgc ttagggtggc cggtgggccc ggcggcgcta     720
gggcaggcac aacgctcgcc catgcgggag cgaggcacga tggccagacg cgttctcgcg     780
agcgcactgg gtgggtcgcg gttgctgggc cagggagggg gcgctggcct ggcggcctgg     840
gcgtgggcgc ctgtgcgctg ggccacgcgg ggtgggccgg ccacgcacgc gtaggagcg     900 agccaggac gcggggcagc tgggccgttg gcgcgcgcag cggcccggga gcgcgagcag     960
gatgcggggg gaaggcgaag gcgcgtgggc cggggtggcc gagcggccca ggaagggggg    1020
ggaacgggcc acgattgggg aaaatgaagg ggaaagaatt ctgggctttt tcttttatgt    1080
tcctcttctt ttctttgtcc atttc                                         1105

<210> SEQ ID NO 20
<211> LENGTH: 280
<212> TYPE: DNA
<213> ORGANISM: Maize streak virus

<400> SEQUENCE: 20
ccgacgaccg aggcttgagc tggctcaagg cagaaacggg agctcccaaa ctctatccta      60
ccggtgcgcc ttcgaaatcc gccgtctgcc gtcttatata gctgatttat ttgggccgga     120
ctgggccggc ccagcaggaa aagaaggcgc gcactaatat taccgcgcct tctttttctg     180
```

```
cgagggcccg aagggaccga gcgtctttga tttaaagttt ggttctgctt tgtttgattt      240
taccaaagct gccgcaacta aagacgccgg tccaggcgac                           280
```

<210> SEQ ID NO 21
<211> LENGTH: 1102
<212> TYPE: DNA
<213> ORGANISM: Zea mays

<400> SEQUENCE: 21

```
catgtgtgtt gtgcgagacc agccacgccg atacagttac tgtgctcacg ataaaattga      60
aaaggacaac cccattgttc cagtcattta gtcatggaag aaatgatcct ttccaaccca     120
atctcctagc cttttttctt cgaaagaaag gaagatctgc ccgttttttat ctattcccgc    180 ccgcaacaag atcgatgatt acccaccagt aaaattccga aagcctaca cctaccacaa     240 acttcctctt tttttttttg gttgttgttg tttgagaaaa gaagaagtcc ataaagcaag    300
attcccgtag gtgggcactg ggcatgcgat gcaaggacag gtccatcagt ccatccgtca    360
gtcagggaat agcagctgcg gtgcaggagc acgcacaccc agctccctcc ctcccttgtt    420
cccaatcatt tgctcgctct acgtgctcct gctcttcacc gtcggaggga acgggtcttg    480
tctgacggta cagtcctcag caaggattac cggtaaacac ggcatcgttt atctgtaaac    540
ttaaactagc actggattta acaagcgcac aagctagtgg acactgaaca ggccccccgg    600
ccgtgccata caatcaggtg gtaataatgc agcaattatg cggctgctta ccctggggc     660 tgggggggtgg aagccaata atgttacctc gctgacagaa aaacgcatag ggaggaattc    720 cttttccggat tcccttgggt ccacaatcaa tccccttgct tttccctcgc cggtgcctga   780
gtgactctga tgagctcttt ggcaaatgga tgacctgtgt ggaactctga tgagctcttt    840
ggcaaatgga tgacctgtgt ggcttggcca aatggtgagt gagtggagcg gagcagctgc    900
cgctcactca gctcctcctc gactcgcccc gggcatcatt cacgaatctg cttttccccc    960
agccccggaa atacgtttaa aggaggccgt tttcagggac gagatgaggt tgattaaagc   1020
aaagcagagc agagcagagc taagcttct tgattccttc ccagaatgtc gctcgagctt   1080
taggcaggca ggtgactgaa aa                                             1102
```

<210> SEQ ID NO 22
<211> LENGTH: 549
<212> TYPE: DNA
<213> ORGANISM: Zea mays

<400> SEQUENCE: 22

```
cggcgcttgg gccaaatctt tccccctcg acctaggtag aatcacctgc accggcccat       60
ctccgtggtc tccacggctc aaactcccgc tgtgctggtg cctttggtga ctgccagggc    120
agacccacta ttcagttcca cctctgcgcc aatgactgat gggtctgcct catcatccgc    180
ggttccccat ccacgtgctc ctgctatcac cgtcgtgtgg gccatgtttg tcagtattct    240
cctcaagctc aggatcttaa ccaatcccgc gctgctcact gatatggttg ggaggcaggt    300
gctgggatcc ctgacctcgg tgcattgggc gctcaccttg tccctataaa ttgtcgtgac    360
cgtccctcgc attgaaaacc caagccgaag taccgacacc gtgattacag agattgcaca    420
aggaagagca gggtgaagtc cgccattgga atctgccgtc gtcaactatg catcatgggc    480
atcaccgtcg aaccatcggg caccagccgg ggagcttcgc catggcgcga ggaacgtttt    540
cgtggcccc                                                            549
```

```
<210> SEQ ID NO 23
<211> LENGTH: 92
<212> TYPE: DNA
<213> ORGANISM: Agrobacterium tumefaciens

<400> SEQUENCE: 23
tcaagagcgg agaattaagg gagtcacgtt ttgaccccg ccgatgacgc gggacaagcc      60
gttttacgtt tggaactgac agaaccgcaa cg                                   92

<210> SEQ ID NO 24
<211> LENGTH: 331
<212> TYPE: DNA
<213> ORGANISM: Figwort Mosaic Virus

<400> SEQUENCE: 24
atcaatgaag aatcttcaat caaagtaaac tactgttcca gcacatgcat cttggtcagt      60
aagtttcaga aaagacatc caccgaagac ttaaagttag tgggcatctt tgaaagtaat     120
cttgtcaaca tcgagcagct ggcttgtggg gaccagacaa aaaaggaatg gtgcagaatt     180
gttaggcgca cctaccaaaa gcatctttgc ctttattgca agataaagc agattcctct     240 agtacaagtg gggaacaaaa taacgtgaa aagagctgtc ctgacagccc actcactatt     300
gcgtttgacg aacgcagtga cgaccacaaa a                                   331

<210> SEQ ID NO 25
<211> LENGTH: 293
<212> TYPE: DNA
<213> ORGANISM: Cauliflower mosaic caulimovirus

<400> SEQUENCE: 25
acttttcaac aaagggtatt atccggaaac ctcctcggat tccattgccc agctatctgt      60
cactttattg tgaagatagt ggaaaaggaa ggtggctcct acaaatgcca tcattgcgat     120
aaaggaaagg ctatcgttga agatgcctct gccgacagtg gtcccaaaga tggaccccca     180
cccacgagga gcatcgtgga aaagaagac gttccaacca cgtcttcaaa gcaagtggat     240
tgatgtgata tctccactga cgtaagggtt gacgaacaat cccactatcc ttc           293

<210> SEQ ID NO 26
<211> LENGTH: 416
<212> TYPE: DNA
<213> ORGANISM: Cassava vein mosaic virus

<400> SEQUENCE: 26
aaaattatcc attccagaag gtaattatcc aagatgtagc atcaagaatc caatgtttac      60
gggaaaaact atggaagtat tatgttagct cagcaagaag cagatcaata tgcggcacat     120
atgcaaccta tgttcaaaaa tgaagaatgt acagatacaa gatcctatac tgccagaata     180
cgaagaagaa tacgtagaaa ttgaaaaaga agaaccaggc gaagaaaaga atcttgaaga     240
cgtaagcact gacgacaaca atgaaaagaa gaagataagg tcggtgattg tgaaagagac     300
atagaggaca catgtaaggt ggaaaatgta agggcggaaa gtaaccttat cacaaaggaa     360
tcttatcccc cactacttat ccttttatat ttttccgtgt catttttgcc cttgag         416

<210> SEQ ID NO 27
<211> LENGTH: 401
<212> TYPE: DNA
<213> ORGANISM: Chlorella virus

<400> SEQUENCE: 27
```

| | |
|---|---:|
| caacggagtg gtcgtacata ctacaaatgg attgccaata gtattcgcaa tggatacaca | 60 |
| ccgaggttgt tgcgagaaat tttgtatcac ggtacaatta ccaggggggcc ttacgcgata | 120 |
| tgattttatt ggcgccacga ttacgaaggt aagatttggt aaagaaaaac gcaaatgcga | 180 |
| tattaatttt tcggaattaa ttatagaaac ttcggtagga aatatcgttt tactggcaga | 240 |
| aaacattcat aatggatatt actctcatga tgtattcgct tgttttgaag gtaaagttga | 300 |
| aacttttcgt ttgtaaatac aaaaaatgta tatgagtatt tgttgtcgga atgtcatatc | 360 |
| aacaatgttg tgtatatatg tgtaaactaa aatacactat a | 401 |

<210> SEQ ID NO 28
<211> LENGTH: 194
<212> TYPE: DNA
<213> ORGANISM: Figwort mosaic virus

<400> SEQUENCE: 28

| | |
|---|---:|
| agctgcttgt ggggaccaga caaaaaagga atggtgcaga attgttaggc gcacctacca | 60 |
| aaagcaactt tgcctttatt gcaaagataa agcagattcc tctagtacaa gtggggaaca | 120 |
| aaataacgtg gaaagagct gtcctgacag cccactcact attgcgtttg acgaacgcag | 180 |
| tgacgaccac aaaa | 194 |

<210> SEQ ID NO 29
<211> LENGTH: 351
<212> TYPE: DNA
<213> ORGANISM: Figwort mosaic virus

<400> SEQUENCE: 29

| | |
|---|---:|
| gagcgcttga cggtgttgaa ttaatttgca ggtatagttc aggaagcttc aaacaagcag | 60 |
| aaaagaatta tcacagcaat gataaagaat tactagcagt caagcaagta atcaccaagt | 120 |
| tttcagctta cctaacacca gtcaggttta cagtaagaac tgataacaaa aattttactt | 180 |
| atttccttag aattaatctt aaaggtgata gtaaacaagg acgattagtc cgttggcaaa | 240 |
| attggttcag caagtatcaa tttgatgtcg aacatcttga aggtgtaaaa aacgttttag | 300 |
| cagattgcct cacgagagat tttaatgctt aaaaacgtaa gcgctgacgt a | 351 |

<210> SEQ ID NO 30
<211> LENGTH: 381
<212> TYPE: DNA
<213> ORGANISM: Mirabilis mosaic virus

<400> SEQUENCE: 30

| | |
|---|---:|
| ggattaatgg attgatcaac atccttaccg ctatgggtaa gattgatgaa aagtcaaaaa | 60 |
| caaaaatcaa ttatgcacac cagcatgtgt tgatcaccag ctattgtggg acaccaattt | 120 |
| cgtccacaga catcaacatc ttatcgtcct ttgaagataa gataataatg ttgaagataa | 180 |
| gagtgggagc caccactaaa acattgcttt gtcaaaagct aaaaaagatg atgcccgaca | 240 |
| gccacttgtg tgaagcatgt gaagccggtc cctccactaa gaaaattagt gaagcatctt | 300 |
| ccagtggtcc ctccactcac agctcaatca gtgagcaaca ggacgaagga aatgacgtaa | 360 |
| gccatgacgt ctaatcccac a | 381 |

<210> SEQ ID NO 31
<211> LENGTH: 499
<212> TYPE: DNA
<213> ORGANISM: Cestrum yellow leaf curling virus

<400> SEQUENCE: 31

```
aagccatcga aaccggtcca ctggtaaacc ttcaagatga agaaagaaag attctttgcc      60
aaaaaatgca aaagtacaaa gggcacagct gtcagttgtg caaatccgag tcatctggac     120
cacaaacatc agaagagggt ctacaagagt cagaagacga agacttttcg gtgctagttt     180
aattactggc agacaaagtg gcagacatac tgtcccacaa atgaagatgg aatctgtaaa     240
agaaaacgcg tgaaataatg cgtctgacaa aggttaggtc ggctgccttt aatcaatacc     300
aaagtggtcc ctaccacgat ggaaaaactg tgcagtcggt ttggcttttt ctgacgaaca     360
aataagattc gtggccgaca ggtgggggtc caccatgtga aggcatcttc agactccaat     420
aatggagcaa tgacgtaagg gcttacgaaa taagtaaggg tagtttggga aatgtccact     480
cacccgtcag tctataaat                                                   499

<210> SEQ ID NO 32
<211> LENGTH: 371
<212> TYPE: DNA
<213> ORGANISM: Peanut chlorotic streak virus

<400> SEQUENCE: 32
atcatctgga gccaacaagc taggaagccg tctgagcaag atattcagat ccttacagag      60 ttttttacttc ggacagtcaa aaatgagttt aacttctcag ccgaggtaaa acaagaaata    120
tgcttacgtc tacagaggga tttctctgaa gatcatgttt gccagctatg cgaacaatca    180
tcgggagatc ttgagccaat caaagaggag tgatgtagac ctaaagcaat aatggagcca    240
tgacgtaagg gcttacgcca ttacgaaata attaaaggct gatgtgacct gtcggtctct    300
cagaaccttt acttttata tttggcgtgt attttaaat ttccacggca atgacgatgt      360
gacctgtgca t                                                          371

<210> SEQ ID NO 33
<211> LENGTH: 361
<212> TYPE: DNA
<213> ORGANISM: Rice Tungro bacilliform virus

<400> SEQUENCE: 33
aagaatttgg gtttgattac tacagttggg aaaatatggt tgatgaagac gaaggagaag      60
ttgtatacat ctccaagtat actaagatta tcaaagtcac taaagagcat gcatgggctt    120
ggccagaaca tgatggagac acaatgtcct gcaccacatc aatagaagat gaattgatcc    180
atcgtatgga caatgcttaa agaagcttta tcaaaagcaa ctttaagtac gaatcaataa    240
agaaggacca gaagatataa agcgggaaca tcttcacatg ctaccacatg ctagcatct    300 ttactttagc atctctatta ttgtaagagt gtgtaatgac cagtgtgccc ctggactcca    360
g                                                                      361

<210> SEQ ID NO 34
<211> LENGTH: 291
<212> TYPE: DNA
<213> ORGANISM: Sugar cane bacilliform virus

<400> SEQUENCE: 34
accaggccac accaagggct atgtcgccag tagccgcaga agatgtgcta gatctccaag      60
acgtaagcaa tgacgattga ggaggcattg acgtcaggga tgaccgcagc ggagagtact    120
gggcccattc agtggatgct ccactgagtt gtattattgt gtgcttttcg gacaagtgtg    180
ctgtccactt tcttttggca cctgtgccac tttattcctt gtctgccacg atgcctttgc    240
```

```
ttagcttgta agcaaggatc gcagtgcgtg tgtgacacca ccccccttcc g      291

<210> SEQ ID NO 35
<211> LENGTH: 281
<212> TYPE: DNA
<213> ORGANISM: Sugar cane bacilliform virus

<400> SEQUENCE: 35
gaacaccgtt cgagtgtcat cgacaggcca aggccaacag atgatcattt cagaccttgg      60
ggggatgtta catactggct gaataaagaa gcagaagagt gccacacaag ggcgacaac     120 gtcgaaggcg cagaagacgc agtcgatctc actgacgtaa gcaatgacga ccagtggagg    180
agatcgtaag caatgacgta tggagcgtgg aggacccatg aaagcactga gaaggcatct    240
caactttcgg tgtgtgagtg cgcatcctat gcgatgcttt g                        281

<210> SEQ ID NO 36
<211> LENGTH: 500
<212> TYPE: DNA
<213> ORGANISM: Blueberry Ringspot virus

<400> SEQUENCE: 36
ctacagaatt tcattggagt aattaatcat ttatctaatc tgacagcaaa cattaaaatg      60
ctgtataaat cagatacaat gattatctat tccaaagcaa caaggagat tgagccagat     120 caggaagcag tatttattga atttgaaaag aattttattg aaaataaaat tcccaaaatg    180
acgggggaga tgaagaaaga attatgcaat catatgacca agaagatca tccaggacac     240 tactgtccaa tattgtccat tcattcagca gggatgataa gaagtcagta tcaagtgaag    300
acgaagaaaa gatcacccat ggaagtggaa gaataaaacg tcttcatcca tcactatcaa    360
gacgtagaca tcacaatgta aagctacggg ctaatattag atggcttaag aatctacgcc    420
aatgtaaagt agattcccct tatctttat ttttaaagtt tttaagtccg gagttgagtt     480
ccgtcctgtg ggaattcctc                                                500

<210> SEQ ID NO 37
<211> LENGTH: 31
<212> TYPE: DNA
<213> ORGANISM: Carnation etched ring virus

<400> SEQUENCE: 37
cgttgcagga cattcagagg cattaaattg c                                    31

<210> SEQ ID NO 38
<211> LENGTH: 129
<212> TYPE: DNA
<213> ORGANISM: Carnation etched ring virus

<400> SEQUENCE: 38
ttggatggac cctaccacga ttaaagagga gcgtctgtct aaagtaaagt agatgcgtct      60
ttaataattc atctacttta gacgtcatgc atgacgttta acatgcattg tatccagatc    120
ctccctggc                                                            129

<210> SEQ ID NO 39
<211> LENGTH: 195
<212> TYPE: DNA
<213> ORGANISM: Commelina yellow mottle virus

<400> SEQUENCE: 39
cgccgtcatc aatgacatca tcacagtact gaggagatga atacttagcc atgaagtagc      60
```

```
gtgcgaatat tacctatgcc tttattcgca gcgttagtgg cactgaaagg cataaagttt    120
gttcgttctt atcaaaaacg aatcttatct ttgtaacttg gttacccggt atgccggttc    180
ccaagcttta tttcc                                                     195

<210> SEQ ID NO 40
<211> LENGTH: 159
<212> TYPE: DNA
<213> ORGANISM: Dahlia common mosaic virus

<400> SEQUENCE: 40
agtaaacaag gaaggttagt ccgatggcag atgtggctgt cccactacac attcaaagtt     60
gatcatctta aaggtgaaaa gaatgtgctg gctgattatc tcaccagaga atttcagcaa    120
aaacgtcagc aatgacgtca aatggccgat tcaaacggc                           159

<210> SEQ ID NO 41
<211> LENGTH: 275
<212> TYPE: DNA
<213> ORGANISM: Maize streak virus

<400> SEQUENCE: 41
cgacgacgga ggatgaggct aggggatggc agactgggag ctcccaaact ctatcctacc     60
ggtgcgcctt caaaatccgc cgctccccct cttatagtgg ttgtgtttgg gccggactgg    120
gccggcccgc gggaaaagaa ggcgcgcact aatattaccg cgccttcttt tcctgcgagg    180
gcccgcaagg gcccgagcga tttgatttaa agttcagatc tgctttgttt gatttatcta    240
aagcagccaa atctaaagaa accggtcccg ggcac                               275

<210> SEQ ID NO 42
<211> LENGTH: 278
<212> TYPE: DNA
<213> ORGANISM: Maize streak virus

<400> SEQUENCE: 42
ccgacgacgg aggatgatgc taggggatgg cagattggga gctcccaaac tctatcctac     60
cggtgcgcct tcgaaatccg ccgctgccct ctttatagtg gttgtattct gggccggacc    120
gggccggccc agcaggaaaa gaaggcgcgc actaatatta ccgcgccttc ttttcctgcg    180
agggcccgca agggcccgag cgatttgatt taaagtttag atctgctttg tttgatttat    240
ctaaagcagc ccaatctaaa gaaaccggtc ccggtcac                            278

<210> SEQ ID NO 43
<211> LENGTH: 296
<212> TYPE: DNA
<213> ORGANISM: Maize streak virus

<400> SEQUENCE: 43
atccgacgac ggaggctgcc gctagcgaag gcagggatgg gagctctaac aaactctcct     60
acagctcgcc aagtttgttg ccgccgcgga gagagaaact ccatcggctt atatagttgt    120
tctaatgggc cggaccgggc cggcccagca ggtaaagggg gcgagcaata atattacctc    180
gcccccttta cctgcgaggg cccggtaggg accgagcgtc tttgatttaa agctcagatt    240
tgcttttgtc gtgaaatatc aaagctgcct tgtttaaaga agccgtccca cgcgac        296

<210> SEQ ID NO 44
<211> LENGTH: 285
<212> TYPE: DNA
```

<210> SEQ ID NO 44
<211> LENGTH: 285
<212> TYPE: DNA
<213> ORGANISM: Maize streak virus

<400> SEQUENCE: 44

```
atccgacgac ggaggctcaa gctaggagaa ggcagggaag ggagctcgcg aaactctata    60
ctgataccte gcgccgatga aatccgccgc cgcccccttt tatagttgtt ctattatggg   120
ccggaccggg ccggcccagc aggtaaagag gcgcgcaata atattactgc gcctctttac   180
ctgcgagggc ccggtaggga ccgagcgtct ttgatttaaa gcttggatct gctttgtcgt   240
attttttcaa agctgccatg tttaaagaat ccgtccacat ccgac                   285
```

<210> SEQ ID NO 45
<211> LENGTH: 282
<212> TYPE: DNA
<213> ORGANISM: Maize streak virus

<400> SEQUENCE: 45

```
atatcggacg actccgagca gcttgcggga tggcaggatg ggagctccaa actctatatc    60
aaccggtttg cgccttcgaa atccgccgct ccccctttta tagtggttgt ttttgggccg   120
gaccgggccg gcccagcagg aaaagaaggc gcgcaataat attaccgcgc cttctttttc   180
tgcgagggcc cgtagggacc gagcgatttg atttaaagtt cggttctgct ttgtctgatt   240
tatctaaagc agcccaatct aaagaaaccg gtcccctgcg ac                      282
```

<210> SEQ ID NO 46
<211> LENGTH: 289
<212> TYPE: DNA
<213> ORGANISM: Maize streak virus

<400> SEQUENCE: 46

```
atccgacgac ggaggctagt gctagctcaa ggcagaaacg ggagctccca aactctatgt    60
aaccggtgcg ccttcgaaat ccgccgcccc tatttataga cgatttagct gggccggaac   120
gggccaggcc gggccggccc agcagggaaa gaaggcgcgc actaatatta ccgcgccttc   180
ttttcctgcg agggcccgca gggaccgagc gtctttgatt taaaggtttg atctgctttg   240
gtggttttt ccaaagctgc cgtgtttaaa gaaaccggtc ccgtctcac                289
```

<210> SEQ ID NO 47
<211> LENGTH: 277
<212> TYPE: DNA
<213> ORGANISM: Maize streak virus

<400> SEQUENCE: 47

```
ggacgactct gagcagcttg cgggatggca ggatgggagc tcccaaaact ctatgtaacc    60
ggtgcgcctt cgaaatccgc cgctcccctc tttatagtgg ttgtatttgg gccggaccgg   120
gccggcccag cagaaaaaga aggcgcgcaa taatattacc gcgccttctt ttctgcgagg   180
gcccggtagg gaccgagcgt ttttgatttt aagcgtggat ctgctttgtt tgattttgct   240
aaagcagcca tctttgagaa atccggtccc ctgcgac                            277
```

<210> SEQ ID NO 48
<211> LENGTH: 274
<212> TYPE: DNA
<213> ORGANISM: Milk Vetch Dwarf Virus

<400> SEQUENCE: 48

```
ctggggcggg gcttagtatt accccgccc caggatcagc ggagtcatca cgtgacccgc    60
acatgcctaa tgaatacaat gtatataacc aagtggacat ggtccccacc attatatttg   120
```
aattaaatgc actgaatata tgccttgctt cgtctcgaag caaagtaagg aataaatcgg      180
acccatatga gctgtatccc atgtgcatcg ctttatttgt atggtggaca ttacatagct      240
tttaagcggc gtacatgtta cgcttattct ttgt                                 274

<210> SEQ ID NO 49
<211> LENGTH: 493
<212> TYPE: DNA
<213> ORGANISM: Artificial sequence
<220> FEATURE:
<223> OTHER INFORMATION: Viral double enhancer

<400> SEQUENCE: 49
acttttcaac aaagggtatt atccggaaac ctcctcggat tccattgccc agctatctgt       60
cactttattg tgaagatagt ggaaaaggaa ggtggctcct acaaatgcca tcattgcgat      120
aaaggaaagg ctatcgttga agatgcctct gccgacagtg gtcccaaaga tggaccccca      180
cccacgagga gcatcgtgga aaagaagac gttccaacca cgtcttcaaa gcaagtggat      240
tgatgtgata tctccactga cgtaagggtt gacgaacaat cccactatcc ttcctcgaga      300
gctgcttgtg gggaccagac aaaaaaggaa tggtgcagaa ttgttaggcg cacctaccaa      360
aagcaacttt gcctttattg caaagataaa gcagattcct ctagtacaag tggggaacaa      420
aataacgtgg aaaagagctg tcctgacagc ccactcacta ttgcgtttga cgaacgcagt      480
gacgaccaca aaa                                                        493

<210> SEQ ID NO 50
<211> LENGTH: 1399
<212> TYPE: DNA
<213> ORGANISM: Artificial sequence
<220> FEATURE:
<223> OTHER INFORMATION: Plant-viral combination double enhancer

<400> SEQUENCE: 50
catgtgtgtt gtgcgagacc agccacgccg atacagttac tgtgctcacg ataaaattga       60
aaaggacaac cccattgttc cagtcattta gtcatggaag aaatgatcct ttccaaccca      120
atctcctagc cttttttctt cgaaagaaag gaagatctgc ccgttttat ctattcccgc       180 ccgcaacaag atcgatgatt acccaccagt aaaattccga aagcctaca cctaccacaa       240 acttcctctt tttttttttg gttgttgttg tttgagaaaa aagaagtcc ataaagcaag       300 attcccgtag gtgggcactg gcatgcgat gcaaggacag gtccatcagt ccatccgtca       360
gtcagggaat agcagctgcg gtgcaggagc acgcacaccc agctccctcc ctcccttgtt      420
cccaatcatt tgctcgctct acgtgctcct gctcttcacc gtcggaggga acgggtcttg      480
tctgacggta cagtcctcag caaggattac cggtaaacac ggcatcgttt atctgtaaac      540
ttaaactagc actggattta acaagcgcac aagctagtgg acactgaaca ggcccccccgg      600 ccgtgccata caatcaggtg gtaataatgc agcaattatg cggctgctta cccctggggc      660 tgggggggtgg gaagccaata atgttacctc gctgacagaa aaacgcatag ggaggaattc      720
ctttccggat tcccttgggt ccacaatcaa tcccccttgct tttccctcgc cggtgcctga      780
gtgactctga tgagctcttt ggcaaatgga tgacctgtgt ggaactctga tgagctcttt      840
ggcaaatgga tgacctgtgt ggcttggcca aatggtgagt gagtggagcg gagcagctgc      900
cgctcactca gctcctcctc gactcgcccc gggcatcatt cacgaatctg cttttcccccc      960 agccccggaa atacgtttaa aggaggccgt tttcagggac gagatgaggt tgattaaagc     1020

| | | |
|---|---|---|
| aaagcagagc agagcagagc taagctttct tgattccttc ccagaatgtc gctcgagctt | 1080 | |
| taggcaggca ggtgactgaa aactcgagac caggccacac caagggctat gtcgccagta | 1140 | |
| gccgcagaag atgtgctaga tctccaagac gtaagcaatg acgattgagg aggcattgac | 1200 | |
| gtcagggatg accgcagcgg agagtactgg gcccattcag tggatgctcc actgagttgt | 1260 | |
| attattgtgt gcttttcgga caagtgtgct gtccactttc ttttggcacc tgtgccactt | 1320 | |
| tattccttgt ctgccacgat gcctttgctt agcttgtaag caaggatcgc agtgcgtgtg | 1380 | |
| tgacaccacc ccccttccg | 1399 | |

<210> SEQ ID NO 51
<211> LENGTH: 514
<212> TYPE: DNA
<213> ORGANISM: Artificial sequence
<220> FEATURE:
<223> OTHER INFORMATION: Viral double enhancer

<400> SEQUENCE: 51

| | | |
|---|---|---|
| aaaattatcc attccagaag gtaattatcc aagatgtagc atcaagaatc caatgtttac | 60 | |
| gggaaaaact atggaagtat tatgttagct cagcaagaag cagatcaata tgcggcacat | 120 | |
| atgcaaccta tgttcaaaaa tgaagaatgt acagatacaa gatcctatac tgccagaata | 180 | |
| cgaagaagaa tacgtagaaa ttgaaaaaga agaaccaggc gaagaaaaga atcttgaaga | 240 | |
| cgtaagcact gacgacaaca atgaaaagaa gaagataagg tcggtgattg tgaaagagac | 300 | |
| atagaggaca catgtaaggt ggaaaatgta agggcggaaa gtaaccttat cacaaaggaa | 360 | |
| tcttatcccc cactacttat cctttttatat ttttccgtgt cattttttgcc cttgagctcg | 420 | |
| agtcaagagc ggagaattaa gggagtcacg ttttgacccc cgccgatgac gcgggacaag | 480 | |
| ccgttttacg tttggaactg acagaaccgc aacg | 514 | |

<210> SEQ ID NO 52
<211> LENGTH: 713
<212> TYPE: DNA
<213> ORGANISM: Artificial sequence
<220> FEATURE:
<223> OTHER INFORMATION: Viral double enhancer

<400> SEQUENCE: 52

| | | |
|---|---|---|
| aaaattatcc attccagaag gtaattatcc aagatgtagc atcaagaatc caatgtttac | 60 | |
| gggaaaaact atggaagtat tatgttagct cagcaagaag cagatcaata tgcggcacat | 120 | |
| atgcaaccta tgttcaaaaa tgaagaatgt acagatacaa gatcctatac tgccagaata | 180 | |
| cgaagaagaa tacgtagaaa ttgaaaaaga agaaccaggc gaagaaaaga atcttgaaga | 240 | |
| cgtaagcact gacgacaaca atgaaaagaa gaagataagg tcggtgattg tgaaagagac | 300 | |
| atagaggaca catgtaaggt ggaaaatgta agggcggaaa gtaaccttat cacaaaggaa | 360 | |
| tcttatcccc cactacttat cctttttatat ttttccgtgt cattttttgcc cttgagctcg | 420 | |
| agaccaggcc acaccaaggg ctatgtcgcc agtagccgca gaagatgtgc tagatctcca | 480 | |
| agacgtaagc aatgacgatt gaggaggcat tgacgtcagg gatgaccgca gcggagagta | 540 | |
| ctgggcccat tcagtggatg ctccactgag ttgtattatt gtgtgctttt cggacaagtg | 600 | |
| tgctgtccac tttcttttgg cacctgtgcc actttattcc ttgtctgcca cgatgccttt | 660 | |
| gcttagcttg taagcaagga tcgcagtgcg tgtgtgacac caccccccctt ccg | 713 | |

<210> SEQ ID NO 53
<211> LENGTH: 803

```
<212> TYPE: DNA
<213> ORGANISM: Artificial sequence
<220> FEATURE:
<223> OTHER INFORMATION: Viral double enhancer

<400> SEQUENCE: 53
aaaattatcc attccagaag gtaattatcc aagatgtagc atcaagaatc caatgtttac      60
gggaaaaact atggaagtat tatgttagct cagcaagaag cagatcaata tgcggcacat     120
atgcaaccta tgttcaaaaa tgaagaatgt acagatacaa gatcctatac tgccagaata     180
cgaagaagaa tacgtagaaa ttgaaaaaga agaaccaggc gaagaaaaga atcttgaaga     240
cgtaagcact gacgacaaca atgaaaagaa gaagataagg tcggtgattg tgaaagagac     300
atagaggaca catgtaaggt ggaaaatgta agggcggaaa gtaaccttat cacaaaggaa     360
tcttatcccc cactacttat cctttatat ttttccgtgt cattttgcc cttgagctcg       420
agggattaat ggattgatca acatccttac cgctatgggt aagattgatg aaaagtcaaa     480
aacaaaaatc aattatgcac accagcatgt gttgatcacc agctattgtg ggacaccaat     540
ttcgtccaca gacatcaaca tcttatcgtc ctttgaagat aagataataa tgttgaagat     600
aagagtggga gccaccacta aaacattgct ttgtcaaaag ctaaaaaaga tgatgcccga     660
cagccacttg tgtgaagcat gtgaagccgg tccctccact aagaaaatta gtgaagcatc     720
ttccagtggt ccctccactc acagctcaat cagtgagcaa caggacgaag gaaatgacgt     780
aagccatgac gtctaatccc aca                                             803
```

```
<210> SEQ ID NO 54
<211> LENGTH: 499
<212> TYPE: DNA
<213> ORGANISM: Artificial sequence
<220> FEATURE:
<223> OTHER INFORMATION: Viral-bacterial combination double enhancer

<400> SEQUENCE: 54
caacggagtg gtcgtacata ctacaaatgg attgccaata gtattcgcaa tggatacaca      60
ccgaggttgt tgcgagaaat tttgtatcac ggtacaatta ccaggggcc ttacgcgata     120
tgattttatt ggcgccacga ttacgaaggt aagatttggt aaagaaaaac gcaaatgcga     180
tattaatttt tcggaattaa ttatagaaac ttcggtagga aatatcgttt tactggcaga     240
aaacattcat aatggatatt actctcatga tgtattcgct tgttttgaag gtaaagttga     300
aacttttcgt ttgtaaatac aaaaaatgta tatgagtatt tgttgtcgga atgtcatatc     360
aacaatgttg tgtatatatg tgtaaactaa aatacactat actcgagtca agagcggaga     420
attaagggag tcacgttttg accccgccg atgacgcggg acaagccgtt ttacgtttgg      480
aactgacaga accgcaacg                                                   499
```

```
<210> SEQ ID NO 55
<211> LENGTH: 823
<212> TYPE: DNA
<213> ORGANISM: Artificial sequence
<220> FEATURE:
<223> OTHER INFORMATION: Viral double enhancer

<400> SEQUENCE: 55
caacggagtg gtcgtacata ctacaaatgg attgccaata gtattcgcaa tggatacaca      60
ccgaggttgt tgcgagaaat tttgtatcac ggtacaatta ccaggggcc ttacgcgata     120
tgattttatt ggcgccacga ttacgaaggt aagatttggt aaagaaaaac gcaaatgcga     180
```

| | |
|---|---|
| tattaattttt tcggaattaa ttatagaaac ttcggtagga aatatcgttt tactggcaga | 240 |
| aaacattcat aatggatatt actctcatga tgtattcgct tgttttgaag gtaaagttga | 300 |
| aacttttcgt ttgtaaatac aaaaaatgta tatgagtatt tgttgtcgga atgtcatatc | 360 |
| aacaatgttg tgtatatatg tgtaaactaa aatacactat actcgagaaa attatccatt | 420 |
| ccagaaggta attatccaag atgtagcatc aagaatccaa tgtttacggg aaaaactatg | 480 |
| gaagtattat gttagctcag caagaagcag atcaatatgc ggcacatatg caacctatgt | 540 |
| tcaaaaatga agaatgtaca gatacaagat cctatactgc cagaatacga agaagaatac | 600 |
| gtagaaattg aaaagaaga accaggcgaa gaaaagaatc ttgaagacgt aagcactgac | 660 |
| gacaacaatg aaaagaagaa gataaggtcg gtgattgtga agagacata gaggacacat | 720 |
| gtaaggtgga aaatgtaagg gcggaaagta accttatcac aaaggaatct tatcccccac | 780 |
| tacttatcct tttatatttt tccgtgtcat ttttgccctt gag | 823 |

<210> SEQ ID NO 56
<211> LENGTH: 479
<212> TYPE: DNA
<213> ORGANISM: Artificial sequence
<220> FEATURE:
<223> OTHER INFORMATION: Viral bacterial combination double enhancer

<400> SEQUENCE: 56

| | |
|---|---|
| ggattaatgg attgatcaac atccttaccg ctatgggtaa gattgatgaa aagtcaaaaa | 60 |
| caaaaatcaa ttatgcacac cagcatgtgt tgatcaccag ctattgtggg acaccaattt | 120 |
| cgtccacaga catcaacatc ttatcgtcct ttgaagataa gataataatg ttgaagataa | 180 |
| gagtgggagc caccactaaa acattgcttt gtcaaaagct aaaaaagatg atgcccgaca | 240 |
| gccacttgtg tgaagcatgt gaagccggtc cctccactaa gaaaattagt gaagcatctt | 300 |
| ccagtggtcc ctccactcac agctcaatca gtgagcaaca ggacgaagga aatgacgtaa | 360 |
| gccatgacgt ctaatcccac actcgagtca agagcggaga attaagggag tcacgttttg | 420 |
| accccccgccg atgacgcggg acaagccgtt ttacgtttgg aactgacaga accgcaacg | 479 |

<210> SEQ ID NO 57
<211> LENGTH: 678
<212> TYPE: DNA
<213> ORGANISM: Artificial sequence
<220> FEATURE:
<223> OTHER INFORMATION: Viral double enhancer

<400> SEQUENCE: 57

| | |
|---|---|
| ggattaatgg attgatcaac atccttaccg ctatgggtaa gattgatgaa aagtcaaaaa | 60 |
| caaaaatcaa ttatgcacac cagcatgtgt tgatcaccag ctattgtggg acaccaattt | 120 |
| cgtccacaga catcaacatc ttatcgtcct ttgaagataa gataataatg ttgaagataa | 180 |
| gagtgggagc caccactaaa acattgcttt gtcaaaagct aaaaaagatg atgcccgaca | 240 |
| gccacttgtg tgaagcatgt gaagccggtc cctccactaa gaaaattagt gaagcatctt | 300 |
| ccagtggtcc ctccactcac agctcaatca gtgagcaaca ggacgaagga aatgacgtaa | 360 |
| gccatgacgt ctaatcccac actcgagacc aggccacacc aagggctatg tcgccagtag | 420 |
| ccgcagaaga tgtgctagat ctccaagacg taagcaatga cgattgagga ggcattgacg | 480 |
| tcagggatga ccgcagcgga gagtactggg cccattcagt ggatgctcca ctgagttgta | 540 |
| ttattgtgtg cttttcggac aagtgtgctg tccacttttct tttggcacct gtgccactt | 600 |
| attccttgtc tgccacgatg cctttgctta gcttgtaagc aaggatcgca gtgcgtgtgt | 660 |

```
gacaccaccc cccttccg                                               678

<210> SEQ ID NO 58
<211> LENGTH: 803
<212> TYPE: DNA
<213> ORGANISM: Artificial sequence
<220> FEATURE:
<223> OTHER INFORMATION: Viral double enhancer

<400> SEQUENCE: 58
ggattaatgg attgatcaac atccttaccg ctatgggtaa gattgatgaa aagtcaaaaa    60
caaaaatcaa ttatgcacac cagcatgtgt tgatcaccag ctattgtggg acaccaattt   120
cgtccacaga catcaacatc ttatcgtcct ttgaagataa gataataatg ttgaagataa   180
gagtgggagc caccactaaa acattgcttt gtcaaaagct aaaaaagatg atgcccgaca   240
gccacttgtg tgaagcatgt gaagccggtc cctccactaa gaaaattagt gaagcatctt   300
ccagtggtcc ctccactcac agctcaatca gtgagcaaca ggacgaagga aatgacgtaa   360
gccatgacgt ctaatcccac actcgagaaa attatccatt ccagaaggta attatccaag   420
atgtagcatc aagaatccaa tgtttacggg aaaaactatg gaagtattat gttagctcag   480
caagaagcag atcaatatgc ggcacatatg caacctatgt tcaaaaatga gaatgtaca    540 gatacaagat cctatactgc cagaatacga agaagaatac gtagaaattg aaaaagaaga   600
accaggcgaa gaaaagaatc ttgaagacgt aagcactgac gacaacaatg aaaagaagaa   660
gataaggtcg gtgattgtga agagacata gaggacacat gtaaggtgga aaatgtaagg   720
gcggaaagta accttatcac aaaggaatct tatcccccac tacttatcct tttatatttt   780
tccgtgtcat ttttgccctt gag                                           803

<210> SEQ ID NO 59
<211> LENGTH: 876
<212> TYPE: DNA
<213> ORGANISM: Artificial sequence
<220> FEATURE:
<223> OTHER INFORMATION: Viral double enhancer

<400> SEQUENCE: 59
aagccatcga aaccggtcca ctggtaaacc ttcaagatga agaaagaaag attctttgcc    60
aaaaaatgca aaagtacaaa gggcacagct gtcagttgtg caaatccgag tcatctggac   120
cacaaacatc agaagagggt ctacaagagt cagaagacga agacttttcg gtgctagttt   180
aattactggc agacaaagtg gcagacatac tgtcccacaa atgaagatgg aatctgtaaa   240
agaaaacgcg tgaaataatg cgtctgacaa aggttaggtc ggctgccttt aatcaatacc   300
aaagtggtcc ctaccacgat ggaaaaactg tgcagtcggt ttggcttttt ctgacgaaca   360
aataagattc gtggccgaca ggtgggggtc caccatgtga aggcatcttc agactccaat   420
aatggagcaa tgacgtaagg gcttacgaaa taagtaaggg tagtttggga aatgtccact   480
cacccgtcag tctataaatc tcgagatcat ctggagccaa caagctagga agccgtctga   540
gcaagatatt cagatcctta cagagttttt acttcggaca gtcaaaaatg agtttaactt   600
ctcagccgag gtaaaacaag aaatatgctt acgtctacag agggatttct ctgaagatca   660
tgtttgccag ctatgcgaac aatcatcggg agatcttgag ccaatcaaag aggagtgatg   720
tagacctaaa gcaataatgg agccatgacg taagggctta cgccattacg aaataattaa   780
aggctgatgt gacctgtcgg tctctcagaa cctttacttt ttatatttgg cgtgtatttt   840
```

<210> SEQ ID NO 60
<211> LENGTH: 796
<212> TYPE: DNA
<213> ORGANISM: Artificial sequence
<220> FEATURE:
<223> OTHER INFORMATION: Viral double enhancer

<400> SEQUENCE: 60

```
aagccatcga aaccggtcca ctggtaaacc ttcaagatga agaaagaaag attctttgcc     60
aaaaaatgca aaagtacaaa gggcacagct gtcagttgtg caaatccgag tcatctggac    120
cacaaacatc agaagagggt ctacaagagt cagaagacga agacttttcg gtgctagttt    180
aattactggc agacaaagtg gcagacatac tgtcccacaa atgaagatgg aatctgtaaa    240
agaaaacgcg tgaaataatg cgtctgacaa aggttaggtc ggctgccttt aatcaatacc    300
aaagtggtcc ctaccacgat ggaaaaactg tgcagtcggt ttggcttttt ctgacgaaca    360
aataagattc gtggccgaca ggtgggggtc caccatgtga aggcatcttc agactccaat    420
aatggagcaa tgacgtaagg gcttacgaaa taagtaaggg tagtttggga aatgtccact    480
cacccgtcag tctataaatc tcgagaccag gccacaccaa gggctatgtc gccagtagcc    540
gcagaagatg tgctagatct ccaagacgta agcaatgacg attgaggagg cattgacgtc    600
agggatgacc gcagcggaga gtactgggcc cattcagtgg atgctccact gagttgtatt    660
attgtgtgct tttcggacaa gtgtgctgtc cactttcttt tggcacctgt gccactttat    720
tccttgtctg ccacgatgcc tttgcttagc ttgtaagcaa ggatcgcagt gcgtgtgtga    780
caccacccc cttccg                                                     796
```

<210> SEQ ID NO 61
<211> LENGTH: 906
<212> TYPE: DNA
<213> ORGANISM: Artificial sequence
<220> FEATURE:
<223> OTHER INFORMATION: Viral double enhancer

<400> SEQUENCE: 61

```
aagccatcga aaccggtcca ctggtaaacc ttcaagatga agaaagaaag attctttgcc     60
aaaaaatgca aaagtacaaa gggcacagct gtcagttgtg caaatccgag tcatctggac    120
cacaaacatc agaagagggt ctacaagagt cagaagacga agacttttcg gtgctagttt    180
aattactggc agacaaagtg gcagacatac tgtcccacaa atgaagatgg aatctgtaaa    240
agaaaacgcg tgaaataatg cgtctgacaa aggttaggtc ggctgccttt aatcaatacc    300
aaagtggtcc ctaccacgat ggaaaaactg tgcagtcggt ttggcttttt ctgacgaaca    360
aataagattc gtggccgaca ggtgggggtc caccatgtga aggcatcttc agactccaat    420
aatggagcaa tgacgtaagg gcttacgaaa taagtaaggg tagtttggga aatgtccact    480
cacccgtcag tctataaatc tcgagcaacg gagtggtcgt acatactaca aatggattgc    540
caatagtatt cgcaatggat acacaccgag gttgttgcga gaattttgt atcacggtac    600
aattccaggg ggccttacg cgatatgatt ttattggcgc cacgattacg aaggtaagat    660
ttggtaaaga aaaacgcaaa tgcgatatta attttcgga attaattata gaaacttcgg    720
taggaaatat cgttttactg gcagaaaaca ttcataatgg atattactct catgatgtat    780
tcgcttgttt tgaaggtaaa gttgaaactt tcgtttgta aatacaaaaa atgtatatga    840
gtatttgttg tcggaatgtc atatcaacaa tgttgtgtat atatgtgtaa actaaaatac    900
```

<210> SEQ ID NO 62
<211> LENGTH: 668
<212> TYPE: DNA
<213> ORGANISM: Artificial sequence
<220> FEATURE:
<223> OTHER INFORMATION: Viral double enhancer

<400> SEQUENCE: 62

```
atcatctgga gccaacaagc taggaagccg tctgagcaag atattcagat ccttacagag    60
tttttacttc ggacagtcaa aaatgagttt aacttctcag ccgaggtaaa acaagaaata   120
tgcttacgtc tacagaggga tttctctgaa gatcatgttt gccagctatg cgaacaatca   180
tcgggagatc ttgagccaat caaagaggag tgatgtagac ctaaagcaat aatggagcca   240
tgacgtaagg gcttacgcca ttacgaaata attaaaggct gatgtgacct gtcggtctct   300
cagaaccttt acttttata tttggcgtgt atttttaaat ttccacggca atgacgatgt   360
gacctgtgca tctcgagacc aggccacacc aagggctatg tcgccagtag ccgcagaaga   420
tgtgctagat ctccaagacg taagcaatga cgattgagga ggcattgacg tcagggatga   480
ccgcagcgga gagtactggg cccattcagt ggatgctcca ctgagttgta ttattgtgtg   540
cttttcggac aagtgtgctg tccactttct tttggcacct gtgccacttt attccttgtc   600
tgccacgatg cctttgctta gcttgtaagc aaggatcgca gtgcgtgtgt gacaccaccc   660
cccttccg                                                            668
```

<210> SEQ ID NO 63
<211> LENGTH: 793
<212> TYPE: DNA
<213> ORGANISM: Artificial sequence
<220> FEATURE:
<223> OTHER INFORMATION: Viral double enhancer

<400> SEQUENCE: 63

```
atcatctgga gccaacaagc taggaagccg tctgagcaag atattcagat ccttacagag    60
tttttacttc ggacagtcaa aaatgagttt aacttctcag ccgaggtaaa acaagaaata   120
tgcttacgtc tacagaggga tttctctgaa gatcatgttt gccagctatg cgaacaatca   180
tcgggagatc ttgagccaat caaagaggag tgatgtagac ctaaagcaat aatggagcca   240
tgacgtaagg gcttacgcca ttacgaaata attaaaggct gatgtgacct gtcggtctct   300
cagaaccttt acttttata tttggcgtgt atttttaaat ttccacggca atgacgatgt   360
gacctgtgca tctcgagaaa attatccatt ccagaaggta attatccaag atgtagcatc   420
aagaatccaa tgtttacggg aaaaactatg gaagtattat gttagctcag caagaagcag   480
atcaatatgc ggcacatatg caacctatgt tcaaaaatga agaatgtaca gatacaagat   540
cctatactgc cagaatacga agaagaatac gtagaaattg aaaagaaga accaggcgaa   600
gaaaagaatc ttgaagacgt aagcactgac gacaacaatg aaaagaagaa gataaggtcg   660
gtgattgtga agagacata gaggacacat gtaaggtgga aaatgtaagg gcggaaagta   720
accttatcac aaaggaatct tatcccccac tacttatcct tttatatttt tccgtgtcat   780
ttttgccctt gag                                                      793
```

<210> SEQ ID NO 64
<211> LENGTH: 778
<212> TYPE: DNA

<213> ORGANISM: Artificial sequence
<220> FEATURE:
<223> OTHER INFORMATION: Viral double enhancer

<400> SEQUENCE: 64

```
atcatctgga gccaacaagc taggaagccg tctgagcaag atattcagat ccttacagag        60
tttttacttc ggacagtcaa aaatgagttt aacttctcag ccgaggtaaa acaagaaata       120
tgcttacgtc tacagaggga tttctctgaa gatcatgttt gccagctatg cgaacaatca       180
tcgggagatc ttgagccaat caagaggag tgatgtagac ctaaagcaat aatggagcca        240
tgacgtaagg gcttacgcca ttacgaaata attaaaggct gatgtgacct gtcggtctct       300
cagaaccttt acttttata tttggcgtgt atttttaaat ttccacggca atgacgatgt        360
gacctgtgca tctcgagcaa cggagtggtc gtacatacta caaatggatt gccaatagta       420
ttcgcaatgg atacacaccg aggttgttgc gagaaatttt gtatcacggt acaattacca       480
ggggccctta cgcgatatga ttttattggc gccacgatta cgaaggtaag atttggtaaa       540
gaaaaacgca aatgcgatat taattttcg gaattaatta tagaaacttc ggtaggaaat       600
atcgttttac tggcagaaaa cattcataat ggatattact ctcatgatgt attcgcttgt      660
tttgaaggta agttgaaac ttttcgtttg taaatacaaa aatgtatat gagtatttgt        720
tgtcggaatg tcatatcaac aatgttgtgt atatatgtgt aaactaaaat acactata       778
```

<210> SEQ ID NO 65
<211> LENGTH: 728
<212> TYPE: DNA
<213> ORGANISM: Artificial sequence
<220> FEATURE:
<223> OTHER INFORMATION: Viral double enhancer

<400> SEQUENCE: 65

```
gagcgcttga cggtgttgaa ttaatttgca ggtatagttc aggaagcttc aaacaagcag        60
aaaagaatta tcacagcaat gataaagaat tactagcagt caagcaagta atcaccaagt       120
tttcagctta cctaacacca gtcaggttta cagtaagaac tgataacaaa aattttactt       180
atttccttag aattaatctt aaaggtgata gtaaacaagg acgattagtc cgttggcaaa       240
attggttcag caagtatcaa tttgatgtcg aacatcttga aggtgtaaaa aacgttttag       300
cagattgcct cacgagagat tttaatgctt aaaaacgtaa gcgctgacgt actcgagatc       360
atctggagcc aacaagctag gaagccgtct gagcaagata ttcagatcct tacagagttt       420
ttacttcgga cagtcaaaaa tgagtttaac ttctcagccg aggtaaaaca agaaatatgc       480
ttacgtctac agagggatt ctctgaagat catgtttgcc agctatgcga acaatcatcg        540
ggagatcttg agccaatcaa agaggagtga tgtagaccta aagcaataat ggagccatga      600
cgtaagggct tacgccatta cgaaataatt aaaggctgat gtgacctgtc ggtctctcag      660
aacctttact ttttatattt ggcgtgtatt tttaaatttc cacggcaatg acgatgtgac      720
ctgtgcat                                                                 728
```

<210> SEQ ID NO 66
<211> LENGTH: 1603
<212> TYPE: DNA
<213> ORGANISM: Artificial sequence
<220> FEATURE:
<223> OTHER INFORMATION: Plant viral combination double enhancer

<400> SEQUENCE: 66

```
cggtgaggga ttgacgcata acagaaataa ctagtacctt tctataaggc aaaattgagc        60
```

| | |
|---|---|
| acagtgattc actgattgtg tcccctagct tctctttccc cacctacagg ttgcaacgca | 120 |
| aaagcaagca ggaaaaaaag aaacacattt agcagtctag actctaacat catccaacga | 180 |
| ttcatggcct gttggcatgt tgctggaccg tcactggttc acaggccttt agaggatact | 240 |
| tggccagagc gggcgcgcgt gcgcggcggc ggagtgctgt ggtatccagt gcgtgtgcgc | 300 |
| cgatgtggag gccaacgcag cgggcctggg ctttgaggcc gggatgggga gcctcaggga | 360 |
| gtgcggcgac ggctgcgcat ctgcgccgtc atgtgggaac cgacggactc agcgcggcgt | 420 |
| cgctgtgcgg ctgtgcgtct tgcgccacct gcacaaggtg gtttgtgtgc gagtacgccg | 480 |
| gtaaagcagg gcatatgcct ctctctctgg attctttgcg cttgcatact aattgttggt | 540 |
| ttgcattttg agctgaacca atctattaaa atcgctggac gactattaaa atcgctggac | 600 |
| gacgtagttc tgtacttctg ttccatgacg gacgaaatga ttccggatga agctgtgcgc | 660 |
| ccgtgctgca ttccaaactg caaaaattgc tgattgctgg acgcggctcc gtccgacggc | 720 |
| gtacaaactg attctatatg gaccgatgag gcgatccaaa cagactacta aactcctact | 780 |
| taccaagcaa acaattgat caatgattac ccgagtgcca acgggcact atgaacacag | 840 |
| aacccataac ataataagct aaactgtact aatgcacaag atgcattaaa aaatgccgtt | 900 |
| ttagtagatt gttaaccatg tttgtgctct ccacatgtca tagatatatt cttataattt | 960 |
| gttcacctgt gtttccggtt agttgttcat ctatgcctag ctttgctttg gttctgttct | 1020 |
| tgtcatagct gaaaaagaa gcgaattcat tgggcaaagc cttatatata gttgatacat | 1080 |
| aaggattcat gtaaaataca tttgcagtcc ggtacagttt ttactttta gccttgtgcc | 1140 |
| ctttgcaaaa aggactacaa gaatcatgcc ttttttcagc gctcgagaaa attatccatt | 1200 |
| ccagaaggta attatccaag atgtagcatc aagaatccaa tgtttacggg aaaaactatg | 1260 |
| gaagtattat gttagctcag caagaagcag atcaatatgc ggcacatatg caacctatgt | 1320 |
| tcaaaaatga agaatgtaca gatacaagat cctatactgc cagaatacga agaagaatac | 1380 |
| gtagaaattg aaaagaaga accaggcgaa gaaaagaatc ttgaagacgt aagcactgac | 1440 |
| gacaacaatg aaaagaagaa gataaggtcg gtgattgtga agagacata gaggacacat | 1500 |
| gtaaggtgga aaatgtaagg gcggaaagta accttatcac aaaggaatct tatccccac | 1560 |
| tacttatcct tttatatttt tccgtgtcat ttttgccctt gag | 1603 |

<210> SEQ ID NO 67
<211> LENGTH: 1603
<212> TYPE: DNA
<213> ORGANISM: Artificial sequence
<220> FEATURE:
<223> OTHER INFORMATION: Plant viral combination double enhancer

<400> SEQUENCE: 67

| | |
|---|---|
| aaaattatcc attccagaag gtaattatcc aagatgtagc atcaagaatc caatgtttac | 60 |
| gggaaaaact atggaagtat tatgttagct cagcaagaag cagatcaata tgcggcacat | 120 |
| atgcaaccta tgttcaaaaa tgaagaatgt acagatacaa gatcctatac tgccagaata | 180 |
| cgaagaagaa tacgtagaaa ttgaaaaaga gaaccaggc gaagaaaaga atcttgaaga | 240 |
| cgtaagcact gacgacaaca atgaaaagaa gaagataagg tcggtgattg tgaaagagac | 300 |
| atagaggaca catgtaaggt ggaaaatgta agggcggaaa gtaaccttat cacaaaggaa | 360 |
| tcttatcccc cactacttat ccttttatat ttttccgtgt catttttgcc cttgagctcg | 420 |
| agcggtgagg gattgacgca taacagaaat aactagtacc tttctataag gcaaaattga | 480 |

```
gcacagtgat tcactgattg tgtcccctag cttctctttc cccacctaca ggttgcaacg    540
caaaagcaag caggaaaaaa agaaacacat ttagcagtct agactctaac atcatccaac    600
gattcatggc ctgttggcat gttgctggac cgtcactggt tcacaggcct ttagaggata    660
cttggccaga gcgggcgcgc gtgcgcggcg cggagtgctg tggtatcca  gtgcgtgtgc    720 gccgatgtgg aggccaacgc agcgggcctg ggctttgagg ccgggatggg gagcctcagg    780
gagtgcggcg acggctgcgc atctgcgccg tcatgtggga accgacggac tcagcgcggc    840
gtcgctgtgc ggctgtgcgt cttgcgccac ctgcacaagg tggtttgtgt gcgagtacgc    900
cggtaaagca gggcatatgc ctctctctct ggattctttg cgcttgcata ctaattgttg    960
gtttgcattt tgagctgaac caatctatta aaatcgctgg acgactatta aaatcgctgg   1020
acgacgtagt tctgtacttc tgttccatga cggacgaaat gattccggat gaagctgtgc   1080
gcccgtgctg cattccaaac tgcaaaaatt gctgattgct ggacgcggct ccgtccgacg   1140
gcgtacaaac tgattctata tggaccgatg aggcgatcca aacagactac taaactccta   1200
cttaccaagc aaaacaattg atcaatgatt acccgagtgc caaacgggca ctatgaacac   1260
agaacccata acataataag ctaaactgta ctaatgcaca agatgcatta aaaaatgccg   1320
ttttagtaga ttgttaacca tgtttgtgct ctccacatgt catagatata ttcttataat   1380
ttgttcacct gtgtttccgg ttagttgttc atctatgcct agctttgctt tggttctgtt   1440
cttgtcatag ctgaaaaaag aagcgaattc attgggcaaa gccttatata tagttgatac   1500
ataaggattc atgtaaaata catttgcagt ccggtacagt ttttactttt tagccttgtg   1560 cccctttgcaa aaaggactac aagaatcatg ccttttttca gcg                    1603

<210> SEQ ID NO 68
<211> LENGTH: 1568
<212> TYPE: DNA
<213> ORGANISM: Artificial sequence
<220> FEATURE:
<223> OTHER INFORMATION: Plant viral combination double enhancer

<400> SEQUENCE: 68
cggtgaggga ttgacgcata acagaaataa ctagtaccTT tctataaggc aaaattgagc     60
acagtgattc actgattgtg tcccctagct tctctttccc cacctacagg ttgcaacgca    120
aaagcaagca ggaaaaaag aaacacattt agcagtctag actctaacat catccaacga    180
ttcatggcct gttggcatgt tgctggaccg tcactggttc acaggccttt agaggatact    240
tggccagagc gggcgcgcgt gcgcggcggc ggagtgctgt ggtatccagt gcgtgtgcgc    300
cgatgtggag gccaacgcag cgggcctggg ctttgaggcc gggatgggga gcctcaggga    360
gtgcggcgac ggctgcgcat ctgcgccgtc atgtgggaac cgacggactc agcgcggcgt    420
cgctgtgcgg ctgtgcgtct tgcgccacct gcacaaggtg tttgtgtgc  gagtacgccg    480 gtaaagcagg gcatatgcct ctctctctgg attctttgcg cttgcatact aattgttggt    540
ttgcattttg agctgaacca atctattaaa atcgctggac gactattaaa atcgctggac    600
gacgtagttc tgtacttctg ttccatgacg gacgaaatga ttccggatga agctgtgcgc    660
ccgtgctgca ttccaaactg caaaaattgc tgattgctgg acgcggctcc gtccgacggc    720
gtacaaactg attctatatg gaccgatgag gcgatccaaa cagactacta aactcctact    780
taccaagcaa acaattgat caatgattac ccgagtgcca acgggcact  atgaacacag    840 aacccataac ataataagct aaactgtact aatgcacaag atgcattaaa aaatgccgtt    900 tagtagatt gttaaccatg tttgtgctct ccacatgtca tagatatatt cttataattt    960
```

```
gttcacctgt gtttccggtt agttgttcat ctatgcctag ctttgctttg gttctgttct    1020
tgtcatagct gaaaaaagaa gcgaattcat tgggcaaagc cttatatata gttgatacat    1080
aaggattcat gtaaaataca tttgcagtcc ggtacagttt ttactttta gccttgtgcc     1140 ctttgcaaaa aggactacaa gaatcatgcc ttttttcagc gctcgaggga ttaatggatt    1200
gatcaacatc cttaccgcta tgggtaagat tgatgaaaag tcaaaacaa aaatcaatta    1260 tgcacaccag catgtgttga tcaccagcta ttgtgggaca ccaatttcgt ccacagacat    1320
caacatctta tcgtcctttg aagataagat aataatgttg aagataagag tgggagccac    1380
cactaaaaca ttgctttgtc aaaagctaaa aagatgatg cccgacagcc acttgtgtga     1440
agcatgtgaa gccggtccct ccactaagaa aattagtgaa gcatcttcca gtggtccctc    1500
cactcacagc tcaatcagtg agcaacagga cgaaggaaat gacgtaagcc atgacgtcta    1560
atcccaca                                                              1568
```

<210> SEQ ID NO 69
<211> LENGTH: 1302
<212> TYPE: DNA
<213> ORGANISM: Artificial sequence
<220> FEATURE:
<223> OTHER INFORMATION: Plant viral combination double enhancer

<400> SEQUENCE: 69

```
gttcaaagct tgcgtgcaga tactcccgta aaacacgcat ccgctcgtgt gcagttcaat      60
cacaagtttg tggatggttg gaacgcagtc acccgtcacc ccacggcccc acgtggccgt    120
gacacggtcg gttcaaagtc cacggtgtac cacttccacc cgtccccacc ccaccatcct    180
tctctacttc tctcctctct ctcccaacgg acccgatctc gtacctcact tccgtcccgc    240
ccagcttcgc ttcacggcgc gccgaccggc ttggacgcgc cgaccggctc gtgatcagct    300
cggtcggatc cgacggtcgc tcgctgctgc agcgggcgct tgctgtgcgt cgcgtgggct    360
cggccggagc ccggagggag gcggagcctt ccccgggtct cgaagatggc ggcgccgccg    420
gcgagggccc gggccgacta cgactacctc atcaagctgc tcctcatcgg cgatagcggt    480
gagtgccttc accatcacgc ctcctccccc tctcgctctc cgtccggatc gattggctgc    540
ggtgagatct gagtgcgaaa tcgaagttcg gttctgattc gtccggatcg actgtgaaac    600
gcggatgctg ctgggccctg ctcctcccaa aagctgccgc tgtttgcctg tttcgtcgat    660
gacgtgcaac ggttttatgt atataggaat gatatgctga aaactcaccc accatcgggt    720
gatgactact ttgctagttg atgcttgaga gctacattta caaccacaca gacaagtgaa    780
ccgaaattcc atttggaaac cgggatgcga caacggacgc taattacaaa ataaacagcc    840
tttgccgtct tatctaactg ttacattgga atggtgattg tcgtgctcca cagaaaagga    900
aatgcatgga ttttgctcga gggattaatg gattgatcaa catccttacc gctatgggta    960
agattgatga aaagtcaaaa acaaaaatca attatgcaca ccagcatgtg ttgatcacca   1020
gctattgtgg gacaccaatt tcgtccacag acatcaacat cttatcgtcc tttgaagata   1080
agataataat gttgaagata gagtgggag ccaccactaa acattgctt tgtcaaaagc     1140 taaaaagat gatgcccgac agccacttgt gtgaagcatg tgaagccggt ccctccacta    1200
agaaaattag tgaagcatct tccagtggtc cctccactca cagctcaatc agtgagcaac   1260
aggacgaagg aaatgacgta agccatgacg tctaatccca ca                      1302
```

<210> SEQ ID NO 70

<211> LENGTH: 1302
<212> TYPE: DNA
<213> ORGANISM: Artificial sequence
<220> FEATURE:
<223> OTHER INFORMATION: Plant viral combination double enhancer

<400> SEQUENCE: 70

```
ggattaatgg attgatcaac atccttaccg ctatgggtaa gattgatgaa aagtcaaaaa      60
caaaaatcaa ttatgcacac cagcatgtgt tgatcaccag ctattgtggg acaccaattt     120
cgtccacaga catcaacatc ttatcgtcct ttgaagataa gataataatg ttgaagataa     180
gagtgggagc caccactaaa acattgcttt gtcaaaagct aaaaaagatg atgcccgaca     240
gccacttgtg tgaagcatgt gaagccggtc cctccactaa gaaaattagt gaagcatctt     300
ccagtggtcc ctccactcac agctcaatca gtgagcaaca ggacgaagga atgacgtaa      360
gccatgacgt ctaatcccac actcgaggtt caaagcttgc gtgcagatac tcccgtaaaa     420
cacgcatccg ctcgtgtgca gttcaatcac aagtttgtgg atggttggaa cgcagtcacc     480
cgtcacccca cggccccacg tggccgtgac acggtcggtt caaagtccac ggtgtaccac     540
ttccacccgt ccccacccca ccatccttct ctacttctct cctctctctc ccaacggacc     600
cgatctcgta cctcacttcc gtcccgccca gcttcgcttc acggcgcgcc gaccggcttg     660
gacgcgccga ccggctcgtg atcagctcgg tcggatccga cggtcgctcg ctgctgcagc     720
gggcgcttgc tgtgcgtcgc gtgggctcgg ccggagcccg gagggaggcg gagccttccc     780
cgggtctcga agatggcggc gccgccggcg agggcccggg ccgactacga ctacctcatc     840
aagctgctcc tcatcggcga tagcggtgag tgccttcacc atcacgcctc ctcccctct      900
cgctctccgt ccggatcgat tggctgcggt gagatctgag tgcgaaatcg aagttcggtt     960
ctgattcgtc cggatcgact gtgaaacgcg gatgctgctg ggccctgctc ctcccaaaag    1020
ctgccgctgt ttgcctgttt cgtcgatgac gtgcaacggt tttatgtata taggaatgat    1080
atgctgaaaa ctcacccacc atcgggtgat gactactttg ctagttgatg cttgagagct    1140
acatttacaa ccacacagac aagtgaaccg aaattccatt tggaaaccgg gatgcgacaa    1200
cggacgctaa ttacaaaata aacagccttt gccgtcttat ctaactgtta cattggaatg    1260
gtgattgtcg gtgctcacag aaaaggaaat gcatggattt tg                       1302
```

<210> SEQ ID NO 71
<211> LENGTH: 781
<212> TYPE: DNA
<213> ORGANISM: Artificial sequence
<220> FEATURE:
<223> OTHER INFORMATION: Plant viral combination double enhancer

<400> SEQUENCE: 71

```
gaaatggctg ttaacaggca cgaaatgacc cgaatcgaag cctacagtca ccactcgact      60
gccaatcaca cgaccaccaa tcccttccct tgtccacggc ctgcacgaaa agttgtattc     120
attgtccacg gcccgtaggc gaaggcgagg cccatttagc tttatgtctt gcctagccag     180
aaaccctaaa acgccaccaa tcccttccct tatccgctgt ccgcctgtcc ggttctccct     240
gaccctgagc cgctcccgta gtcccgtccc aagtggccag gtccagctcc aggagctcca     300
ggcctccagc gcgcgtcgcc gccactttac gcccgtgccc agcgcccag gtagcttacg     360
cccgtgccta gcgccgccac cttacgcccg tgcccagcgc tctaggcccc taggtagctt     420
acgtccagg cctccaggct ccagacctcc agtgcccagg atacatattt gattatatgt     480
ttccctcgag accaggccac accaagggct atgtcgccag tagccgcaga agatgtgcta     540
```

```
gatctccaag acgtaagcaa tgacgattga ggaggcattg acgtcaggga tgaccgcagc      600
ggagagtact gggcccattc agtggatgct ccactgagtt gtattattgt gtgcttttcg      660
gacaagtgtg ctgtccactt tcttttggca cctgtgccac tttattcctt gtctgccacg      720
atgcctttgc ttagcttgta agcaaggatc gcagtgcgtg tgtgacacca cccccttcc       780 g                                                                     781
```

<210> SEQ ID NO 72
<211> LENGTH: 781
<212> TYPE: DNA
<213> ORGANISM: Artificial sequence
<220> FEATURE:
<223> OTHER INFORMATION: Plant viral combination double enhancer

<400> SEQUENCE: 72

```
accaggccac accaagggct atgtcgccag tagccgcaga agatgtgcta gatctccaag       60
acgtaagcaa tgacgattga ggaggcattg acgtcaggga tgaccgcagc ggagagtact      120
gggcccattc agtggatgct ccactgagtt gtattattgt gtgcttttcg acaagtgtg      180 ctgtccactt tcttttggca cctgtgccac tttattcctt gtctgccacg atgcctttgc      240
ttagcttgta agcaaggatc gcagtgcgtg tgtgacacca cccccttcc gctcgaggaa      300 atggctgtta acaggcacga aatgacccga atcgaagcct acagtcacca ctcgactgcc      360
aatcacacga ccaccaatcc cttcccttgt ccacggcctg cacgaaaagt tgtattcatt      420
gtccacggcc gtaggcgaa ggcgaggccc atttagcttt atgtcttgcc tagccagaaa      480
ccctaaaacg ccaccaatcc cttcccttat ccgctgtccg cctgtccggt tctccctgac      540
cctgagccgc tcccgtagtc ccgtcccaag tggccaggtc cagctccagg agctccaggc      600
ctccagcgcg cgtcgccgcc actttacgcc cgtgcccagc gccccaggta gcttacgccc      660
gtgcctagcg ccgccacctt acgcccgtgc ccagcgctct aggcccctag gtagcttacg      720
ctccaggcct ccaggctcca gacctccagt gcccaggata catatttgat tatatgtttc      780
c                                                                     781
```

<210> SEQ ID NO 73
<211> LENGTH: 1460
<212> TYPE: DNA
<213> ORGANISM: Artificial sequence
<220> FEATURE:
<223> OTHER INFORMATION: Plant viral combination double enhancer

<400> SEQUENCE: 73

```
ggtgcagcag aagcaacaag ccccaaagtg gatagcggcc aaagcaacca gcggaagctt       60
cttaattacg gctaggcttc ttaattaagt gcccatcaaa tcaagctgcc aacgcaggca      120
gccagccact ctcgagaagc gtatccgggg cccacaaggt ggaatcaacg ttcaccctgc      180
cgtgacgcct tgtccccagc tacccgccg tctgcctacc ccattccccg cacctccatg      240
gcccacgcgt cagtggtcct gtgactgggt gggcaggtga gcgtgagtcc gtgagaagga      300
agcaagccct gttccgccgt tcgctcgtcc catccgataa ctttaccgtg tgtactgtga      360
ttgtcgctct gacccgcggc accgtgctga agcctcccca cgaccctcgt ggcacggtgg      420
gacatagcga caggcgcctc acgctcctcc cccctcccct ctcttccccc ctgccaggca      480
agagagaaga aacgcacgcg agccgcgagc agaatacagc agcacgggcg ccagcgccat      540
cctgatctcg ctatctccct tctcttctcc cccgatgcga tctcgccaaa ccctaatccc      600
```

```
gccgcccgcc gcgcggccgt cgccggagcc ctagccccga atgtggcggt gacgcccgtg      660
ctgctgtatt ctgctcgcac tggtcctgct cgtggagcac ggcatcggtg agcggggcca      720
gcgccgcggg cggtgcgcgc acggagaagt ccgccggagg ctgccgaggc agcgtcaatg      780
agggagatga gcgcgggctt ggccttgaac gccgcgacgc ggaggagctt gtagaggcac      840
gggaggagcc cccggaggta cacggcgagg tcgtcggtgg gctccgaggc ctcgacggcg      900
gcggcggcag cgagcgcggc ggccagctgc gcgcacttgt cctgctcgtg gagcacgacg      960
tcggtgagcg gggccagcgc cgcgggcggt gcgcgcacgg aggagggacg cagcgcagcg     1020
cggcggctag gagcctggtc acgagcggcg cgacggcatc ccgcgggtgc tccccagcga     1080
cgagcgccag cagccgaagc gagtgatgtc ggatgcggag gtggttggaa gcgcggcggg     1140
gtttgcggga ggacgtgcgg gcactcgaga ccaggccaca ccaagggcta tgtcgccagt     1200
agccgcagaa gatgtgctag atctccaaga cgtaagcaat gacgattgag gaggcattga     1260
cgtcagggat gaccgcagcg gagagtactg ggcccattca gtggatgctc cactgagttg     1320
tattattgtg tgcttttcgg acaagtgtgc tgtccacttt cttttggcac ctgtgccact     1380
ttattccttg tctgccacga tgcctttgct tagcttgtaa gcaaggatcg cagtgcgtgt     1440
gtgacaccac cccccttccg                                                 1460

<210> SEQ ID NO 74
<211> LENGTH: 1091
<212> TYPE: DNA
<213> ORGANISM: Artificial sequence
<220> FEATURE:
<223> OTHER INFORMATION: Plant bacterial combination double enhancer

<400> SEQUENCE: 74
gtaagcctac attcagatct aaaaaccttc actctaggag ttggatgtgg ataaagctac       60
gaaccatact tgtaaccatc tcactaacca acccaaaact tctgtacctg catcgtatat      120
gtgtttatcg tgaatgtatc tacttgtatt tatatatcaa taaaactgaa tcaaaatcag      180
cagcacgtcg ttgaacaaac aaggacaaag acacactaaa ctcatccatc aattcttcca      240
ctcatccatc ttcttggaac acaatcaagg tagctaacaa gctccggagc tccaatccgt      300
gccttgcctg aacggagctg aaccgacctc atcctagtcg gtcatgtatc gcaagttgca      360
aggcaaggtc ataaacctag caaaaataaa cagaacaggc ccgggctgga agcagccgag      420
ctggacgccc ggaccccctcg atggaaaaag aagagaaggg gaaaaagggg taagaagctg      480
ggcctcgatt accacccccg aagcgcttcg gatcggtcgg cggtctcttc ccatcgatc      540 acgcgcgcgg ccgcggcctg cccgaaccga cgccgagcga cacgccgggc gatgcggtca      600
gcaacccggc cctacactgc aaaggaacgc gagcgtcaga acgtcctgag gcagcggcgg      660
ggtcgggggc ggaggtggag aagggggatc cggcgaaccc tcgaggtcgc ggcggtggac      720
ggcgacgcac gccaagcggg ccgttactgg gttggcgacg gagagggaa cggacagaaa      780 agggtgttgg ccggacaccc tttttatcca gcgtggcatg ggcgcttttc cacgtggacg      840
tacgacgctg cgatagacac ctggcagata atatctgacg ggcggatgga caggacgggc      900
gggccgagcg ctggcgccag caggccgcag tacctggagg ctggggcccc ctccgtggtc      960
aggcacgccg tcgcctgtcg gagtcggact atcctcgagt caagagcgga gaattaaggg     1020
agtcacgttt tgaccccgc cgatgacgcg ggacaagccg ttttacgttt ggaactgaca     1080
gaaccgcaac g                                                          1091
```

<210> SEQ ID NO 75
<211> LENGTH: 1593
<212> TYPE: DNA
<213> ORGANISM: Artificial sequence
<220> FEATURE:
<223> OTHER INFORMATION: Plant viral combination double enhancer

<400> SEQUENCE: 75

```
gcctgggccg ccactgctca ttttcggccc acttcattaa cccgccgcgt ggcccgatta      60
ccccacgcc cgcgcgcgca gtcaccctac cgggtccttc gctgaccagc ggggcccaat     120
cgtcatcttc ttcccccact tactcgacgg ctcgacgcag acccaatctc aacagaaatc     180
gccgcatgac tcggatcccg ctactgcttc cctggccgtg cggctgtagc gctactgacg     240
ggcaggcccg ctgaccaacc ttcccatcgc gcacggactt ctttcgcacg cctagcgagt     300
ggagcgcgga ttggtcatcg ggtgagatcc gctgcaagct cgtcttcatc ctctcgtgat     360
taccgtggac tccgcgcaac agaaatccaa gcatcgcggc ctagcaaatc ccatcagagt     420
tcgattccaa cctgcatata attgtgccct catactaccg cacccagatg cataggacgt     480
tcgggtcttc gcgtgcgcca gggagacatc taccgccatg aaacagagag accgaaggag     540
gaagaattgt tgttcctgtt tcttgggatt cttctactat tcaggcgttc atccctcttt     600
ctctcgtggc gacgaagacg accgacgccg acgccctgcg cctggtgcca ggttccgtcg     660
ggtcttcgcc ggcgatggac atccaccatg gccgactggc gagagagaga aaggcaacaa     720
gagcgagaga acgggtgtgt tgccatcggg agggagttca acggagccgt gcactggacg     780
tccaagactt ccctgtgcgt gcggtgtaga gcagacctgg cctcctcgcc gggcgtgaag     840
actgcgcgaa cgccgtcgag tcgtggacct gggcgtgctt caaagagcgc cgcggtttgg     900
ccttgccatc ttgatcgacc ggtaaaattc tttccaccct gttcgcatta acacccctc     960
cgcgtagcac tcttcagatc cgggttttgg gaaccagaga gggaaactat gcatctccgg    1020
cgaacttcat tgtcgtgagc ttggcagcgc cgccgcgcgt gggctgcttg atggggttgt    1080
agctggagaa aggaacagtg gctgtcggat aggcgatgga tggacgagat tatggcatcg    1140
tataccccctt cgcgcgatcg gatttgggcc gtagatgcgg aatcgggccg ttctgatttg    1200
gttagggcgt ggcaagtcat cgaccgttga tcccatatcc aatggaccta gttgcataca    1260
gattcgttat atttgagatc taaccctagc ccttgatttt taatccaacg gctcagaact    1320
acagataccc tttcggcctg gaagacttgc ataagagcca ctctgctttt ctagaataaa    1380
cccgcagtcc acgctcgaga gctgcttgtg gggaccagac aaaaaaggaa tggtgcagaa    1440
ttgttaggcg cacctaccaa aagcaacttt gcctttattg caaagataaa gcagattcct    1500
ctagtacaag tggggaacaa aataacgtgg aaaagagctg tcctgacagc ccactcacta    1560
ttgcgtttga cgaacgcagt gacgaccaca aaa                                  1593
```

<210> SEQ ID NO 76
<211> LENGTH: 1598
<212> TYPE: DNA
<213> ORGANISM: Artificial sequence
<220> FEATURE:
<223> OTHER INFORMATION: Plant viral combination double enhancer

<400> SEQUENCE: 76

```
gaacctaagg ttggaccagc acgcaacgct atctgcagga tcaaagatcg acaggctaga      60
ttttaaacac caagatccac tccaatccgt acgatctgag atctatattt gatcccttcg     120
aagcggtcct aattatctaa tcaagaccga tcagatcgag atcgacgact cctactctct     180
```

```
ctcccttatt cccctcaatg ccttcggacc gaggccacca tggaggcgcc atggccgaga      240
ccggactatg agctccctca atgaatcccc ttcaaattga aacttagcta cacattgctg      300
agactaaggc gagtagttct agggctctct tacctggagt tgggacgacg aggcacccca      360
cccacgtgtt ctgcggttcg gcactggaag gcatgctccg gcgacgaatt cctctatgcc      420
cgaccaccat tcgccttaac gcacgctgct ccccacttcg gtgccctccg tggaacgatt      480
ctgcgcgcac accgagggcc tgacgctgcc atacgtgaat ctatcatagc gactgcttct      540
ctatgctctt tctctgtttc tactatggcg ccgggtgggt ttgctctcgg ctctagggga      600
tgatgggggg ttgctcggcg tctggtttta tagaccctag cgtgggcaag accgaaagac      660
tcggggtcgg ggtcggggtt acccatttc tggtgaagtt tgttgtggca tctgtgcaat       720
cttgtctagg aagaagactc tggacagctg ggcccgttta tcagggttaa gggaacgtgg      780
cgcggagcgg ctgattaggc tgacgacccg gccccagtcg tcagcggcaa aagacgttcg      840
ggctgaggaa agccagagct gacgaggcgg ggcccgcgcg ccatacacac tggaaaaaga      900 aaaggaggg aaacgtaatg ggccagcgag gcatatttgg cccatcagga cagggtggac       960
gccgagaggg agttgggtcg aggagaggtt tcaagcccaa aacgaggtat gtcctctctt     1020
tccaatttgt ttagatttct tttagtgttc taaattctaa cttcaagttt tgatttaatc     1080
tgccgttaaa attttgaact caatttaaat gcgcaaccaa aaatacccag catgatgcag     1140
caatattcat atattttgca ttatttaat aatttactcg agaaaattat ccattccaga      1200
aggtaattat ccaagatgta gcatcaagaa tccaatgttt acgggaaaaa ctatggaagt     1260
attatgttag ctcagcaaga agcagatcaa tatgcggcac atatgcaacc tatgttcaaa     1320
aatgaagaat gtacagatac aagatcctat actgccagaa tacgaagaag aatacgtaga     1380
aattgaaaaa gaagaaccag gcgaagaaaa gaatcttgaa gacgtaagca ctgacgacaa     1440
caatgaaaag aagaagataa ggtcggtgat tgtgaaagag acatagagga cacatgtaag     1500
gtggaaaatg taagggcgga aagtaacctt atcacaaagg aatcttatcc cccactactt     1560 atcctttat atttttccgt gtcatttttg cccttgag                             1598
```

<210> SEQ ID NO 77
<211> LENGTH: 1320
<212> TYPE: DNA
<213> ORGANISM: Artificial sequence
<220> FEATURE:
<223> OTHER INFORMATION: Plant viral combination double enhancer

<400> SEQUENCE: 77

```
ccctttgtcg cgtgcggccc attcctcact cgccctgcct caccgacgtg tgggtcctag       60
cgctcctcct ctcttggtgt ctatggcatg tgggccgtct ggccagaccg tttcaacacg      120
caagggcgca agcctgtcgc gagtcttgta cacgctgaca tgtggcaccc ggtcgtcatc      180
actaacccct caatcgaaga caccacaaca gaatagcggc gccaggtttc tcggtcgggc      240
cgctccaacc gccgttgccc gggtgtgcgg gtcagactcc atgctataaa gagctgagcc      300
ccgtacccct ggaacccttg gaccatctct cgccacccag aacaaggtaa cctcgtcgcc      360
atcaccatag ttgtgggagca ccgccgcagt tggcgaggtg agatcccgcg gggcctcttc      420
aatccgagtc tggggtggc aggctcccta gcgcaaccaa gtgggttcgg ttgtggggac       480
cggtggcacg cggagtacct cagagtggcg gcaattgctc gccgatgcat gccctctggt      540
gcggactacg cctcttcgtg ggcagcgaac tccacatctc tgacttaggt gagacccctc      600
tccgcatgtt cgccatcttc ccctctaggt ttagcaccgg acaattttag gtttggggtg      660
```

```
tttgggcatc ggattgcgtg tccgccggcg aagctccatc gcggcctcgc gggtatgcca      720
tgcggcgctg tcgtgttctt ctgggatggg agatatggtc acgtcagtcg attgctcgct      780
taacggctgc aattagatca aatgtacccc ttcgcgcata acgatccggg ttgccgattc      840
ttgatcaggc ggtcaaaatc aaatccggat atcggtttgg gtaggtgtaa cataagtcat      900
tcgattcaga tcactcgagc aacggagtgg tcgtacatac tacaaatgga ttgccaatag      960
tattcgcaat ggatacacac cgaggttgtt gcgagaaatt ttgtatcacg gtacaattac     1020 caggggcct tacgcgatat gattttattg gcgccacgat tacgaaggta agatttggta     1080
aagaaaaacg caaatgcgat attaattttt cggaattaat tatagaaact tcggtaggaa     1140
atatcgtttt actggcagaa acattcata atggatatta ctctcatgat gtattcgctt     1200
gttttgaagg taaagttgaa acttttcgtt tgtaaataca aaaatgtat atgagtattt     1260 gttgtcggaa tgtcatatca acaatgttgt gtatatatgt gtaaactaaa atacactata     1320
```

<210> SEQ ID NO 78
<211> LENGTH: 1836
<212> TYPE: DNA
<213> ORGANISM: Artificial sequence
<220> FEATURE:
<223> OTHER INFORMATION: Plant viral combination double enhancer

<400> SEQUENCE: 78

```
cgctagatgg gcatgttgat ccttgccaaa acgctcacac agtaggtgac aaaacacata       60
ccatgacatg tacactaatt tttgtttaac agattgcaac caacaggcag ctgcacctaa      120
aaaactcatt gtagcaactt tgatccacac cctatgactc attccataca tggcaaaata      180
atcttcataa tgtttctgcc aaagttttgg gttctcgcca tcgaaactag gaaagttaag      240
gagtggtaat tttcccaact ccaactctaa ccttgcccett ggtggcctag gatcatgata      300
ctcatgtgga tccagatgag aaagtggagg gtgaaacatg aaatcgggcg taccattgat      360
cgggagatgg ttttgggcaa ggagatgccc aaaaccatgc ccccagcgat ttttgtcgaa      420
gcaattccca tctgggctgt cggtgttgta cgcggcagca ggcgagcgct ccgccaccga      480
ctggtacggg ccgagaatac ccgcggcggt atcgagctgt ggcggcggcg cttgggcagc      540
ccacttggac acctcgtcac gcagaagatg cacggaggtg tggatctcgt cgaccgaagc      600
ctccacgtcg ggccgccacg actcgaaggc gcgtaagcc gacacgaggg caccgaggcg      660
cattacgaaa gcggcctcga cttcatcgag gcgctcgatc gctgcggtga cctgggcgtc      720
gagttccacg tggatcgatg tcagactctc gatggcgatg ttggcttcca gatgttgcgg      780
tgacgcggtg ttccacgcga cggttgtctc gagcgtgcac caacgcgtct cctgagcaaa      840
gaggtggtca cagatgtcgc gaagaagctt ggattgttcc tcgatcgcca tcttcaggtt      900
gggctccatg gatccggatt ccttcgcgcg acgcgtgtag taggtgtgtg ctagcgctta      960
gatcagtgtc tccgatatca atttgtgagc gtccgctcca agcaacataa tctaggaatg     1020
acgagagtag gagaagggag attctagagg aagaaggaga tctgataggg aggggaagta     1080
gttgttcgat atatttctct gcctaaaatc gtcacagtgc ctgttcacag tatttaagta     1140
tcaactatta caaggctcga cggcccatta tgccacccag tcctctccta ggaacttggc     1200
attgggcttc ctgatgcggc ggcccaactc cagcccagcc acgtccgacg acgacgcctg     1260
cttcttgacg cacgtcacct gggcgatgct gagagtgctg gttacctgta atcggataca     1320
acgtaatcaa tcggatacat gacatatatt tttcttagtg ctcctccggc tccgtgatcg     1380
```

```
gatcacgctg ctgcatctta aagctgaaa gaaactggga aggtgatgag ttggaccttg    1440
tgctgcccgc tcgagggatt aatggattga tcaacatcct taccgctatg ggtaagattg    1500
atgaaaagtc aaaaacaaaa atcaattatg cacaccagca tgtgttgatc accagctatt    1560
gtgggacacc aatttcgtcc acagacatca acatcttatc gtcctttgaa gataagataa    1620
taatgttgaa gataagagtg ggagccacca ctaaaacatt gctttgtcaa aagctaaaaa    1680
agatgatgcc cgacagccac ttgtgtgaag catgtgaagc cggtccctcc actaagaaaa    1740
ttagtgaagc atcttccagt ggtccctcca ctcacagctc aatcagtgag caacaggacg    1800
aaggaaatga cgtaagccat gacgtctaat cccaca                              1836
```

<210> SEQ ID NO 79
<211> LENGTH: 1054
<212> TYPE: DNA
<213> ORGANISM: Artificial sequence
<220> FEATURE:
<223> OTHER INFORMATION: Plant viral combination double enhancer

<400> SEQUENCE: 79

```
cggcgcttgg gccaaatctt tccccctcg acctaggtag aatcacctgc accggcccat      60
ctccgtggtc tccacggctc aaactcccgc tgtgctggtg cctttggtga ctgccagggc     120
agacccacta ttcagttcca cctctgcgcc aatgactgat gggtctgcct catcatccgc     180
ggttccccat ccacgtgctc ctgctatcac cgtcgtgtgg gccatgtttg tcagtattct     240
cctcaagctc aggatcttaa ccaatcccgc gctgctcact gatatggttg ggaggcaggt     300
gctgggatcc ctgacctcgg tgcattgggc gctcaccttg tccctataaa ttgtcgtgac     360
cgtccctcgc attgaaaacc caagccgaag taccgacacc gtgattacag agattgcaca     420
aggaagagca gggtgaagtc cgccattgga atctgccgtc gtcaactatg catcatgggc     480
atcaccgtcg aaccatcggg caccagccgg ggagcttcgc catggcgcga ggaacgtttt     540
cgtggccccc tcgagaagcc atcgaaaccg gtccactggt aaaccttcaa gatgaagaaa     600
gaaagattct ttgccaaaaa atgcaaaagt acaaagggca cagctgtcag ttgtgcaaat     660
ccgagtcatc tggaccacaa acatcagaag agggtctaca agagtcagaa gacgaagact     720
tttcggtgct agtttaatta ctggcagaca agtggcaga catactgtcc cacaaatgaa      780 gatgaatct gtaaagaaa acgcgtgaaa taatgcgtct gacaaaggtt aggtcggctg       840
cctttaatca ataccaaagt ggtccctacc acgatggaaa aactgtgcag tcggtttggc     900 ttttctgac gaacaaataa gattcgtggc cgacaggtgg gggtccacca tgtgaaggca     960
tcttcagact ccaataatgg agcaatgacg taagggctta cgaaataagt aagggtagtt    1020
tgggaaatgt ccactcaccc gtcagtctat aaat                                 1054
```

<210> SEQ ID NO 80
<211> LENGTH: 1482
<212> TYPE: DNA
<213> ORGANISM: Artificial sequence
<220> FEATURE:
<223> OTHER INFORMATION: Plant viral combination double enhancer

<400> SEQUENCE: 80

```
tgaccagcat tgatacacct gatatgtcaa tcgcctttaa cgaaacaaga ataagaagcc      60 tctcggggt agcaataaga aactccggct cacaagtttt cagtccagag atctagtgtt      120
caatggatgc gccaggatgc aagctcactg aatgaatccc aagaggcttc aggggtttgc     180
atatcgatcg cacttgcgcg gccttatcct gtgacgagac gaggtacagc aggaagggc     240
```

```
aagacacgac catcccatgc ctctctttcc tagcgacgat gtcgcaggca gtggagacga      300
gccacgcggt ctgcgtcacc gtggcgcacg cgccgctagc gtcgagcacg tcggacggtg      360
cctgggtgga gcaacacctc cagagctcca tgccccggtc accggcgcca tggatgctgc      420
cgccgccttt ctcgggcgcc accgcatccc ggatagcgtt gaggcagacc accaggaact      480
tggacagccg gtcgaagtcc ccgtggccct catccacgcc cgtcgccctt cgccatctcg      540
gctgtgctgg ctaggtcgct tcggcgagat agccgccaac cgtcggggag tggaggggtg      600
ggaggtcgac aggagcacga gcagttgggc ggttcttggc ggaatgggag cgcacatcac      660
gaagagtgcc taaagaagat gcacagttgc ttagggtggc cggtgggccc ggcggcgcta      720
gggcaggcac aacgctcgcc catgcgggag cgaggcacga tggccagacg cgttctcgcg      780
agcgcactgg gtgggtcgcg gttgctgggc caggagggg gcgctggcct ggcggcctgg      840
gcgtgggcgc ctgtgcgctg gccacgcgg ggtgggccgg ccacgcacgc tgtaggagcg      900
agccagggac gcggggcagc tgggccgttg gcgcgcgcag cggcccggga gcgcgagcag      960
gatgcggggg gaaggcgaag gcgcgtgggc cggggtggcc gagcggccca ggaagggggg     1020
ggaacgggcc acgattgggg aaaatgaagg ggaaagaatt ctgggctttt tcttttatgt     1080
tcctcttctt ttctttgtcc atttcctcga gatcatctgg agccaacaag ctaggaagcc     1140
gtctgagcaa gatattcaga tccttacaga gttttacttc ggacagtca aaaatgagtt     1200 taacttctca gccgaggtaa aacaagaaat atgcttacgt ctacagaggg atttctctga     1260
agatcatgtt tgccagctat gcgaacaatc atcgggagat cttgagccaa tcaaagagga     1320
gtgatgtaga cctaaagcaa taatggagcc atgacgtaag ggcttacgcc attacgaaat     1380
aattaaaggc tgatgtgacc tgtcggtctc tcagaaacctt tacttttat atttggcgtg     1440 tatttttaaa tttccacggc aatgacgatg tgacctgtgc at                        1482
```

<210> SEQ ID NO 81
<211> LENGTH: 493
<212> TYPE: DNA
<213> ORGANISM: Artificial sequence
<220> FEATURE:
<223> OTHER INFORMATION: Viral double enhancer

<400> SEQUENCE: 81

```
agctgcttgt ggggaccaga caaaaaagga atggtgcaga attgttaggc gcacctacca       60
aaagcaactt tgcctttatt gcaaagataa agcagattcc tctagtacaa gtggggaaca      120
aaataacgtg gaaaagagct gtcctgacag cccactcact attgcgtttg acgaacgcag      180
tgacgaccac aaaactcgag acttttcaac aaagggtatt atccggaaac ctcctcggat      240
tccattgccc agctatctgt cactttattg tgaagatagt ggaaaaggaa ggtggctcct      300
acaaatgcca tcattgcgat aaaggaaagg ctatcgttga agatgcctct gccgacagtg      360
gtcccaaaga tggaccccca cccacgagga gcatcgtgga aaaagaagac gttccaacca      420
cgtcttcaaa gcaagtggat tgatgtgata tctccactga cgtaagggtt gacgaacaat      480
cccactatcc ttc                                                         493
```

<210> SEQ ID NO 82
<211> LENGTH: 1090
<212> TYPE: DNA
<213> ORGANISM: Brachypodium distachyon

<400> SEQUENCE: 82

```
gtacgcccgt ttcccgtcga tcctcctcct tccgttcgtg ttctgtagcc gatcgattcg      60
attcccttac acccgttcgt gttctctcgt ggatcgatcg attgtttgtt gctagaagga     120
actcgtagat ctggcgttta tgaactgtga ttcgggttag tccagatcga ttcaggtcgg     180
tcgtcgttga gcctctcggc tatgtctgga ttatcgtgta gatctgctgg ttcagttgat     240
tatgttcttc taggagtaat ttcgttgggt cagcgcgatt tctgcttaat ctatgctgct     300
tattgcgcct gtacctatct actaagctat gtgcacctgt aattttgcta gattattcgt     360
tcatcctcgt agttggtttg tcacagtaat ccgtatgggt tctgacgatg ttattgttgg     420 tcataccta gcttctccag atttta tttt gttaaaattg gatagatctg ctactgatag      480
ttgatgatgg aatttggtgc tgaatctatg ctatttattg cgcctatacc tgatctatcg     540
ggctatgtac ggctgtagtt tactggatta ttcgttcatc ctcggtagtt ggttcatcgt     600
ttgggttctg acgataatat tgttgattat gcgtaggctt ctgcagattg ttgttaaaat     660
tggatacatc ggttactgat ggttgatgat agatttgtgc tgaacctatc tgtttattgc     720
tcctatacct gatctatagg gctatgtatg cctgtaattt accagattat tcgttcatcc     780
tcgtagttgg ttcatctcta taattcgtat gggttcttat gatgttatcg ttgattatgc     840
ctagtcttat acagattatt gtgtcaagat tgaatatacc tgctactgat cggtgataat     900
ttggttagta gtttgcaatc tgctaggaac acgttaccac tgtaatctgt aaacatggtt     960
tgccagagta gtttgttcta ctactcttga tatggttgct gattttagtc gcctcctttt    1020
ggatcatgta ttgatgtcct tgcagatttc cgtgtactta ccccggcttt tgtgtacttc    1080
gtgttaacag                                                            1090

<210> SEQ ID NO 83
<211> LENGTH: 707
<212> TYPE: DNA
<213> ORGANISM: Brachypodium distachyon

<400> SEQUENCE: 83
gtgtgttgtt catccgtccc gaatccatcc atccctctt cagatgtgtt gttcatggct       60
ctaatagctc tagatctgct tgtttgtgtt gtttagctct agatctactc gcgcgcgctt     120
ctctctcgat ctcctgtaga acaattttgg ttggtttttt gtgcatatcc ttggtaattt     180
tgtctgcaat atggaggagg cttttctaagc tcctacgtag catcgatctt tagaattccc     240
tcggtttctg tttatttctt cgcgagggct ctctgttatc tgtaggagta gctgtaagcg     300
cggttcgtta cggattaatc gtcatgctta gttgaaccta tcggtcgaag gatttgtgtg     360
ggttgtcgtg tagaattgac accatctact tactgtactg atatgccgat ctgtaggata     420
ctcttcatta ctttttgttta ctgctagttg tggtgtagat ttagcattct caaacccatg     480
ctgtagcgtt tctaatattg ttacatagat ctaccggtgc ctgttaattg tattcgatcg     540
ggcgttctta catctgtccg cccacctagt tttatatgtg gtaatcaaaa ttgcgttgac     600
ttcgtgatgc tgtctgtgta ctgtttttaa tcgctcttac ttagatgatc aacatggtga     660
tggttacgat ttactgtttt ctaatccctg ttacttcgat gctgcag                    707

<210> SEQ ID NO 84
<211> LENGTH: 510
<212> TYPE: DNA
<213> ORGANISM: Zea mays

<400> SEQUENCE: 84
gtacgccgct cgtcctcccc cccccccct ctctaccttc tctagatcgg cgttccggtc       60
```

```
cttggttagg gcccggtagt tctacttctg ttcatgtttg tgttagatcc gtgtttgtgt    120
tagatccgtg ctgctagcgt tcgtacacgg atgcgacctg tacgtcagac acgttctgat    180
tgctaacttg ccagtgtttc tctttgggga atcctgggat ggctctagcc gttccgcaga    240
cgggatcgat ttcatatgtt gatgtgggtt ttactgatgc atatacatga tggcatatgc    300
agcatctatt catatgctct aaccttgagt acctatctat tataataaac aagtatgttt    360
tataattatt ttgatcttga tatacttgga tgatggcata tgcagcagct atatgtggat    420
ttttttagcc ctgccttcat acgctattta tttgcttggt actgtttctt ttgtcgatgc    480
tcaccctgtt gtttggtgtt acttctgcag                                    510

<210> SEQ ID NO 85
<211> LENGTH: 1291
<212> TYPE: DNA
<213> ORGANISM: Panicum virgatum

<400> SEQUENCE: 85
gtacggcgat cctcctctcc cttctcccct cgatcgatta tgcgtgttcc gtttccgttt     60
ccgatcgagc gaatcgatgg ttaggaccct tgggggaccc ttggggtgtc gtgtggtggt    120
ctggtttgat ccgcgatatt tctccgttcg tagtgtagat ctgatcgaat ccctggtgaa    180
atcgttgatc gtgctattcg tgtgagggtt cttaggtttg gagttgtgga ggtagttctg    240
atcggtttgt aggtgagatt ttccccatga ttttgcttgg ctcgtttgtc ttggttagat    300
tagatctgcc cgcattttgt tcgatatttc tgatgcagat atgatgaata atttcgtcct    360
tgtatcccgc gtccgtatgt gtattaagtt tgcaggtgct agttaggttt ttcctactga    420
tttgtcttat ccattctgtt tagcttgcaa ggtttggtaa tggtccggca tgtttgtctc    480
tatagattag agtagaataa gattatctca acaagctgtt ggcttatcaa ttttggatct    540
gcatgtgttt cgcatctata tctttgcaat taagatggta gatggacata tgctcctgtt    600
gagttgatgt tgtaccttttt acctgaggtc tgaggaacat gcatcctcct gctactttgt    660
gcttatacag atcatcaaga ttatgcagct aatattcgat cagtttctag tatctacatg    720
gtaaacttgc atgcacttgc tacttatttt tgatatactt ggatgataac atatgctgct    780
ggttgattcc tacctacatg atgaacattt tacaggccat tagtgtctgt ctgtatgtgt    840
tgttcctgtt tgcttcagtc tatttctgtt tcattcctag tttattggtt ctctgctaga    900 tacttacccct gctgggctta gttatcatct tatctcgaat gcattttcat gtttatagat    960
gaatatacac tcagataggt gtagatgtat gctactgttt ctctacgttg ctgtaggttt   1020
tacctgtggc aactgcatac tcctgttgct tcgctagata tgtatgtgct tatatagatt   1080
aagatatgtg tgatggttct ttagtatatc tgatgatcat gtatgctctt ttaacttctt   1140
gctacacttg gtaacatgct gtgatgctgt tgttgattc tgtagcacta ccaatgatga   1200
ccttatctct ctttgtatat gatgtttctg tttgtttgag gcttgtgtta ctgctagtta   1260
cttaccctgt tgcctggcta atcttctgca g                                  1291

<210> SEQ ID NO 86
<211> LENGTH: 129
<212> TYPE: DNA
<213> ORGANISM: Zea mays

<400> SEQUENCE: 86
gtgcggtgcc cccctccctc gctcttcctg gccccgatct gatccgctct ctgcgttagg     60
```

```
gtatgggtga cggggtggca ctcgatctgc cggggttcgga tctgattttc ttgttgtcgg    120
tttatgcag                                                             129
```

<210> SEQ ID NO 87
<211> LENGTH: 980
<212> TYPE: DNA
<213> ORGANISM: Zea mays

<400> SEQUENCE: 87

```
gtaaggcccc ctccacccct ccgcttcccc tcccccgggc gcgctctggc ttcctcccg      60 gatcggcgcg gggcgtgctg gctccgcgcc tgatttcggg ccttttgttt ccttctcgcg    120
gagcgctcgt gtaacgcttc ggatctagct ggattcaggc gggatcgcgg ccgctcggct    180
tcctcgtggc ctgattcgtg gttttcctcg gggagggaat cctgatcgga tcatcgggat    240
tcctcgtgcg gccgggacac gcttgcgagc cagaaacata gtctgcgtgg ccgggattcc    300
acgatctgtg atctagacgt cgggcgcttc gtctatgtgc tcgctgcagg ctgtggcgta    360
ctggcgtggt gcgcggccgc tatggatcag tgcttgtttg ttcgccctgt agcgtgtgaa    420
atcgagctgt gtagatctat ggtctgcgag gtgcggtggc ggtggaatct cggttgatct    480
ttacctcagc ggcgccagtg tagctcgtgt ggctgcagtt catctgcgaa tttggctctc    540
ggcggcttag gtcgcggagc ttggattatg gagcaccagc tgcagcgtga ccctgttggt    600
tctcatgtgg atctgttggc tgaggttgca gacttcaagt gccactgcca ttgaccggag    660
ctgctgcacg attatactgg aatatctagc ggtagtatac tctgctagta ctcaatacgg    720
gtctcctgac aaatgtcttt cgtgtttagg gacctagcac tctagtgtca agactatttg    780
ctggaatatc taatattagc agtttctgta gtggctcagt gcagcctgg tttagaatga     840 tggggacagt tggctgtgcc atgcaaaata aagtgtgtga aagcaactgc ctcttaaact    900
atgggtggtg caagcaggtt atttgaaggg actctccaca ctgtatctcc agttaactat    960
gactgaactt gtggtcgcag                                                980
```

<210> SEQ ID NO 88
<211> LENGTH: 714
<212> TYPE: DNA
<213> ORGANISM: Zea mays

<400> SEQUENCE: 88

```
gtagctaatc ctctgtcgct cgatctttgt ccttgaggtg ctcgatgaga taggcagtgg     60
ttgaaagctg tgctctgttg cctccccgtg cctgaagtga ttcggtcttc tgtttgcgat    120
taattgtagc tactgcgtct ccattctctt agttttttgt ggttttgtgt gcttccatgt    180
ttggatgacc tgattcttac ggatagttgc ttctggattt gataaattac atacgcaccg    240
tgccaccgta gttggacgac ttcttaattg cgcttgcggt cgtgttacgt ggtcttaata    300
aagtcagatc gaattttga ggtgtagagc tgctgcagtt tctatttgac cgatacttgt     360
ctttgtagtt catgcgcagt aagagttgta acctcataat atgaccaaat tcctgatctg    420
ctttatagag ttgttgtgcc taattttgaa ttcgtcttac tggctcaaaa ttatgtgcgc    480
acgcttatta gtttgcccct tatttctct gcctgcttta ttttttata ttacattgat      540 tgctctgttt aatatttgct tctttattt tacactgctt atgcgtatca agctcttttc    600
aagctcaccg gtgacaacgt tagatctagt ttctgatccc atctgataaa ttgtgtcgtt    660
actggtagta ttaatttact agtgtttcta atcgttgatt cgtcttgtta acag          714
```

```
<210> SEQ ID NO 89
<211> LENGTH: 199
<212> TYPE: DNA
<213> ORGANISM: Zea mays

<400> SEQUENCE: 89
gtatgcttgc tgccttgctc ttcctgttga gatgaatcat atatagtata gctgcatact     60
acaaatctgt ttttcaaatt taggttgctt tggcatgatc tatttttttg tcagacagac    120
tttctaagtg gtagctcttg atttcttgtt cttgtacaac tggtgctgct gaatcttgac    180
cgtatagctc gaattgcag                                                  199

<210> SEQ ID NO 90
<211> LENGTH: 106
<212> TYPE: DNA
<213> ORGANISM: Zea mays

<400> SEQUENCE: 90
gtactgatgt ctctctctct ctctctctct tactctcccc tcgatttag atctgcctga      60 aggacgaatc atagtgacct cacgttggtg cgttttctc caccag                    106

<210> SEQ ID NO 91
<211> LENGTH: 783
<212> TYPE: DNA
<213> ORGANISM: Zea mays

<400> SEQUENCE: 91
gtacgcgctc actccgccct ctgcctttgt tactgccacg tttctctgaa tgctctcttg     60
tgtggtgatt gctgagagtg gtttagctgg atctagaatt acactctgaa atcgtgttct    120
gcctgtgctg attacttgcc gtcctttgta gcagcaaaat atagggacat ggtagtacga    180
aacgaagata gaacctacac agcaatacga gaaatgtgta atttggtgct tagcggtatt    240
tatttaagca catgttggtg ttatagggca cttggattca gaagtttgct gttaatttag    300
gcacaggctt catactacat gggtcaatag tatagggatt catattatag gcgatactat    360
aataatttgt tcgtctgcag agcttattat ttgccaaaat tagatattcc tattctgttt    420
ttgtttgtgt gctgttaaat tgttaacgcc tgaaggaata aatataaatg acgaaatttt    480
gatgtttatc tctgctcctt tattgtgacc ataagtcaag atcagatgca cttgttttaa    540
atattgttgt ctgaagaaat aagtactgac agtattttga tgcattgatc tgcttgtttg    600
ttgtaacaaa atttaaaaat aaagagtttc ctttttgttg ctctccttac ctcctgatgg    660
tatctagtat ctaccaactg acactatatt gcttctcttt acatacgtat cttgctcgat    720
gccttctccc tagtgttgac cagtgttact cacatagtct ttgctcattt cattgtaatg    780
cag                                                                  783

<210> SEQ ID NO 92
<211> LENGTH: 1010
<212> TYPE: DNA
<213> ORGANISM: Zea mays

<400> SEQUENCE: 92
gtacgccgct cgtcctcccc cccccccct ctctaccttc tctagatcgg cgttccggtc      60
catagttagg gcccggtagt tctacttctg ttcatgtttg tgttagatcc gtgtttgtgt    120
tagatccgtg ctgctagcgt tcgtacacgg atgcgacctg tacgtcagac acgttctgat    180
tgctaacttg ccagtgtttc tctttgggga atcctgggat ggctctagcc gttccgcaga    240
```

```
cgggatcgat ttcatgattt tttttgtttc gttgcatagg gtttggtttg ccctttttcct    300 ttatttcaat atatgccgtg cacttgtttg tcgggtcatc ttttcatgct ttttttttgtc    360 ttggttgtga tgatgtggtc tggttgggcg gtcgttctag atcggagtag aattctgttt    420
caaactacct ggtggattta ttaattttgg atctgtatgt gtgtgccata catattcata    480
gttacgaatt gaagatgatg gatggaaata tcgatctagg ataggtatac atgttgatgc    540
gggttttact gatgcatata cagagatgct ttttgttcgc ttggttgtga tgatgtggtg    600
tggttgggcg gtcgttcatt cgttctagat cggagtagaa tactgtttca aactacctgg    660
tgtatttatt aattttggaa ctgtatgtgt gtgtcataca tcttcatagt tacgagttta    720
agatggatgg aaatatcgat ctaggatagg tatacatgtt gatgtgggtt ttactgatgc    780
atatacatga tggcatatgc agcatctatt catatgctct aaccttgagt acctatctat    840
tataataaac aagtatgttt tataattatt ttgatcttga tatacttgga tgatggcata    900
tccagcagct atatgtggat ttttttagcc ctgccttcat acgctattta tttgcttggt    960
actgtttctt ttgtcgatgc tcaccctgtt gtttggtgtt acttctgcag              1010

<210> SEQ ID NO 93
<211> LENGTH: 999
<212> TYPE: DNA
<213> ORGANISM: Oryza sativa

<400> SEQUENCE: 93
tcagccagtt tggtggagct gccgatgtgc ctggtcgtcc cgagcctctg ttcgtcaagt     60
atttgtggtg ctgatgtcta cttgtgtctg gtttaatgga ccatcgagtc cgtatgatat    120
gttagtttta tgaaacagtt tcctgtggga cagcagtatg ctttatgaat aagttggatt    180
tgaacctaaa tatgtgctca atttgctcat ttgcatctca ttcctgttga tgttttatct    240
gagttgcaag tttgaaaatg ctgcatattc ttattaaatc gtcatttact tttatcttaa    300
tgagctttgc aatggcctat gggatataaa agattattct ggagggaagt gatgctggaa    360
ggactatgct gtcctgattt atatttggag ccactatgag catttgggct ttcttttcag    420
aacgctgtag gcgtgtgttg aaatctttgc gacattcaat ttgatatatg attcgaggta    480
attgggcttt aatttgtcat ctcatgtaac atcttttttgt ttcttcgctg cttgatttct    540
ctatttcgta gcattggaag ataatagtag aatgatgata tactccaata cttgcaattt    600
caaaaccgtt agaaagaaag gaaaatcacg gctaggggaa aaattctctc tgatgcgtgc    660
atcaccaaaa tctgattgat tgacataagc attggaacac aaatagaaga tggagaggtg    720
gacatgtttc cgagacatag catttgagct gacattgttt ttgatccgtg gctgtgccat    780
acgcgataat ttactaaact ttcccttgcc ccttggtaat ataaagctta taatgtatac    840
accgaaattg aaaaacgtat tagttcactc ttcttccttt ttctcagcaa agcgtgttca    900
tcaattttat tccacatgaa tgtgattgcg aattgtgacc aggaatgcat gatttaacaa    960
tcccgatcaa ccctgttgtc ggtggtggca ctaaaaatt                            999

<210> SEQ ID NO 94
<211> LENGTH: 1013
<212> TYPE: DNA
<213> ORGANISM: Zea mays

<400> SEQUENCE: 94
cgcatcatga tcatgcatca tggactcggc ctactactgt ggatttgtat gccattatag     60
acttggtgct gtgaaagact gcttgatgat ttgcgggttt gttgctgtgt aaaaaaaggt    120
```

```
cccttggctc ccagaagacc atgaaggttc ggatctatca tgtaattcct tgttatctgc      180
caattatgta tggactatgg acatgtgttg cgctgttcaa cttactacta caaataagta      240
atcgatatgt tcccttccca tgtctcggtg acaattgtct ggagaagctt agggtcgtt       300
tgtttgggat tatgtctgga gaacttatt ttaaactaag tgtgagttca agttaagtta       360
gattatataa tctaggcaga ttataattcc aagcgaacag gtccttagtg ttttggaaa       420
atcctaggtg ttcttttggc tacattgttg tgtgtgcaga tcccttgttg gtctgtaagc      480
gtggggaagt aagaatcgtc cgtttctact gaagacctgc tcgagttagg caccgaggat      540
gccggtaacc aaacagagca atagtgtctc tgtgggcaca gtggagtgtg aatctgtgtg      600
atgcaaatcc gtcatttgtt tagcaaaatt ccagcgttg catgatgcag tttctttaac       660
acggacttaa gggaagggaa aaaaatgttg agccaggaga tccttcaatg tgttagactg      720
acgtgatagc caactaaacc acgacgcaat gttgtcgtta atgacaaaaa aactatttgt      780
tcctaaatcc ttggcgacat tgcatggctg tctcatgaga taatggtctc atctcttatt     840
tatctcttat ttatagccgg aagtggtagt gaccccctgct tgattgctcg tatgccatct     900
caagttctca accgtgtcga gcagccattt tcccatctca agcgcatcat cgtttcgttt      960
gacctcatct gctatcctgc tcctagtgca aatcacatgc gacagaaagt gtg             1013

<210> SEQ ID NO 95
<211> LENGTH: 1304
<212> TYPE: DNA
<213> ORGANISM: Zea mays

<400> SEQUENCE: 95
gctcatgacg atcgatctgt tgggtgatgc ctactctgtc catcgtgctc gacttgtctt      60
cctactactg taccactgtc tgtgctcact ttcacgttcc tgacggtgtt gtgttctagt     120
gtatcattgt gcgatcagtt ccatgttctt ggccatgttt tagaataaaa cagaaaactt     180
gtgttcttgg tgtaccactg tgctcacttt catgttcttg acggcgagtt ggaataaaac     240
aagacttgtg tcatggtgta ccattgccat cattttcatg ttaatataaa gatttgacgc     300
aagacgcaac attcgtaaac acatatatcc acatcaaata aattagggcg tgtttggttt     360
acggtagatt ttaagaatct gattttaaga atatattatc gatccaaaca gagtttattc     420
tgtgccttag attctacgct catagaaaca aaatctgtag aatcaatcca tagttgggtt     480
ttcttgggta acgtgaacat gcagattta aaaatctgcg gaaaccaaac gcggccttag       540
agacatttgt gacggtagct atagatgtcc aaacgggcca cccggcacgg acccggcccg     600
aacccgtttc ggcccgatac gaacagggcc aggccaggca cgacccgttg atgcttcggg      660
ccgggtcgag ctggcccacg tgcctagaaa catgcccaaa cccggcacgc acagggaaaa      720
atcgtgtcgg gccggcccgt tggcccggtg ggcctcaagg gaccgggtcg ggcactggcc      780
cgaaccaaca gtagaacggt atataaatac atatatttaa cagaattaat catatataat      840
aacatattat ttatatatat taagacaaca aaatatttat gtatgcattt tatatttatg      900
tatgcattt atatatgttt tggccgcgta tttagtattt atatactatg agagaattaa       960
atgtatttac atatttagta tttatataaa tatgcgggcc gccgtcgggc cgacccattt     1020
atcgggccgg gccggggcca cagcacgcgg gccgccgtat ctgtccatac ccggcccgct     1080
aaacggggccg tgccggcccg gacccgtaac cgaccgtgtc gggccgtgtt ggaccgggc     1140
taaattcgtg tcgtgccacg ggccaaacgg gcggcccgca ctgtttggac atctataacg     1200
```

| | |
|---|---|
| gtagccttct cccaccttac aattatgaca ttgcatcttt tttttatttt ttaatcatta | 1260 |
| attttaattt tcactaatag tgttaaaaga gataggtaaa cggc | 1304 |

<210> SEQ ID NO 96
<211> LENGTH: 1000
<212> TYPE: DNA
<213> ORGANISM: Panicum virgatum

<400> SEQUENCE: 96

| | |
|---|---|
| gccattggtc atccaagctg ctgctgtacc tgggtcgtct ggtctctgcc atgaagggcg | 60 |
| tcttctttga agtatctgtg tcgtttgtct aaactgtgtt tggttttcat gaactggttg | 120 |
| tgtccttgtg ttcctgaaac agtcattgcg gccgcagttg gcttaagcat gaataagtaa | 180 |
| gactcaaatt tgtgctctgt ttatacatta tgccagttct atataaattc tatagctttt | 240 |
| gagttctctt tggcttgtga ggtgtttgtt gcacctccag attcttgctg actcccattt | 300 |
| tgtactgtat gtccatctct gttctgccaa gctcaaattt ctaactgatt gtttgcaagt | 360 |
| gttggattcg atttggagga tctgacatgt ttggtttgtt gctcgagtgt tactagtaga | 420 |
| ttaattaaga agcttttcgc tagttatgga atcgagtagg tctgtgctat gcagaaccct | 480 |
| attttttggta gactcgtgac attgctctga accaggtaat tggggatcat atttaactgg | 540 |
| aggtagacaa agtgactctc tgcgtgtatg tagttttgtg tttgaccatt gcaataagcc | 600 |
| aataactgaa gtagatacgt ttcatactcc taattcaaac tgaatcgatt gtcgtggttt | 660 |
| gttgctccta caatttgcta gttttttttt aactgaacca atgcctctgt ttgctgtgtt | 720 |
| gtggccgctg gctggtgttt gatttgttgt gagagaaaag tactgctggc agacagatgg | 780 |
| ctgttgactg gtgctggttt agtacgagaa aaacactatc ggctggatgc agcgaacaga | 840 |
| gtgaatatcg gagtgtgtct gttgcccaca cattcatgct ttcttttgt ctggatgctg | 900 |
| tgtacaaaat aaatattctg cttcgccatt gccaaacagg cttgcaggcg aaaatctgtc | 960 |
| tggcacctat cctagtaccc taccaatacc gttccaggcc | 1000 |

<210> SEQ ID NO 97
<211> LENGTH: 980
<212> TYPE: DNA
<213> ORGANISM: Oryza sativa

<400> SEQUENCE: 97

| | |
|---|---|
| ttcttcggac ccaagaatgc taagccaaga ggagctgtta tcgccgtcct cctgcttgtt | 60 |
| tctctctttt tgttgctgtt tcttcattag cgtggacaaa gttttcaacc ggcctatctg | 120 |
| ttatcatttt cttctattca aagactgtaa tacctattgc tacctgtggt tctcacttgt | 180 |
| gattttggac acatatgttc ggtttattca aatttaatca gatgcctgat gagggtacca | 240 |
| gaaaaaatac gtgttctggt tgttttttgag ttgcgattat tctatgaaat gaataacatc | 300 |
| gaagttatca tcccagtatt ttcgcatgaa tgttctttc ttctgtcttg tgcatcagtg | 360 |
| atctagtgca tgggagtttg tattgtgatg ttcgacatca cgtaacttcc actttgcctt | 420 |
| tgctgttcga tattttaatg acatgtcaca cacacttctg atacttttct ttcttggcta | 480 |
| ttgtgccagc atgatgcaag atgcatcaca gcatcagata tattctcatc gtcaggcttt | 540 |
| agcagcacac gagcacgctt tgccgcttaa aagttgtacg gcgcagctta gacatcccct | 600 |
| gtagaagtga taatctttc acttttcctt aaacaaattg agaggggaaa tggaaccatg | 660 |
| tggatcagag aagcttttgt ttcttttacac aagaatattt ggtacagtgg gggtcctatg | 720 |
| ttcgtgggtt cgtggcttgg ctgcctgtct tcaaccaagt gttttcagtt caacatgtta | 780 |

```
gcgtgtagaa agagcacaat tctgtttatc tccaaggtaa aatgtggcat tctgttaaag      840
aacatgatcc tgccaatttt ttaagtttca atggaagagg aatgtaaagc tttctatggt      900
ttgtgtacac aacacagtgg aagaggagtg caagctttct atggtttgtg tgcgcgttgt      960
gtgtcagcac ttcaattttg                                                  980
```

<210> SEQ ID NO 98
<211> LENGTH: 1035
<212> TYPE: DNA
<213> ORGANISM: Zea mays

<400> SEQUENCE: 98

```
gtcatgggtc gtttaagctg ccgatgtgcc tgcgtcgtct ggtgccctct ctccatatgg       60
aggttgtcaa agtatctgct gttcgtgtca tgagtcgtgt cagtgttggt ttaataatgg      120
accggttgtg ttgtgtgtgc gtactaccca gaactatgac aaatcatgaa taagtttgat      180
gtttgaaatt aaagcctgtg ctcattatgt tctgtctttc agttgtctcc taatatttgc      240
ctccaggtac tggctatcta ccgtttctta cttaggaggt gtttgaatgc actaaaacta      300
atagttagtg gctaaaatta gttaaaacat ccaaacacca tagctaatag ttgaactatt      360
agctattttt ggaaaattag ttaatagtga ggtagttatt tgttagctag ctaattcaac      420 taacaattt tagccaacta acaattagtt tcagtgcatt caaacacccc cttaatgtta       480
acgtggttct atctaccgtc tcctaatata tggttgattg ttcggtttgt tgctatgcta      540
ttgggttctg attgctgcta gttcttgcta aatccagaag ttctcgtagt atagctcaga      600
ttcatattat ttatttgagt gataagtgat ccaggttatt actatgttag ctaggttttt      660
tttacaagga taaattatct gtgatcataa ttcttatgaa agctttatgt ttcctggagg      720
cagtggcatg caatgcatga cagcaacttg atcacaccag ctgaggtaga tacggtaaca      780
aggttcttaa atctgttcac caaatcattg gagaacacac atacacattc ttgccagtct      840
tggttagaga aatttcatga caaaatgcca aagctgtctt gactcttcac ttttggccat      900
gagtcgtgac ttagtttggt ttaatggacc ggttctccta gcttgttcta ctcaaaactg      960
ttgttgatgc gaataagttg tgatggttga tctctggatt ttgttttgct ctcaatagtg     1020
gacgagatta gatag                                                     1035
```

<210> SEQ ID NO 99
<211> LENGTH: 1000
<212> TYPE: DNA
<213> ORGANISM: Saccharum officinarum

<400> SEQUENCE: 99

```
tcctgggcca tgaagctgtc cttccaggtt cacaagtctg gtgccttctt ctgtccctcc       60
gatggagatt atctgcatgt cgtggtcgtg tcctgatcga atcctcgttg aatccctatg      120
tttttcttca agaaatgtga gtcctatgtc agtctggttg cgtttgtgaa catttctgct      180
gctgagcagc actttggctg gaactgtgca atgaaataaa tggaaccctg gtttctggtt      240
atgtgtgtgt tagctaatgt ttttgaagtg gaagctctaa tcttctatcg cgttgctact      300
acaattctgc ttgtgttttg atgttcttgg tttctgttag ttggttcaga ggaagttttg      360
cttccacaga ctaagatgca gttgaacttt ggttgccctg gtttctagat ttcatttgtg      420
ctggttgagt gatagtaaga aacaaccggt gttcacatat aatcaggttt tgtgctgctc      480
gagtgatcgt caaaaaccac cggtgttcac atctaaaaag gtttcgatcc ccaggtttag      540
```

```
atctcccgtt taattccaaa aaaaaagttc tgtgtacttg catttagttg ggtggttgat    600
gctggaaaga gtaactttca agagtaataa tctttggtga ctactctgtt tcaactgatc    660
aatccctagg aaaggtacac ctttacttag ggaagaaatt cttagaacct tgcactttgt    720
ttcaactgat aatagtatac tttattagat aaaaaatatt cagatatatt agacaccgga    780
tgtcatccac tcatccttac aaacctctgt catggtcctg cagaaatgtt tgccagctcc    840
agtggcttcc tgataaatct gtggagtgcc tgttaatcgg ctgccaattt ttgctgagca    900
ctgtatatat gttagtaagt actattgggc caccaattcg attttgacac agcactattg    960
gtccaccaat tcgattctga cacagcactg cataatttga                         1000

<210> SEQ ID NO 100
<211> LENGTH: 999
<212> TYPE: DNA
<213> ORGANISM: Brachypodium distachyon

<400> SEQUENCE: 100
tttgttctgt gttggggatt gagatgtctg gctgcagttt tagtgtttac taagttttgt     60
ctatgtgcat tgctcgtatt gctgagactc ttgaaactat gtaagcaatg ttcatgtctg    120
tcgtttaaat actgtattcc tatttcggtt cggttaaaac ctgtgtgcta tgatgcttgt    180
gtccttttaa cttctcaggg atctgattgc ttagattgaa cttagttaac tcatgttctg    240
tttccttgat ttcttcgcaa tttgttttg ttctgctatt ccatctttat gtagcagcgt     300
agcctgtaat catgtgatac gtttatgtcc taattttct tttttcactg ttctccgttt     360
ttctgattag aggttggtta ggtttctccg cttctttcgt ccgcagcaga ttttccactt    420
gttgctgctg gcttgaagct agagtacata ataatttcaa tataaataat tactctttgt    480
ttgtaacact gcaactaggc tatcttgacg ttggcctctt aactccaaag tattggtttg    540
tattcccttt tctcgcattc gctgcatacg gcgatcaact tcgtagtaga tcgttatatt    600
ctggcctcga agcacaattt gtcctcagag aatttgtgca cttgagttcc agattctaac    660
taaaatacga atactgtatg ttattctggc cccgaagtac tctttgtcct ttcagaggaa    720
tcatttgggc acctgggttt ccagattcta accaaaaagt tgatattctg gtccccaagc    780
actctgtcct ctcacggcag aatttgtgcc acttggcgtt cagattctaa tcgccttctt    840
gcttgaagga acttcccttc cgactaaaat aatcaaaagc tctttgccct taaaagaag     900 cttaattcat ctcaagaatt aaaaaaacct actaattcat ctaaatattc aaatcgacgg    960
gaattaactc caacacgcga ggctttgact tttgaatta                           999

<210> SEQ ID NO 101
<211> LENGTH: 253
<212> TYPE: DNA
<213> ORGANISM: Agrobacterium tumefaciens

<400> SEQUENCE: 101
gatcgttcaa acatttggca ataaagtttc ttaagattga atcctgttgc cggtcttgcg     60
atgattatca tataatttct gttgaattac gttaagcatg taataattaa catgtaatgc    120
atgacgttat ttatgagatg gttttttatg attagagtcc cgcaattata catttaatac    180
gcgatagaaa acaaaatata gcgcgcaaac taggataaat tatcgcgcgc ggtgtcatct    240
atgttactag atc                                                       253

<210> SEQ ID NO 102
<211> LENGTH: 2627
```

<212> TYPE: DNA
<213> ORGANISM: Zea mays

<400> SEQUENCE: 102

```
tctgcctttc tgttcttcaa acgatgtctc atgtctgcgc tggacaactt tcttgttgcc      60
gcctgtcgct tgcgctgtgc tgactggacg cagctccgga ggtttggttg tgcttggttt     120
tcgtagagaa ctcgccactt gccgcccgca cgttcttggt gtttcctcct ccccgctgtg     180
ttctgcgcac gggcttttc tgagagaccc atgtttccct tttacttta taaacagtat       240
acatgctatg tttctagaag gagggaaac ctaatccccc taatccaatg gcggggagga      300
aatagggtgg ggtggggtgg ggggagggaa atatctcgct acttttaat ccggacaagc      360
tcatttgcgt ttgcgtctga atgatgatga ctgcaatgct gatcgcacct cgggtgtcgg     420
atcaccagct tttggctgct ctcaccaaat cagctgcaag aagattagag cacaaaagaa     480
ttacagaaag agagcctttt tcttttcttc cttgtgggt cctttcatt tcgtgctctc       540
ctttctctgc cagccagtcc gtccttgcgt ccactgcacc tgcacacagg tcacccgac      600
ccgcactgtt ctagactcca ttagaaaaaa aaggtctga acctttccga aaccagccag      660
ccattggtct ggcaggccag catatgctaa ttggatttt tgccgcatc attgagtgcg       720
ccatcaggat ttgaaatcc tggttttgag taatacagta atttggcatt atccattgcc      780
gaattcccaa gctccgtcag cttgaacgtg gaccctacc atctgcacca gctcggcacc      840
tcacgctcgc agcgctagga gcctaggagc agctgcccgt ctatttattg gtccctctcc     900
cgtcccagag aaaccctccc tccctcctcc attggactgc ttgctccctg ttgaccattg     960
gggtatgctt gctgccttgc tctcctgttc atctccgtgc taaacctctg tcctctgggt    1020
gggttttgc tgggattttg agctaatctg ctggtcccgg tagaaaaaga tcatgtcccc     1080
tgacgtgctc aagcgctcgc cttagccgcg tccttgcccc ccgccatttt tgcggtttc    1140
ggtgtgttcc cgtgactcgc cgggtgcgtc atcgcctgaa tcttgtctgg gctctgctga    1200
catgttcttg gctagttggg tttatagatt cctctgatct aaaccgtgcc tgtgctgcgc    1260
acagaactct cccctgtcct ttcctggggt tttggttacg tggtggtagt aagcttggat    1320
ttgcacatgg ataaagttgt tctaagctcc gtgggttgct tgagatcttg ctgttattgc    1380
gtgccgtgct cactttttt gcaatccgag gaatgaattt gtcgtttact cgttttggtg    1440
gattattagc gcgaaaaaaa aactctttt tttttgttct tttactacga aaagcatctt    1500
cttggatttt gctatcttct tttactacga aaaactcttg agtctaggaa tttgaatttg    1560
tgatgtccat tcttgcagtg cgctgtgctt tattgggaag ccaaatccta ttattttctg    1620
cctctagggt ctgaatggaa tcagtactct tgagacagaa aatcaatcca atcaagttga    1680
tttcttcctt taaaatatt atcacagaac taagtgcttg tgcggaatca gtactggctt    1740
ttgtttggtg gaggatcaat acttgctttt gtttgggggt ggcaactgtt ttgctataag    1800
attccatgtt ttcctgttga gatgaatcat atatagtata gctgcatact acaaatctgt    1860
ttttcaaatt taggttgctt tggcatgatc tatttttttg tcagacagac tttctaagtg    1920
gtagctcttg atttcttgtt cttgtacaac tggtgctgct gaatcttgac cgtatagctc    1980
gaattgcagt attctgaacc atcgagccaa ggctgccaag ctgactcgcc tccacagtct    2040
tcgcgaacgc cttggtgcca ccttctcctc ccatcccaat gaactgatag cactcttttc    2100
caggtgggct taccaaaatc atataacttg catttcattc ggtactgaaa gttgttaatt    2160
tgttattctc ttcatgcctg tcttaatagc acacccagat gtaaacacga gattatgcaa    2220
```

```
cttcttactt ggtttctttt gttggcacca tcatgcatgc taattgctaa ggatgttacc    2280
tattcatcct tgactcatat tatcatatgt aatgattta tgatcacgag actattgatt    2340
gtgaagcata gtatagctgt tcttcagttt ttgtacccct ttgtttttt ccttaagcta    2400 gaactggtac aatttagttg ataagacagt gtagtttgta gtacgtcatt tgacagattg    2460
tttgtcttta gctggtaaag tgccatttaa tatctgtatc cttcagatct aataaaaagg    2520
atatgagatg tccatcacaa gaggggaaaa attacatgat ctgagatgta acatccgttt    2580
ttatttgtga aataccactt ctacaggtat cttcactagg gtaaacc                 2627

<210> SEQ ID NO 103
<211> LENGTH: 1947
<212> TYPE: DNA
<213> ORGANISM: Artificial sequence
<220> FEATURE:
<223> OTHER INFORMATION: Truncated, codon optimized for expression in
      maize

<400> SEQUENCE: 103
atggacaaca accccaacat caacgagtgc atccccctaca actgcctgag caaccccgag      60
gtggaggtgc tgggcggcga gcgcatcgag accggctaca cccccatcga catcagcctg     120
agcctgaccc agttcctgct gagcgagttc gtgcccggcg ccggcttcgt gctgggcctg     180
gtggacatca tctggggcat cttcggcccc agccagtggg acgccttcct ggtgcagatc     240
gagcagctga tcaaccagcg catcgaggag ttcgcccgca accaggccat cagccgcctg     300
gagggcctga gcaacctgta ccaaatctac gccgagagct tccgcgagtg ggaggccgac     360
cccaccaacc ccgccctgcg cgaggagatg cgcatccagt tcaacgacat gaacagcgcc     420
ctgaccaccg ccatccccct gttcgccgtg cagaactacc aggtgcccct gctgagcgtg     480
tacgtgcagg ccgccaacct gcacctgagc gtgctgcgcg acgtcagcgt gttcggccag     540
cgctggggct tcgacgccgc caccatcaac agccgctaca cgacctgac ccgcctgatc     600 ggcaactaca ccgaccacgc cgtgcgctgg tacaacaccg gcctggagcg cgtgtggggt     660
ccagacagcc gcgactggat caggtacaac cagttccgcc gcgagctgac cctgaccgtg     720
ctggacatcg tgagcctgtt ccccaactac gacagccgca cctaccccat ccgcaccgtg     780
agccagctga cccgcgagat ttacaccaac cccgtgctgg agaacttcga cggcagcttc     840
cgcggcagcg cccagggcat cgagggcagc atccgcagcc ccacctgat ggacatcctg     900 aacagcatca ccatctacac cgacgcccac cgcggcgagt actactggag cggccaccag     960
atcatggcca gccccgtcgg cttcagcggc cccgagttca ccttcccccct gtacggcact    1020 atgggcaacg ctgcacctca gcagcgcatc gtggcacagc tgggccaggg agtgtaccgc    1080
accctgagca gcaccctgta ccgtcgacct ttcaacatcg gcatcaacaa ccagcagctg    1140
agcgtgctgg acggcaccga gttcgcctac ggcaccagca gcaacctgcc cagcgccgtg    1200
taccgcaaga gcggcaccgt ggacagcctg gacgagatcc cccctcagaa caacaacgtg    1260
ccacctcgac agggcttcag ccaccgtctg agccacgtga gcatgttccg cagtggcttc    1320
agcaacagca gcgtgagcat catccgtgca cctatgttca gctggattca ccgcagtgcc    1380
gagttcaaca acatcatccc cagcagccag atcacccaga tcccccctgac caagagcacc    1440 aacctgggca gcggcaccag cgtggtgaag ggccccggct tcaccggcgg cgacatcctg    1500
cgccgcacca gccccggcca gatcagcacc ctgcgcgtga acatcaccgc ccccctgagc    1560
cagcgctacc gcgtccgcat ccgctacgcc agcaccacca acctgcagtt ccacaccagc    1620
```

-continued

```
atcgacggcc gccccatcaa ccagggcaac ttcagcgcca ccatgagcag cggcagcaac    1680
ctgcagagcg gcagcttccg caccgtgggc ttcaccaccc ccttcaactt cagcaacggc    1740
agcagcgtgt tcaccctgag cgcccacgtg ttcaacagcg gcaacgaggt gtacatcgac    1800
cgcatcgagt tcgtgcccgc cgaggtgacc ttcgaggccg agtacgacct ggagagggct    1860
cagaaggccg tgaacgagct gttcaccagc agcaaccaga tcggcctgaa gaccgacgtg    1920
accgactacc acatcgatca ggtgtag                                        1947
```

<210> SEQ ID NO 104
<211> LENGTH: 648
<212> TYPE: PRT
<213> ORGANISM: Artificial sequence
<220> FEATURE:
<223> OTHER INFORMATION: Truncated protein sequence

<400> SEQUENCE: 104

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300
```

```
Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
                500                 505                 510

Val Asn Ile Thr Ala Pro Leu Ser Gln Arg Tyr Arg Val Arg Ile Arg
            515                 520                 525

Tyr Ala Ser Thr Thr Asn Leu Gln Phe His Thr Ser Ile Asp Gly Arg
530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
                595                 600                 605

Val Thr Phe Glu Ala Glu Tyr Asp Leu Glu Arg Ala Gln Lys Ala Val
            610                 615                 620

Asn Glu Leu Phe Thr Ser Ser Asn Gln Ile Gly Leu Lys Thr Asp Val
625                 630                 635                 640

Thr Asp Tyr His Ile Asp Gln Val
                645
```

METHOD FOR THE TRANSIENT EXPRESSION OF NUCLEIC ACIDS IN PLANTS

RELATED APPLICATIONS

This application claims the benefit of provisional application 63/128,917, filed Dec. 22, 2020, and incorporated by reference in its entirety herein.

FIELD OF THE INVENTION

This invention relates generally to transgenic plants. More specifically, it relates to methods and compositions of expressing transgenes in plants.

SEQUENCE LISTING

This application is accompanied by a sequence listing entitled "82215-US-REG-ORG-NAT-1_ST25.txt", created Dec. 20, 2021, which is approximately 135 kilobytes in size. This sequence listing is incorporated herein by reference in its entirety. This sequence listing is submitted herewith via EFS-Web, and is in compliance with 37 C.F.R. § 1.824(a) (2)-(6) and (b).

BACKGROUND

Evaluation and testing of genetic elements for GM traits relies heavily on stable transformation and it is time and resource intensive. Having an efficient transient assay system for fast screening of genes of interest (GOI) is critical.

Agroinfiltration which requires forcing a bacterial suspension through the stomata and into the leaf air space has been largely unsuccessful in monocots. The challenge is due to limitations for agroinfiltration which is associated with aspects of leaf architecture. Currently in planta transient assay method for monocots is only available for corn, which agrobacteria is delivered into leaf by syringe without needle by pushing through at the back of the leaf by fingers. This method is labor intensive with very large assay variation.

Our invention for in planta transient assay by infecting emerging (developing) leaf roll which is still inside the stem of a growing seedling by agrobacteria is a novel concept. This invention not only makes a transient assay for many plants possible, but it also can increase transient expressed protein level to average 5 fold higher compared the method by syringe infiltration. A maximum of 100 constructs can be analyzed in a single experiment by several analysts working together with an acceptable CV %.

Beside fast screening, this invention can easily generate large amount of fresh transiently expressed tissue which can be used for other purposes such as bioassay or protein production.

SUMMARY

In one embodiment, the disclosure provides a method of transiently expressing a nucleotide sequence in a plant part in planta comprising the steps of: a) wounding a plant part; b) Agrobacterium-infiltrating of an expression cassette comprising at least one nucleotide sequence operably linked to a promoter into the plant part in planta, c) transiently expressing said at least one nucleotide sequence in the plant part.

In one aspect, the disclosure provides a method of transiently expressing a nucleotide sequence in a plant part in planta comprising the steps of: a) wounding a plant part; b) Agrobacterium-infiltrating of an expression cassette comprising at least one nucleotide sequence operably linked to a promoter into the plant part in planta, c) transiently expressing said at least one nucleotide sequence in the plant part, wherein the plant part is a nascent leaf.

In another aspect, the disclosure provides a method of transiently expressing a nucleotide sequence in a plant part in planta comprising the steps of: a) wounding a plant part; b) Agrobacterium-infiltrating of an expression cassette comprising at least one nucleotide sequence operably linked to a promoter into the plant part in planta, c) transiently expressing said at least one nucleotide sequence in the plant part, wherein the plant is a monocot.

In another aspect, the disclosure provides a method of transiently expressing a nucleotide sequence in a plant part in planta comprising the steps of: a) wounding a plant part; b) Agrobacterium-infiltrating of an expression cassette comprising at least one nucleotide sequence operably linked to a promoter into the plant part in planta, c) transiently expressing said at least one nucleotide sequence in the plant part, wherein the plant is a dicot.

In another aspect, the disclosure provides a method of transiently expressing a nucleotide sequence in a plant part in planta comprising the steps of: a) wounding a plant part; b) Agrobacterium-infiltrating of an expression cassette comprising at least one nucleotide sequence operably linked to a promoter into the plant part in planta, c) transiently expressing said at least one nucleotide sequence in the plant part, wherein the plant is selected from the group of maize, sugarcane, and soybean.

In another aspect, the disclosure provides a method of transiently expressing a nucleotide sequence in a plant part in planta comprising the steps of: a) wounding a plant part; b) Agrobacterium-infiltrating of an expression cassette comprising at least one nucleotide sequence operably linked to a promoter into the plant part in planta, c) transiently expressing said at least one nucleotide sequence in the plant part, wherein the plant is 8-10 days old.

In another aspect, the disclosure provides a method of transiently expressing a nucleotide sequence in a plant part in planta comprising the steps of: a) wounding a plant part; b) Agrobacterium-infiltrating of an expression cassette comprising at least one nucleotide sequence operably linked to a promoter into the plant part in planta, c) transiently expressing said at least one nucleotide sequence in the plant part, wherein the wounding a plant part is performed with a needle matrix.

In another aspect, the disclosure provides a method of transiently expressing a nucleotide sequence in a plant part in planta comprising the steps of: a) wounding a plant part; b) Agrobacterium-infiltrating of an expression cassette comprising at least one nucleotide sequence operably linked to a promoter into the plant part in planta, c) transiently expressing said at least one nucleotide sequence in the plant part, wherein the wounding a plant part is performed with a needle matrix, wherein the needle matrix has 2 mm in spacing between each needle.

In another aspect, the disclosure provides a method of transiently expressing a nucleotide sequence in a plant part in planta comprising the steps of: a) wounding a plant part; b) Agrobacterium-infiltrating of an expression cassette comprising at least one nucleotide sequence operably linked to a promoter into the plant part in planta, c) transiently expressing said at least one nucleotide sequence in the plant part, wherein the wounding of a plant part is performed with a needle matrix, wherein the needle matrix has 2 mm in spacing between each needle, wherein the needle spacing produces assays with equal distances between wound sites in order to generate equal damage on leafroll to reduce assay variation.

In another aspect, the disclosure provides a method of transiently expressing a nucleotide sequence in a plant part in planta comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part, wherein the wounding of a plant part is performed with a needle matrix, wherein the needle matrix has 2 mm in spacing between each needle, wherein the needle spacing produces assays with equal distances between wound sites in order to generate equal damage on leafroll to reduce assay variation, wherein the needle matrix has 0.2 mm diameter needles.

In another aspect, the disclosure provides a method of transiently expressing a nucleotide sequence in a plant part in planta comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part, wherein *Agrobacterium*-infiltrating comprises cutting the plant above the second node and pipetting agrobacteria onto the cut site wherein the agrobacteria enter the leafroll and infect a wounded nascent leaf.

In another aspect, the disclosure provides a method of transiently expressing a nucleotide sequence in a plant part in planta comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part, wherein the coefficient of variation between samples is <35%.

In another aspect, the disclosure provides a method of transiently expressing a nucleotide sequence in a plant part in planta comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part, wherein the increased transiently expressed protein level is 3 fold higher compared the method by syringe infiltration.

In another embodiment, the disclosure provides a method to generate large amount of fresh transiently expressed tissue for bioassay or protein production comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part.

BRIEF DESCRIPTION OF THE SEQUENCES IN THE SEQUENCE LISTING

Figure 1:
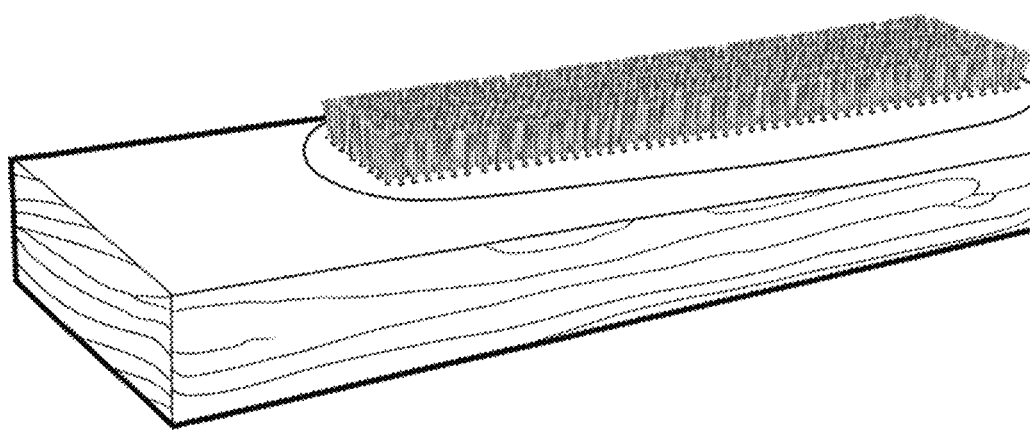
FIG. 1 a needle matrix model with equal needle distance was designed to treat the plant stem against a wood board in order to create equal damage for leafroll. The needle matrix can be made by any materials.
Figure 2:
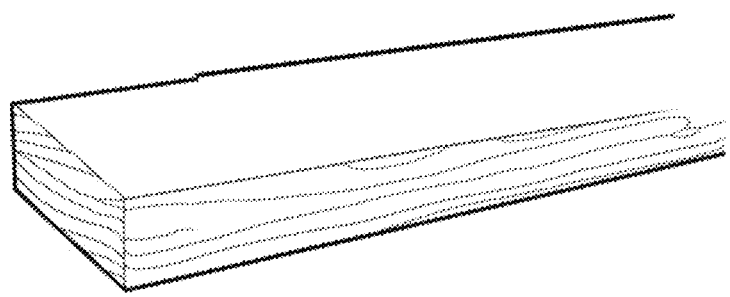
FIG. 2 shows a working needle matrix made from a wire brush.
Figure 2:
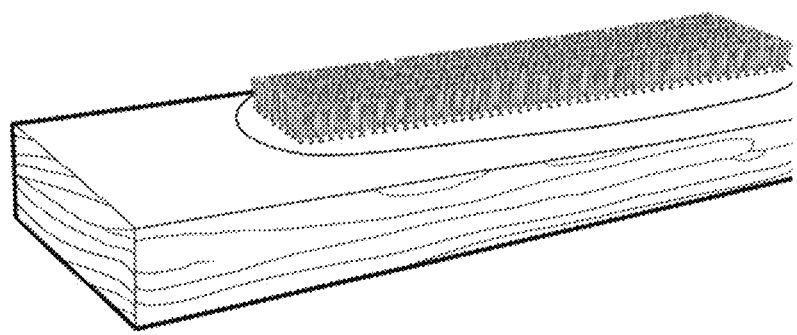

SEQ ID NO: 1 is plant enhancer eZm00001d002338 (eZm1).
SEQ ID NO: 2 is plant enhancer eZm00001d004841 (eZm2).
SEQ ID NO: 3 is plant enhancer eZm00001d005179 (eZm3).
SEQ ID NO: 4 is plant enhancer eZm00001d005798 (eZm4).
SEQ ID NO: 5 is plant enhancer eZm00001d017850 (eZm5).
SEQ ID NO: 6 is plant enhancer eZm00001d020804 (eZm6).
SEQ ID NO: 7 is plant enhancer eZm00001d029426 (eZm7).
SEQ ID NO: 8 is plant enhancer eZm00001d030618 (eZm8).
SEQ ID NO: 9 is plant enhancer eZm00001d034223 (eZm9).
SEQ ID NO: 10 is plant enhancer eZm00001d034223 (eZm10).
SEQ ID NO: 11 is plant enhancer eZm00001d035657 (eZm11).
SEQ ID NO: 12 is plant enhancer eZm00001d035693 (eZm12).
SEQ ID NO: 13 is plant enhancer eZm00001d039526 (eZm13).
SEQ ID NO: 14 is plant enhancer eZm00001d041480 (eZm14).
SEQ ID NO: 15 is plant enhancer eZm00001d045635 (eZm15).
SEQ ID NO: 16 is plant enhancer eZm00001d046472 (eZm16).
SEQ ID NO: 17 is plant enhancer eZm00001d048707 (eZm17).
SEQ ID NO: 18 is plant enhancer eZm00001d052734 (eZm18).
SEQ ID NO: 19 is plant enhancer eZm00001d053090 (eZm19).
SEQ ID NO: 20 is viral enhancer eMSV8.
SEQ ID NO: 21 is plant enhancer eZm00001d050403 (eZm21).
SEQ ID NO: 22 is plant enhancer eZm00001d015463 (eZm22).
SEQ ID NO: 23 is enhancer eNOS.
SEQ ID NO: 24 is viral enhancer eFMV.
SEQ ID NO: 25 is viral enhancer e35S.
SEQ ID NO: 26 is viral enhancer eCsVMV.
SEQ ID NO: 27 is viral enhancer eCvi.
SEQ ID NO: 28 is viral enhancer eFMV.
SEQ ID NO: 29 is viral enhancer eFMVsg.
SEQ ID NO: 30 is viral enhancer eMMV.
SEQ ID NO: 31 is viral enhancer eCmYLCV.
SEQ ID NO: 32 is viral enhancer ePCISV.
SEQ ID NO: 33 is viral enhancer eRTBV.

SEQ ID NO: 34 is viral enhancer eScBV.
SEQ ID NO: 35 is viral enhancer eScBVIM.
SEQ ID NO: 36 is viral enhancer eBBRV.
SEQ ID NO: 37 is viral enhancer eCERV-s.
SEQ ID NO: 38 is viral enhancer eCERV-L.
SEQ ID NO: 39 is viral enhancer eCoYMV.
SEQ ID NO: 40 is viral enhancer eDCMV_p2.
SEQ ID NO: 41 is viral enhancer eMSV1.
SEQ ID NO: 42 is viral enhancer eMSV2.
SEQ ID NO: 43 is viral enhancer eMSV3.
SEQ ID NO: 44 is viral enhancer eMSV4.
SEQ ID NO: 45 is viral enhancer eMSV5.
SEQ ID NO: 46 is viral enhancer eMSV6.
SEQ ID NO: 47 is viral enhancer eMSV7.
SEQ ID NO: 48 is viral enhancer eMDV.
SEQ ID NO: 49 is viral double enhancer e35s:eFMV.
SEQ ID NO: 50 is plant-viral combination double enhancer eZm21:eScBV
SEQ ID NO: 51 is viral double enhancer eCsVMV:eNOS.
SEQ ID NO: 52 is viral double enhancer eCsVMV: eScBV.
SEQ ID NO: 53 is viral double enhancer eCsVMV: eMMV.
SEQ ID NO: 54 is viral-bacterial combination double enhancer eCvi:eNOS.
SEQ ID NO: 55 is viral double enhancer eCvi:eCsVMV.
SEQ ID NO: 56 is viral-bacterial combination double enhancer eMMV:eNOS.
SEQ ID NO: 57 is viral double enhancer eMMV:eScBV.
SEQ ID NO: 58 is viral double enhancer eMMV: eCsVMV.
SEQ ID NO: 59 is viral double enhancer eCmYLCV: ePCISV.
SEQ ID NO: 60 is viral double enhancer eCmYLCV: eScBV.
SEQ ID NO: 61 is viral double enhancer eCmYLCV: eCvi.
SEQ ID NO: 62 is viral double enhancer ePCISV:eScBV.
SEQ ID NO: 63 is viral double enhancer ePCISV: eCsVMV.
SEQ ID NO: 64 is viral double enhancer ePCISV:eCvi.
SEQ ID NO: 65 is viral double enhancer eFMVsg: ePCISV.
SEQ ID NO: 66 is plant-viral combination double enhancer eZm1:eCsVMV.
SEQ ID NO: 67 is plant-viral combination double enhancer eCsVMV:eZm1.
SEQ ID NO: 68 is plant-viral combination double enhancer eZm1:eMMV.
SEQ ID NO: 69 is plant-viral combination double enhancer eZm3:eMMV.
SEQ ID NO: 70 is plant-viral combination double enhancer eMMV:eZm3.
SEQ ID NO: 71 is plant-viral combination double enhancer eZm8:eScBV.
SEQ ID NO: 72 is plant-viral combination double enhancer eScBV:eZm8.
SEQ ID NO: 73 is plant-viral combination double enhancer eZm5:eScBV.
SEQ ID NO: 74 is plant-bacterial combination double enhancer eZm7:eNOS.
SEQ ID NO: 75 is plant-viral combination double enhancer eZm11:eFMV.
SEQ ID NO: 76 is plant-viral combination double enhancer eZm14:eCsVMV.
SEQ ID NO: 77 is plant-viral combination double enhancer eZm15:eCvi.
SEQ ID NO: 78 is plant-viral combination double enhancer eZm18:eMMV.
SEQ ID NO: 79 is plant-viral combination double enhancer eZm22:eCmYLCV.
SEQ ID NO: 80 is plant-viral combination double enhancer eZm19:ePCISV.
SEQ ID NO: 81 is viral double enhancer eFMV-06:e35s.
SEQ ID NO: 82 is intron iBdUbi10.
SEQ ID NO: 83 is intron iBdEF1a.
SEQ ID NO: 84 is intron iUbi1.
SEQ ID NO: 85 is intron iPvUbi1.
SEQ ID NO: 86 is intron iZmGRMZM2G088088.
SEQ ID NO: 87 is intron iZmABP3.
SEQ ID NO: 88 is intron iZmGRMZM2G149768.
SEQ ID NO: 89 is intron iZm061393.
SEQ ID NO: 90 is intron iZm009722.
SEQ ID NO: 91 is intron iZmHSP70.
SEQ ID NO: 92 is intron iUbi1.
SEQ ID NO: 93 is plant terminator tOsRubiq2.
SEQ ID NO: 94 is plant terminator tZmABP.
SEQ ID NO: 95 is plant terminator tZmUGTBx9.
SEQ ID NO: 96 is plant terminator tPvUbi1.
SEQ ID NO: 97 is plant terminator tOsAct1.
SEQ ID NO: 98 is plant terminator tUbi1.
SEQ ID NO: 99 is plant terminator tSoUbi4.
SEQ ID NO: 100 is plant terminator tBdEF1a.
SEQ ID NO: 101 is terminator tNOS from *Agrobacterium* Nopaline Synthase gene.
SEQ ID NO: 102 is maize ubiquitin-1 promoter prZm061393.
SEQ ID NO: 103 is the coding sequence for a truncated, maize optimized Cry1Ab gene.
SEQ ID NO: 104 is the polypeptide sequence for a truncated, maize optimized Cry1Ab protein.

Definitions

Although the following terms are believed to be well understood by one of ordinary skill in the art, the following definitions are set forth to facilitate understanding of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

All patents, patent publications, non-patent publications referenced herein are incorporated by reference in their entireties for the teachings relevant to the sentence or paragraph in which the reference is presented. In case of a conflict in terminology, the present specification is controlling.

As used herein, the terms "a" or "an" or "the" may refer to one or more than one, unless the context clearly and unequivocally indicates otherwise. For example, "an" endogenous nucleic acid can mean one endogenous nucleic acid or a plurality of endogenous nucleic acids.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). With regard to a temperature the term "about" means±1° C., preferably ±0.5° C. Where the term "about" is used in the context of this invention (e.g., in combinations with temperature or molecular weight values) the exact value (i.e., without "about") is preferred.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above.

As used herein, a "biologically active fragment" refers to a fragment of a reference sequence that has activity that is substantially equivalent to (e.g., at least 90% equivalent to) or greater than the activity of a reference sequence. For example, a biologically active fragment of a reference promoter would be a fragment that is capable of driving expression of a coding sequence at a substantially equivalent or higher level compared to the reference promoter. In some instances, a biologically active fragment may also be referred to as a "functional fragment".

A "coding sequence" is a nucleic acid sequence that is transcribed into RNA such as mRNA, rRNA, tRNA, snRNA, sense RNA or antisense RNA. In some embodiments, the RNA is then translated in an organism to produce a protein.

As used herein, the terms "elite" and/or "elite line" refer to any line that is substantially homozygous and has resulted from breeding and selection for desirable agronomic performance.

A "transcriptional enhancer" (herein also referred to as "enhancer", "enhancer sequence" or "enhancer element") is a nucleotide sequence that can stimulate transcription, such as by stimulating promoter activity. The transcriptional enhancer can be an innate element of the promoter or a heterologous element inserted to enhance the transcriptional level and/or tissue specificity of an associated promoter. The primary sequence of the transcriptional enhancer can be present on either strand of a double-stranded DNA molecule and is capable of functioning even when placed either upstream or downstream from the promoter. Typically, transcriptional enhancers are 50-1000 bps in length and are bound by activator proteins, including transcription factors. However, some enhancers, such as plant enhancers, may be larger than 1 kb in size. When bound, they result in an accessible chromatic structure which promotes gene expression. Enhancer sequences are distinct from sequences corresponding to promoters and transcription start sites. In some examples, enhancers include GC rich motifs.

Enhancers augment transcriptional activity from an operably linked promoter and heterologous polynucleotide sequence by at least 10%, relative to transcriptional values obtained without the enhancer. As non-limiting examples, the inclusion of an enhancer, such as the enhancer elements of the present disclosure, can augment transcription of a gene of interest via an operably linked promoter by at least 10%, at least 20%, at least 50%, at least 100%, at least 150%, at least 200%, at least 300%, or any value therebetween. Still higher levels of transcription are also possible.

Enhancers may be identified by applying a computational approach and by using a combination of genomic and epigenomic technologies. For example, sequence conservation of non-coding regions can be used to predict the presence of enhancers. By comparing the sequence data to experimental data, such as one or more of measured DNA methylation levels, DNase sensitivity, histone modification levels, specific chromatin features (such as measured chromatin accessibility) and differential expression levels of nucleotide sequences, enhancer sequences and their putative targets may be predicted with higher accuracy.

Enhancer sequences may be classified based on their source of origin. For example, plant enhancer sequences used herein refer to enhancer sequences retrieved from plant genomic data that, in their natural state, promote transcription of plant genes from plant promoters. As another example, viral enhancer sequences used herein refer to enhancer sequences retrieved from viral genomic data that, in their natural state, promote transcription of viral genes from viral promoters. Enhancer sequences may be heterologous to a promoter they are operably linked to in an expression cassette to induce the expression of a polynucleotide sequence. That is, the enhancer is derived from a different organism than the promoter which it is enhancing, as well as the gene whose expression it is enhancing. Further, in expression cassettes comprising multiple enhancers operably linked to each other and operably linked to a promoter, the enhancer elements may be heterologous to each other. For example, a viral enhancer may be operably linked to a plant enhancer in an expression cassette.

The term "chimeric enhancer" or "chimeric transcriptional enhancer" as used herein refers to the juxtaposition of multiple (e.g., two or more) transcriptional enhancer elements in a construct, wherein each of the multiple enhancer elements are operably coupled to the same promoter. In one example embodiment, the multiple enhancer elements are heterologous to each other; that is, derived from different sources. Heterologous enhancers may include enhancer elements derived from different organisms (e.g., bacterial versus viral versus plant). Alternatively, heterologous enhancers may include enhancer elements derived from different species of the same organism (e.g., multiple plant enhancers from different plant species; or multiple viral enhancers from different virus species). Typically, the multiple transcriptional enhancer elements are positioned abutting each other in the chimeric enhancer with minimal space between them (e.g., no space between them or separated by one or more restriction site sequences). Each of the enhancer elements of the chimeric enhancer are positioned upstream of a common promoter and a coding sequence driven by the promoter in the construct. The enhancer elements included in the chimeric enhancer may include any combination of plant, viral, bacterial, and synthetic enhancers. In some examples, the chimeric enhancer comprises multiple copies (e.g., two, three, or more copies) of the same enhancer element positioned consecutively. In other examples, the chimeric enhancer comprises at least a first enhancer element contiguous to a second, different enhancer element. Additional enhancer elements may also be present. The at least first and at least second enhancer elements may both be plant enhancers or viral enhancers or bacterial enhancers.

Alternatively, the chimeric enhancer may comprise at least a plant enhancer juxtaposed next to a viral enhancer, such as a plant enhancer upstream of the viral enhancer, or a viral enhancer upstream of a plant enhancer. As another example, the chimeric enhancer may comprise at least a plant enhancer juxtaposed next to a bacterial enhancer, such as a plant enhancer upstream of the bacterial enhancer, or a bacterial enhancer upstream of a plant enhancer. As yet another example, the chimeric enhancer may comprise at least a bacterial enhancer, a viral enhancer, a plant enhancer, or fragments thereof, in any combination.

The term "double enhancer" as used herein refers to the juxtaposition of two transcriptional enhancer elements in a construct, wherein each of the two enhancer elements are operably coupled to the same promoter. Typically, the enhancer elements are positioned abutting each other with a minimal space between them (e.g., no space between them or separated by one or more restriction site sequences). Both enhancer elements of the double enhancer are positioned upstream of a promoter and a coding sequence driven by the promoter in the construct. The enhancers included in the double enhancer may include any combination of plant, viral, bacterial, and synthetic enhancers. In some examples, the double enhancer comprises two copies of the same enhancer element positioned consecutively. In other examples, the double enhancer comprises a first enhancer element contiguous to a second, different enhancer element. The first and second enhancer elements may both be plant enhancers or viral enhancers or bacterial enhancers. Alternatively, the double enhancer may comprise a plant enhancer juxtaposed next to a viral enhancer, such as a plant enhancer upstream of the viral enhancer, or a viral enhancer upstream of a plant enhancer. As another example, the double enhancer may comprise a plant enhancer juxtaposed next to a bacterial enhancer, such as a plant enhancer upstream of the bacterial enhancer, or a bacterial enhancer upstream of a plant enhancer. While the double enhancers of the present disclosure are illustrated herein via combinations of viral and plant enhancers, this is not meant to be limiting. In further examples, any combination of viral, bacterial or plant transcriptional enhancer elements (including identified or putative enhancer elements) may be used without departing from the scope of the invention.

The term "expression" when used with reference to a polynucleotide, such as a gene, ORF or portion thereof, or a transgene in plants, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (e.g., if a gene encodes a protein), through "translation" of mRNA. Gene expression can be regulated at many stages in the process. For example, in the case of antisense or dsRNA constructs, respectively, expression may refer to the transcription of the antisense RNA only or the dsRNA only. In embodiments, "expression" refers to the transcription and stable accumulation of sense (mRNA) or functional RNA. "Expression" may also refer to the production of protein.

"Expression cassette" as used herein means a nucleic acid molecule capable of directing expression of a particular polynucleotide or polynucleotides in an appropriate host cell, comprising a promoter operably linked to the polynucleotide or polynucleotides of interest which is/are operably linked to termination signals. It also typically comprises polynucleotides required for proper translation of the polynucleotide or polynucleotides of interest. Further, the expression cassette can include one or more enhancers operably linked to the promoter to augment activity (general or tissue-specific activity) of the promoter, and thereby transcription of the polynucleotide sequence driven by the promoter. The expression cassette may also comprise polynucleotides not necessary in the direct expression of a polynucleotide of interest, but which are present due to convenient restriction sites for removal of the cassette from an expression vector. The expression cassette comprising the polynucleotide(s) of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e. the particular polynucleotide of the expression cassette does not occur naturally in the host cell and must have been introduced into the host cell or an ancestor of the host cell by a transformation process known in the art. The expression of the polynucleotide(s) in the expression cassette is generally under the control of a promoter. In the case of a multicellular organism, such as a plant, the promoter can also be specific or preferential to a particular tissue, or organ, or stage of development. An expression cassette, or fragment thereof, can also be referred to as "inserted polynucleotide" or "insertion polynucleotide" when transformed into a plant.

As used herein, the term "genome editing agent" refers to an agent that is capable of inducing a deletion, insertion, indel, or other modification in the genome of a cell, e.g., by creating a single or double-stranded break in the genome. Examples of genome editing agents include CRISPR/Cas agents (e.g., Cas proteins and guide RNAs), transcription activator-like effector nucleases (TALENs), DNA-guided nucleases, meganucleases, recombinases, and zinc finger nucleases. Cas proteins include Cas9, Cpf1 (also known as Cas12a), C2c1, C2c2, and C2c3, and functional variants thereof. Example Cas9 and Cpf1 proteins include *Streptococcus pyogenes* Cas9 (SpCas9), *Streptococcus thermophilus* Cas9 (StCas9), *Streptococcus pasteurianus* (SpaCas9), *Campylobacter jejuni* Cas9 (CjCas9), *Staphylococcus aureus* (SaCas9), *Francisella novicida* Cas9 (FnCas9), *Neisseria cinerea* Cas9 (NcCas9), *Neisseria meningitis* Cas9 (NmCas9), *Francisella novicida* Cpf1 (FnCpf1), Acidaminococcus sp. Cpf1 (AsCpf1), or Lachnospiraceae bacterium ND2006 Cpf1 (LbCpf1). A "variant" of a Cas protein refers to a protein or polypeptide derivative of a wild type Cas protein, e.g., a protein having one or more point mutations, insertions, deletions, truncations, a fusion protein, or a combination thereof. In certain embodiments, the Cas variant is a functional variant which substantially retains the nuclease activity of or has better nuclease activity than the wild type Cas protein. Example guide RNAs include single guide RNAs and dual guide RNAs.

A "heterologous" nucleic acid sequence is a nucleic acid sequence not naturally associated with a host cell into which it is introduced, including non-naturally occurring multiple copies of a naturally occurring nucleic acid sequence. A nucleic acid sequence can also be heterologous to other nucleic acid sequences with which it may be associated, for example in a nucleic acid construct, such as e.g., an expression vector. As one nonlimiting example, a promoter may be present in a nucleic acid construct in combination with one or more regulatory element (e.g., enhancer element) and/or coding sequences that do not naturally occur in association with that particular promoter, i.e., they are heterologous to the promoter.

In some embodiments, the heterologous sequence is a nucleic acid or gene of interest that encodes an RNA or protein of interest. In some embodiments, the RNA or protein of interest is capable of conferring upon a plant a desired characteristic such as antibiotic resistance, virus resistance, insect resistance, disease resistance, resistance to other pests, herbicide tolerance, improved nutritional value, improved performance in an industrial process, and altered reproductive capability. As one example, such as in the constructs described herein, the gene of interest that is operably coupled to a promoter and an enhancer sequence is truncated, maize optimized Cry1Ab gene that codes for a Bt toxin protein that confers resistance to insects (e.g., one or more insects of order Lepidoptera).

As used herein, the term "intron" refers to a nucleotide sequence provided within a gene (that is, in an intragenic region) and that is removed by splicing during maturation of a final RNA product. Thus, introns are non-coding regions of an RNA transcript, or the DNA encoding it. Introns separate exons such that splicing results in removal of introns and joining of exons. Introns are marked by the presence of conserved sequences known as splice sites at 5' and 3' ends. Typically, the splice site at the 5' end includes an AG sequence and the splice site at the 3' end includes a GU sequence. Splicing of the introns is catalyzed by a spliceosome comprising RNA and proteins. Promoter sequences can, in some embodiments (e.g., for larger promoter sequences such as those for proximal or distal promoters) include an intron. In other embodiments, as described with reference to the constructs disclosed herein, introns may be optionally coupled to a minimal or core promoter sequence.

An "isolated" nucleic acid molecule or nucleotide sequence or an "isolated" polypeptide is a nucleic acid molecule, nucleotide sequence or polypeptide that, by the hand of man, exists apart from its native environment and/or has a function that is different, modified, modulated and/or altered as compared to its function in its native environment and is therefore not a product of nature. An isolated nucleic acid molecule or isolated polypeptide may exist in a purified form or may exist in a non-native environment such as, for example, a recombinant host cell. Thus, for example, with respect to polynucleotides, the term isolated means that it is separated from the chromosome and/or cell in which it naturally occurs. A polynucleotide is also isolated if it is separated from the chromosome and/or cell in which it naturally occurs and is then inserted into a genetic context, a chromosome, a chromosome location, and/or a cell in which it does not naturally occur. The recombinant nucleic acid molecules and nucleotide sequences of the invention can be considered to be "isolated" as defined above.

Thus, an "isolated nucleic acid molecule" or "isolated nucleotide sequence" is a nucleic acid molecule or nucleotide sequence that is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a translation start site or transcription start site of a coding sequence. The term therefore includes, for example, a recombinant nucleic acid that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant nucleic acid that is part of a hybrid nucleic acid molecule encoding an additional polypeptide or peptide sequence. An "isolated nucleic acid molecule" or "isolated nucleotide sequence" can also include a nucleotide sequence derived from and inserted into the same natural, original cell type, but which is present in a non-natural state, e.g., present in a different copy number, and/or under the control of different regulatory sequences than that found in the native state of the nucleic acid molecule.

The term "isolated" can further refer to a nucleic acid molecule, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid molecule, nucleotide sequence or polypeptide that is not naturally occurring as a fragment and would not be found as such in the natural state. "Isolated" does not necessarily mean that the preparation is technically pure (homogeneous), but it is sufficiently pure to provide the polypeptide or nucleic acid in a form in which it can be used for the intended purpose.

In representative embodiments of the invention, an "isolated" nucleic acid molecule, nucleotide sequence, and/or polypeptide is at least about 5%, 10%, 15%, 20%, 25%, 30%, 40%, 50%, 60%, 70%, 75%, 80%, 85%, 90%, 95%, 97%, 98%, 99% pure (w/w) or more. In other embodiments, an "isolated" nucleic acid, nucleotide sequence, and/or polypeptide indicates that at least about a 5-fold, 10-fold, 25-fold, 100-fold, 1000-fold, 10,000-fold, 100,000-fold or more enrichment of the nucleic acid (w/w) is achieved as compared with the starting material.

The term "introducing" or "introduce" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell. Transformation of a cell may be stable or transient. Thus, a transgenic plant cell, plant and/or plant part of the invention can be stably transformed or transiently transformed. In a transient transformation, the introduced heterologous nucleic acid does not get integrated into the genome of the transgenic plant cell, plant and/or plant part. In a stable transformation, the introduced heterologous nucleic acid does get integrated into the genome of the transgenic plant cell, plant and/or plant part and can be passed on to future generations of the cell.

The terms "percent sequence identity" or "percent identity" are used interchangeably herein and is used herein refers to the percentage of identical nucleotides or amino acids in a linear polynucleotide or amino acid sequence of a reference ("query") sequence (or its complementary strand) as compared to a test ("subject") sequence (or its complementary strand) when the two sequences are optimally aligned. Optimal alignment of sequences for aligning a comparison window are known to those skilled in the art and may be conducted using known methods, e.g., using known software or computer programs such as the Smith and Waterman algorithm implemented in the EMBOSS-6.6.0 water tool using default matrix files EBLOSUM62 for protein, EDNAFULL for DNA with default gap penalties. EMBOSS-6.6.0 is available, e.g., from the following Biosoft and Open-Bio such as at the following websites: en.biosoft.net/format/emboss.html or emboss.open-bio.org/html/adm/ch01s01.html.

The terms "nucleic acid" or "polynucleotide" are used interchangeably herein and refer to any physical string of monomer units that can be corresponded to a string of nucleotides, including a polymer of nucleotides (e.g., a typical DNA polymer or polydeoxyribonucleotide or RNA polymer or polyribonucleotide), modified oligonucleotides (e.g., oligonucleotides comprising bases that are not typical to biological RNA or DNA, such as 2'-O-methylated oligonucleotides), and the like. In some embodiments, a nucleic acid or polynucleotide can be single-stranded, double-stranded, multi-stranded, or combinations thereof. Unless otherwise indicated, a particular nucleic acid or polynucleotide of the present invention optionally comprises or encodes complementary polynucleotides, in addition to any polynucleotide explicitly indicated. The nucleic acid can be present in a vector, such as in a cell, virus or plasmid.

"Operably linked" refers to the association of polynucleotides on a single nucleic acid fragment so that the function of one affects the function of the other. For example, a promoter is operably linked with a coding polynucleotide when it is capable of affecting the expression of that coding polynucleotide (i.e., that the coding polynucleotide is under the transcriptional control of the promoter). As another example, one or more enhancers are operably linked with a promoter when the enhancer(s) are capable of affecting the binding of transcription factors to the promoter and thereby augmenting the expression of a coding polynucleotide under the transcriptional control of the promoter. Coding polynucleotide in sense or antisense orientation can be operably linked to regulatory polynucleotides. Enhancers can be operably linked to the promoter in a sense or antisense orientation.

The term "plant" refers to any plant, particularly to agronomically useful plants (e.g. seed plants), and "plant cell" is a structural and physiological unit of the plant, which comprises a cell wall but may also refer to a protoplast. The plant cell may be in form of an isolated single cell or a cultured cell, or as a part of higher organized units such as for example, a plant tissue, or a plant organ differentiated into a structure that is present at any stage of a plant's development. A plant may be a monocotyledonous or dicotyledonous plant species.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

The term "plant part," as used herein, includes but is not limited to embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, "shoot" refers to the above ground parts including the leaves and stems. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

"Plant tissue" as used herein means a group of plant cells organized into a structural and functional unit. Any tissue of a plant in planta or in culture is included. This term includes, but is not limited to, whole plants, plant organs, plant seeds, tissue culture and any group of plant cells organized into structural and/or functional units. The use of this term in conjunction with, or in the absence of, any specific type of plant tissue as listed above or otherwise embraced by this definition is not intended to be exclusive of any other type of plant tissue.

The term "promoter," as used herein, refers to a polynucleotide, usually upstream (5') of the translation start site of a coding sequence, which controls the expression of the coding sequence by providing the recognition for RNA polymerase and other factors required for proper transcription. For example, a promoter may contain a region containing basal promoter elements recognized by RNA polymerase, a region containing the 5' untranslated region (UTR) of a coding sequence, and optionally an intron. In some embodiments, a promoter comprises or consists of the about 2 kb region upstream (5') of the translation start site of a known or predicted coding sequence. In some embodiments, such as in the constructs described herein, the promoter is a minimal or core promoter comprising only those elements that are required to initiate transcription. For example, a minimal promoter may consist of a transcription start site (TSS), a binding site for RNA polymerase, and a transcription factor binding site (such as a TATA box or B recognition element). Such minimal promoter may not comprise any introns or splice sites.

"Regulatory elements" and "regulatory sequences" are used interchangeably herein and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include transcriptional enhancers, promoters, translational enhancer sequences, introns, terminators, and polyadenylation signal sequences. They include natural and synthetic sequences as well as sequences which may be a combination of synthetic and natural sequences. Regulatory sequences may determine expression level, the spatial and temporal pattern of expression and, for a subset of promoters, expression under inductive conditions (regulation by external factors such as light, temperature, chemicals and hormones). Regulatory sequences may be short regions of DNA sequence 6-100 base pairs that define the binding sites for trans-acting factors, such as transcription factors. Regulatory sequences may also be enhancers, longer regions of DNA sequence that can act from a distance from the core promoter region, sometimes over several kilobases from the core region. Regulatory sequence activity may be influenced by trans-acting factors including general transcription machinery, transcription factors and chromatin assembly factors.

A "terminator," as used herein, is responsible for the termination of transcription beyond the translation stop site of a coding sequence and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator and the pea rbcs E9 terminator. These can be used in both monocotyledons and dicotyledons. In addition, a gene's native transcription terminator may be used. For example, a terminator may contain a region containing the 3' untranslated region (UTR) of a coding sequence, and optionally additional 3' non-transcribed sequence. In some embodiments, a terminator comprises or consists of the about 1 kb region downstream (3') of the translation stop site of a known or predicted coding sequence.

A "selectable marker" or "selectable marker gene" refers to a gene whose expression in a plant cell gives the cell a selective advantage. "Positive selection" refers to a transformed cell acquiring the ability to metabolize a substrate that it previously could not use or could not use efficiently, typically by being transformed with and expressing a positive selectable marker gene. This transformed cell thereby grows out of the mass of non-transformed tissue. Positive selection can be of many types from inactive forms of plant growth regulators that are then converted to active forms by the transferred enzyme to alternative carbohydrate sources that are not utilized efficiently by the non-transformed cells, for example mannose, which then become available upon transformation with an enzyme, for example phosphomannose isomerase, that allows them to be metabolized. Non-transformed cells either grow slowly in comparison to transformed cells or not at all. Other types of selection may be due to the cells transformed with the selectable marker gene gaining the ability to grow in presence of a negative selection agent, such as an antibiotic or an herbicide, compared to the ability to grow of non-transformed cells. A selective advantage possessed by a transformed cell may also be due to the loss of a previously possessed gene in what is called "negative selection". In this, a compound is added that is toxic only to cells that did not lose a specific gene (a negative selectable marker gene) present in the parent cell (typically a transgene).

Examples of selectable markers include, but are not limited to, genes that provide resistance or tolerance to antibiotics such as kanamycin (Dekeyser et al. 1989, Plant Phys 90: 217-23), spectinomycin (Svab and Maliga 1993, Plant Mol Biol 14: 197-205), streptomycin (Maliga et al. 1988, Mol Gen Genet 214: 456-459), hygromycin B (Waldron et al. 1985, Plant Mol Biol 5: 103-108), bleomycin (Hille et al. 1986, Plant Mol Biol 7: 171-176), sulphonamides (Guerineau et al. 1990, Plant Mol Biol 15: 127-136), streptothricin (Jelenska et al. 2000, Plant Cell Rep 19: 298-303), or chloramphenicol (De Block et al. 1984, EMBO J 3: 1681-1689). Other selectable markers include genes that provide resistance or tolerance to herbicides, such as the S4 and/or Hra mutations of acetolactate synthase (ALS) that confer resistance to herbicides including sulfonylureas, imidazolinones, triazolopyrimidines, and pyrimidinyl thiobenzoates; 5-enol-pyrovyl-shikimate-3-phosphate-synthase (EPSPS) genes, including but not limited to those described in U.S. Pat. Nos. 4,940,935, 5,188,642, 5,633,435, 6,566,587, 7,674,598 (as well as all related applications) and the glyphosate N-acetyltransferase (GAT) which confers resistance to glyphosate (Castle et al. 2004, Science 304:1151-1154, and U.S. Patent Application Publication Nos. 20070004912, 20050246798, and 20050060767); BAR which confers resistance to glufosinate (see e.g., U.S. Pat. No. 5,561,236); aryloxy alkanoate dioxygenase or AAD-1, AAD-12, or AAD-13 which confer resistance to 2,4-D; genes such as *Pseudomonas* HPPD which confer HPPD resistance; Sprotophorphyrinogen oxidase (PPO) mutants and variants, which confer resistance to peroxidizing herbicides including fomesafen, acifluorfen-sodium, oxyfluorfen, lactofen, fluthiacet-methyl, saflufenacil, flumioxazin, flumiclorac-pentyl, carfentrazone-ethyl, sulfentrazone); and genes conferring resistance to dicamba, such as dicamba monoxygenase (Herman et al. 2005, J Biol Chem 280: 24759-24767 and U.S. Pat. No. 7,812,224 and related applications and patents). Other examples of selectable markers can be found in Sundar and Sakthivel (2008, J Plant Physiology 165: 1698-1716), herein incorporated by reference.

Other selection systems include using drugs, metabolite analogs, metabolic intermediates, and enzymes for positive selection or conditional positive selection of transgenic plants. Examples include, but are not limited to, a gene encoding phosphomannose isomerase (PMI) where mannose is the selection agent, or a gene encoding xylose isomerase where D-xylose is the selection agent (Haldrup et al. 1998, Plant Mol Biol 37: 287-96). Finally, other selection systems may use hormone-free medium as the selection agent. One non-limiting example the maize homeobox gene kn1, whose ectopic expression results in a 3-fold increase in transformation efficiency (Luo et al. 2006, Plant Cell Rep 25: 403-409). Examples of various selectable markers and genes encoding them are disclosed in Miki and McHugh (J Biotechnol, 2004, 107: 193-232; incorporated by reference).

In some embodiments of the disclosure, the selectable marker may be plant derived. An example of a selectable marker which can be plant derived includes, but is not limited to, 5-enolpyruvylshikimate-3-phosphate synthase (EPSPS). The enzyme 5-enolpyruvylshikimate-3-phosphate synthase (EPSPS) catalyzes an essential step in the shikimate pathway common to aromatic amino acid biosynthesis in plants. The herbicide glyphosate inhibits EPSPS, thereby killing the plant. Transgenic glyphosate-tolerant plants can be created by the introduction of a modified EPSPS transgene which is not affected by glyphosate (for example, U.S. Pat. No. 6,040,497; incorporated by reference). Other examples of a modified plant EPSPS which can be used as a selectable marker in the presence of glyphosate includes a P106L mutant of rice EPSPS (Zhou et al 2006, Plant Physiol 140: 184-195) and a P106S mutation in goosegrass EPSPS (Baerson et al 2002, Plant Physiol 129: 1265-1275). Other sources of EPSPS which are not plant derived and can be used to confer glyphosate tolerance include but are not limited to an EPSPS P101S mutant from *Salmonella typhimurium* (Comai et al 1985, Nature 317: 741-744) and a mutated version of CP4 EPSPS from *Agrobacterium* sp. Strain CP4 (Funke et al 2006, PNAS 103: 13010-13015). Although the plant EPSPS gene is nuclear, the mature enzyme is localized in the chloroplast (Mousdale and Coggins 1985, Planta 163:241-249). EPSPS is synthesized as a preprotein containing a transit peptide, and the precursor is then transported into the chloroplast stroma and proteolytically processed to yield the mature enzyme (della-Cioppa et al. 1986, PNAS 83: 6873-6877). Therefore, to create a transgenic plant which has tolerance to glyphosate, a suitably mutated version of EPSPS which correctly translocates to the chloroplast could be introduced. Such a transgenic plant then has a native, genomic EPSPS gene as well as the mutated EPSPS transgene. Glyphosate could then be used as a selection agent during the transformation and regeneration process, whereby only those plants or plant tissue that are successfully transformed with the mutated EPSPS transgene survive.

The term "transformation" as used herein refers to the transfer of a nucleic acid into a host cell, preferably resulting in genetically stable integration, which includes integration into a chromosome and heritable extrachromosomal events. In some particular embodiments, the introduction into a plant, plant part and/or plant cell is via bacterial-mediated transformation, particle bombardment transformation (also called biolistic particle transformation), calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethylene glycol-mediated transformation, protoplast transformation, or any other electrical, chemical, physical and/or biological mechanism that results in the introduction of a nucleic acid into the plant, plant part and/or cell thereof, or a combination thereof. General guides to various plant transformation methods known in the art include Miki et al. ("Procedures for Introducing Foreign DNA into Plants" in Methods in Plant Molecular Biology and Biotechnology, Glick, B. R. and Thompson, J. E., Eds. (CRC Press, Inc., Boca Raton, 1993), pages 67-88) and Rakowoczy-Trojanowska (2002, Cell Mol Biol Lett 7:849-858 (2002)).

Procedures for transforming plants are well known and routine in the art and are described throughout the literature. Non-limiting examples of methods for transformation of plants include transformation via bacterial-mediated nucleic acid delivery (e.g., via bacteria from the genus *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in Methods in *Plant Molecular Biology and Biotechnology,* Glick, B. R. and Thompson, J. E., Eds. (CRC Press, Inc., Boca Raton, 1993), pages 67-88) and Rakowoczy-Trojanowska (*Cell Mol Biol Lett* 7:849-858 (2002)).

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. 1993, *Plant Cell* 5:159-169). The transfer of the recombinant binary vector to *Agrobacterium* can be accomplished by a tri-parental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen and Willmitzer 1988, *Nucleic Acids Res* 16:9877).

Transformation of a plant by recombinant *Agrobacterium* usually involves co-cultivation of the *Agrobacterium* with explants from the plant and follows methods well known in the art. Transformed tissue is typically regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacteria or a bacteriophage, each containing one or more nucleic acids sought to be introduced) also can be propelled into plant tissue.

Thus, in particular embodiments of the present invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures,* Vol. 1, MacMilan Publishing Co. New York (1983)); and Vasil I. R. (ed.) (*Cell Culture and Somatic Cell Genetics of Plants,* Acad. Press, Orlando, Vol. I (1984), and Vol. II (1986)). Methods of selecting for transformed transgenic plants, plant cells and/or plant tissue culture are routine in the art and can be employed in the methods of the invention provided herein.

A "transgenic plant" is a plant having one or more plant cells that contain a heterologous DNA sequence.

As used herein, "vector" includes reference to a nucleic acid used in transfection of a host cell and into which can be inserted a polynucleotide. Vectors are often replicons. Expression vectors permit transcription of a nucleic acid inserted therein. "Vector" is defined to include, inter alia, any plasmid, cosmid, phage or *Agrobacterium* binary vector in double or single stranded linear or circular form which may or may not be self-transmissible or mobilizable, and which can transform prokaryotic or eukaryotic host either by integration into the cellular genome or exist extrachromosomally (e.g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

DETAILED DESCRIPTION

Aspects of the disclosure relate to regulatory elements, such as transcriptional enhancers, introns, and terminators, useful for expression of heterologous sequences in plants, such as maize.

In one embodiment, the disclosure provides a method of transiently expressing a nucleotide sequence in a plant part in planta comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part.

In one aspect, the disclosure provides a method of transiently expressing a nucleotide sequence in a plant part in planta comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part, wherein the plant part is a nascent leaf.

In another aspect, the disclosure provides a method of transiently expressing a nucleotide sequence in a plant part in planta comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part, wherein the plant is a monocot.

In another aspect, the disclosure provides a method of transiently expressing a nucleotide sequence in a plant part in planta comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part, wherein the plant is a dicot.

In another aspect, the disclosure provides a method of transiently expressing a nucleotide sequence in a plant part in planta comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part, wherein the plant is selected from the group of maize, sugarcane, and soybean.

In another aspect, the disclosure provides a method of transiently expressing a nucleotide sequence in a plant part in planta comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part, wherein the plant is 8-10 days old.

In another aspect, the disclosure provides a method of transiently expressing a nucleotide sequence in a plant part in planta comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part, wherein the wounding a plant part is performed with a needle matrix.

In another aspect, the disclosure provides a method of transiently expressing a nucleotide sequence in a plant part in planta comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part, wherein the wounding a plant part is performed with a needle matrix, wherein the needle matrix has 2 mm in spacing between each needle.

In another aspect, the disclosure provides a method of transiently expressing a nucleotide sequence in a plant part in planta comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part, wherein the wounding of a plant part is performed with a needle matrix, wherein the needle matrix has 2 mm in spacing between each needle, wherein the needle spacing produces assays with equal distances between wound sites in order to generate equal damage on leafroll to reduce assay variation.

In another aspect, the disclosure provides a method of transiently expressing a nucleotide sequence in a plant part in planta comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part, wherein the wounding of a plant part is performed with a needle matrix, wherein the needle matrix has 2 mm in spacing between each needle, wherein the needle spacing produces assays with equal distances between wound sites in order to generate equal damage on leafroll to reduce assay variation, wherein the needle matrix has 0.2 mm diameter needles.

In another aspect, the disclosure provides a method of transiently expressing a nucleotide sequence in a plant part in planta comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part, wherein *Agrobacterium*-infiltrating comprises cutting the plant above the second node and pipetting agrobacteria onto the cut site wherein the agrobacteria enter the leafroll and infect a wounded nascent leaf.

In another aspect, the disclosure provides a method of transiently expressing a nucleotide sequence in a plant part in planta comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part, wherein the coefficient of variation between samples is <35%.

In another aspect, the disclosure provides a method of transiently expressing a nucleotide sequence in a plant part in planta comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part, wherein the increased transiently expressed protein level is 3 fold higher compared the method by syringe infiltration.

In another embodiment, the disclosure provides a method to generate large amount of fresh transiently expressed tissue for bioassay or protein production comprising the steps of: a) wounding a plant part; b) *Agrobacterium*-infiltrating of an expression cassette comprising at least one nucleotide sequence operably linked to a promoter into the plant part in planta, c) transiently expressing said at least one nucleotide sequence in the plant part.

In another embodiment, the disclosure provides an expression cassette comprising two operably linked nucleotide sequences. In one aspect of the embodiment, the first nucleotide sequence is a plant transcriptional enhancer. In another aspect of this embodiment, the second nucleotide sequence is a viral transcriptional enhancer. In further aspects, the operably linked transcriptional enhancers are adjacent or contiguous to each other and the expression cassette comprises a third nucleotide sequence having at least 90% identity (e.g., at least 91%, at least 92%, at least 93%, at least 94%, at least 95%, at least 96%, at least 97%, at least 98%, at least 99%, or 100% identity) with one or more of SEQ ID NOs: 49-80. In another aspect of this embodiment, the third nucleotide sequence comprises one or more of SEQ ID NOs: 49-80. In yet another aspect, the operably linked transcriptional enhancers are separated only by one or more restriction enzyme digestion sites.

In another embodiment, the disclosure provides a nucleotide sequence that is a plant transcriptional enhancer having at least 90% identity (e.g., at least 91%, at least 92%, at least 93%, at least 94%, at least 95%, at least 96%, at least 97%, at least 98%, at least 99%, or 100% identity) with one or more of SEQ ID NOs: 1-21. In one aspect of this embodiment, the plant transcriptional enhancer comprises one or more of SEQ ID NOs: 1-21.

In another embodiment, the disclosure provides a nucleotide sequence that is a viral transcriptional enhancer having at least 90% identity (e.g., at least 91%, at least 92%, at least 93%, at least 94%, at least 95%, at least 96%, at least 97%, at least 98%, at least 99%, or 100% identity) with one or more of SEQ ID NOs: 22-48. In one aspect of this embodiment, the viral transcriptional enhancer comprises one or more of SEQ ID NOs: 22-48.

In another embodiment, the disclosure provides a plant transcriptional enhancer that is selected from the group consisting of SEQ ID NO: 18, SEQ ID NO: 19, SEQ ID NO: 8, SEQ ID NO: 11, and SEQ ID NO: 12.

In yet another embodiment, the disclosure provides a viral transcriptional enhancer that is selected from the group consisting of SEQ ID NO: 30, SEQ ID NO: 32, SEQ ID NO: 26, and SEQ ID NO: 34.

In further embodiments, the disclosure provides an expression cassette comprising two heterologous transcriptional enhancers (herein also referred to as dual transcriptional enhancer sequences) positioned contiguous to each other, wherein the dual transcriptional enhancer sequences are operably linked to an additional heterologous sequence. In one aspect of the embodiment, the additional heterologous sequence comprises a nucleotide sequence having at least 90% identity (e.g., at least 91%, at least 92%, at least 93%, at least 94%, at least 95%, at least 96%, at least 97%, at least 98%, at least 99%, or 100% identity) with one or more of SEQ ID NOs: 82-91. In another aspect of this embodiment, the heterologous sequence comprises one or more of SEQ ID NOs: 82-91.

In some other embodiments, the additional heterologous sequence comprises a nucleotide sequence having at least 90% identity (e.g., at least 91%, at least 92%, at least 93%, at least 94%, at least 95%, at least 96%, at least 97%, at least 98%, at least 99%, or 100% identity) with one or more of SEQ ID NOs: 93-100. In another aspect of this embodiment, the heterologous sequence comprises one or more of SEQ ID NOs: 93-100.

In some embodiments, the heterologous sequence is a nucleic acid of interest that encodes an RNA or protein of interest. In some embodiments, the RNA or protein of interest is capable of conferring upon a plant a desired characteristic such as antibiotic resistance, virus resistance, insect resistance, disease resistance, resistance to other pests, herbicide tolerance, improved nutritional value, improved performance in an industrial process, or altered reproductive capability.

In some embodiments, the expression cassette further comprises a selectable marker.

In some embodiments, the expression cassette is comprised within a vector, such as a plasmid, virus, or *Agrobacterium*. In other embodiments, the expression cassette is comprised within a plant cell. In some embodiments, the plant cell is a monocot cell. In some embodiments, the plant cell is a dicot cell. In some embodiments, the plant cell is a *Zea mays* cell. In some embodiments, the *Zea mays* cell is an elite *Zea mays* cell.

In some embodiments, the expression cassette is comprised within a transgenic plant. In some embodiments, the plant is a monocot. In some embodiments, the plant is a *Zea mays* plant. In some embodiments, the *Zea mays* plant is an elite *Zea mays* plant. In some embodiments, the plant is a dicot. In some embodiments, the dicot plant is a soy plant cell or a tobacco plant.

In some embodiments, the disclosure provides a seed from a transgenic plant, e.g., a seed comprising the expression cassette.

In still further embodiments, the disclosure provides for a polynucleotide comprising a chimeric enhancer sequence, wherein the chimeric enhancer sequence comprises a first plant enhancer sequence operably linked to a second viral enhancer sequence. In some aspects of this embodiment, the chimeric enhancer sequence has a higher transcriptional enhancing activity on a promoter operably linked to the chimeric enhancer sequence than either enhancer sequence alone. In some embodiments, the polynucleotide further comprises a promoter operably linked to the chimeric enhancer and a heterologous polynucleotide transcribable by the promoter, the heterologous polynucleotide encoding a gene of interest that imparts a desirable trait upon transformation. In still further embodiments, the polynucleotide further comprises a terminator operably linked to the heterologous polynucleotide.

In another embodiment, the disclosure provides for an expression cassette comprising, as operably linked components, a chimeric enhancer comprising a first plant enhancer contiguous to a second viral enhancer; a promoter; a heterologous polynucleotide transcribable by the promoter, wherein transcription of the polynucleotide by the promoter is increased by the chimeric enhancer; and optionally, a terminator. In further representations of this embodiment, the first plant enhancer sequence is a polynucleotide comprising one of SEQ ID NO: 18, SEQ ID NO: 19, SEQ ID NO: 8, SEQ ID NO: 11, and SEQ ID NO: 12; or a polynucleotide having at least 90% sequence identity to one of SEQ ID NO: 18, SEQ ID NO: 19, SEQ ID NO: 8, SEQ ID NO: 11, and SEQ ID NO: 12. In further representations of this embodiment, the second viral enhancer sequence is a polynucleotide comprising one of SEQ ID NO: 30, SEQ ID NO: 32, SEQ ID NO: 26, and SEQ ID NO: 34 or a polynucleotide having at least 90% sequence identity to or comprises one of SEQ ID NO: 30, SEQ ID NO: 32, SEQ ID NO: 26, and SEQ ID NO: 34. In further representations of this embodiment, the promoter of the expression cassette is a plant promoter that comprises SEQ ID NO: 102; or a polynucleotide having at least 90% sequence identity to SEQ ID NO: 102 or a functional fragment of SEQ ID NO: 102. In further representations of this embodiment, the optional terminator included in the expression cassette comprises SEQ ID NO: 101; or a polynucleotide having at least 90% sequence identity to SEQ ID NO: 102.

In some embodiments of the expression cassette, the heterologous polynucleotide comprises SEQ ID no: 103; or a polynucleotide encoding for a polypeptide comprising SEQ ID NO: 104; or a polynucleotide encoding for a polypeptide having at least 90% sequence identity to SEQ ID NO: 104. In further embodiments, the heterologous polynucleotide encodes a selectable marker protein such as a protein providing a visible marker (e.g., GFP, GUS etc.), a protein providing antibiotic resistance, etc.

In further embodiments, the disclosure provides for polynucleotide sequences comprising novel introns. In one example representation of such an embodiment, a recombinant DNA expression cassette comprises a promoter functioning in plants or plant cells; and an intron comprising (a) the sequence of any one of SEQ ID NOS: 82-91; (b) a polynucleotide sequence having at least 95% sequence identity to any one of SEQ ID NOS: 82-91; or (c) a functional equivalent thereof, wherein the functional equivalent confers intron mediated enhancement of transcription and/or translation of a heterologous nucleic acid driven by the promoter.

In other embodiments, the disclosure provides for polynucleotide sequences comprising novel terminators. In one example representation of such an embodiment, a recombinant DNA expression cassette comprises a promoter functioning in plants or plant cells; and a terminator comprising (a) the sequence of any one of SEQ ID NOS: 93-100; (b) a polynucleotide sequence having at least 95% sequence identity to any one of SEQ ID NOS: 93-100; or (c) a functional equivalent thereof, wherein the functional equivalent confers terminator mediated enhancement of transcription and/or translation of a heterologous nucleic acid driven by the promoter.

Other aspects of the disclosure relate to a method, e.g., a transformation method, comprising introducing an expression cassette or vector as described herein into a plant or plant cell. In some embodiments, the introducing comprises Agrobacterium-mediated transformation. In some embodiments, the introducing comprises particle bombardment. In some embodiments of the method, the method further comprises placing the plant or plant cell under conditions whereby an RNA or protein of interest and/or a selectable marker is expressed from the expression cassette or vector. In some embodiments, the conditions are appropriate growth or maintenance conditions for the plant or plant cell. In some embodiments of the method, the method further comprises crossing the plant to a second plant to produce a progeny plant. In some embodiments, the plant or plant cell is a monocot plant or plant cell. In some embodiments, the plant or plant cell is a Zea mays plant or plant cell. In some embodiments, the plant or plant cell is an elite Zea mays plant or plant cell. In some embodiments, the second plant in an elite Zea mays plant.

In some embodiments, a method of evaluating gene expression in a nascent leaf comprising the steps of transforming the expression construct into Agrobacterium, cutting a nine day old Maize plant above the second node and removing leaves, wounding the stem with a needle matrix, wherein a nascent leaf inside the stem is also wounded, infiltrating the transformed Agrobacterium into the wounded stem, harvesting the nascent leaf to evaluate gene expression is provided.

Hereinafter, the present invention will be described in detail by the following examples. However, the following examples are illustrative of the present invention, and the scope of the present invention is not limited by the following examples.

EXAMPLES

Example 1: Identification of Novel Enhancer Sequences

Enhancers were selected from both maize and plant viruses for evaluation in the study. A report by Oka, et al. (2017) describing the identification of enhancer candidates in maize was mined for potential elements. In the report, data was obtained from two maize tissues, namely husk leaves and V2 stage inner stem tissue. The data generated included ChIPSeq data obtained from antibodies to H3K9ac (shown to be a mark of active enhancers in plants), DNAse-seq data, methylation data from bisulfate sequencing, and RNAseq data to profile gene expression in the two tissues. Targets were identified as genes 5 kb upstream or downstream of the candidate enhancers where a single gene in closest proximity in either direction was nominated as the target for a given enhancer. Genic and intergenic regions of the genome were categorized to distinguish transcriptional enhancer elements ("enhancers") from promoters, exons, introns (including putative enhancer elements present within introns), flanking and distal intergenic regions, and terminators. Enhancers in close proximity to genes more highly expressed in either tissue were considered tissue specific; genes that were expressed significantly but not statistically different were considered to be constitutively expressed. The present disclosure focused on candidate enhancer sequences that were considered to be constitutively expressed, as they were deemed to be potentially more valuable to Insect Control trait gene expression. 221 candidate enhancer elements identified upstream of annotated genes were examined further. The genes were all named using accession IDs from the publicly available Maize genome, specifically, genome version B73 RefGen_v4, AGPv4) sourced from the website: https://www.maizegdb.org/. Gene expression profiles of all the genes found downstream of the constitutive enhancer candidates were examined using over 3500 samples (corresponding to 80+ tissue types) found in an internal installation of Genevestigator. The internal installation of Genevestigator included both publicly available data as well as proprietary Syngenta data. Data were first sorted by developmental stage to find genes expressed moderately to highly in most developmental stages (e.g., genes in the top quartile of all gene expression values across all samples in the local Genevestigator installation). Next, a subset of expressed genes was examined across tissue types. Data were also obtained for the ubiquitin gene Zm00001d015327 as a reference comparison. None of the assessed genes coupled downstream of the tested enhancer candidates had expression levels as high as ubiquitin, nor expressed as strongly in as many tissues as ubiquitin.

A second study was conducted to identify introns that might help drive and stabilize transgene expression. As part of that study, genes were ranked by low variance and high expression across 63 tissues from a Syngenta maize inbred line, an internal study, and by high protein expression from a subset of the same tissue samples. A list of the top 100 candidate genes was used. In total, 22 enhancer candidates were identified, including one downstream of a gene highly expressed in green tissue, one upstream of a gene highly expressed with low variance in 63 tissues from the Syngenta maize inbred line, one with high expression is silk tissue, and 19 genes with moderate to high expression in 75 tissues.

Sequences of viral genomes that contain promoters were selected for enhancer discovery. Experimentally defined enhancer elements from plant viral promoters have been identified in sequences within a few hundred nucleotides upstream of the conserved TATA box upstream of the transcriptional start site. The viral genomes examined were Chlorella virus (CviBIII, Mitra and Higgens (1994), Cestrum yellow leaf curling virus (CmYLCV, Stavolone et al 2003), Figwort Mosaic Virus (FMV Richins et al 1987), Cassava vein mosaic virus (CsVMV, Verdaguer et al 1996), Mirabilis mosaic virus (MiMV, Dey and Maiti 1999), Peanut chlorotic streak virus (PCISV, Maiti and Shepherd (1998), Rice Tungro bacilliform virus (RTBV, Hay et al 1991), and two strains of sugar cane bacilliform virus (ScBV Bouhida et al 1993; ScBv IM, Davies et al 2014), Blueberry Ringspot Virus (BRRV; Glasheen, et al 2002), Carnation etched ring virus (CERV; Hull et al 1986), Commelina Yellow Mottle Virus (CoYMV; Medberry, et al 1992), Dahlia Common Mosaic Virus (DCMV, Banerjee, 2015), Maize Streak Virus (MSV, Martin et al), Milk Vetch Dwarf Virus (MVDV, Shirasawa-Seo, et al 2005). The software tool NSITE (Shahmuradov I., Solovyev V. (2015) Nsite, NsiteH and NsiteM Computer Tools for Studying Transcription Regulatory Elements. Bioinformatics, doi: 10.1093ref) was used to identify potential regulatory elements (RE) within the sequences using default parameters. A total of 26 potential enhancer elements were identified from the viral sources.

Example 2: Construction of Recombinant DNA Expression Cassettes Comprising Chimeric Enhancer Sequences Recombinant DNA expression cassettes comprising one or more enhancer sequences, including the novel enhancer sequences described above were constructed using a combination of methods well known to those skilled in the art such as overlap PCR, DNA synthesis, restriction fragment sub-cloning and ligation. Multiple expression cassettes were constructed wherein each expression cassette comprised multiple operably linked components. The operably linked components included an enhancer element either in the form for of an individual enhancer (plant or viral, novel or known), or in the form of chimeric enhancers (herein provided as dual enhancers). The chimeric enhancers comprised a first plant enhancer contiguous to a second viral enhancer with the plant enhancer positioned upstream of the viral enhancer in some expression cassettes, and the viral enhancer positioned upstream of the plant enhancer in other expression cassettes. The individual or chimeric enhancer was operably linked to a plant promoter, which was operably linked to a heterologous polynucleotide transcribable by the promoter. In some constructs, the plant promoter was a constitutive plant promoter. In other constructs, the plant promoter was a tissue-specific plant promoter configured to drive expression of the operably linked to a heterologous polynucleotide in a tissue-specific manner. The cassette further comprised a terminator. As a result of the operably linked components, it was expected that transcription of the polynucleotide by the promoter would be increased by the chimeric enhancer in the expression cassette.

Control constructs were also created comprising chimeric enhancers having, for example, a first and second viral enhancer, a first and a second plant enhancer, or a first known plant enhancer coupled to a known viral enhancer, wherein the known plant enhancer and the known viral enhancer were enhancers whose expression profile from the given promoter was previously studied and known.

An example design of a generic construct comprising the chimeric enhancer elements of the present disclosure is described below. The example constructs comprise the chimeric enhancers of the present disclosure in an expression cassette operably linked to a promoter (which, in one example, is a plant promoter, such as Maize Ubi1 promoter or Maize 393 promoter). The construct further comprises, operably linked to the chimeric enhancer, an optional intron, a gene of interest (such as a maize optimized truncated version of Cry1Ab), and a terminator (for example Nos promoter). It will be appreciated that while the chimeric enhancer of FIG. 1 shows a plant enhancer element upstream of a viral enhancer element, this arrangement is not meant to be limiting and that in other constructs, the viral enhancer may be positioned upstream of the plant enhancer without departing from the scope of the invention.

Constructs generated using plant viral enhancers were pre-screened in a corn leaf transient assay (as described below) to determine their level of expression (data shown in Table 1). Those enhancers which improved expression levels in the pre-screening were selected to be further evaluated in combination with the newly identified plant transcriptional enhancers. The selection of plant transcriptional enhancers was random, but preferentially selected those that were smaller in length (<1 Kb).

Vectors were designed for individual or double candidate enhancer sequences, each of which contained a maize ubiquitin-1 promoter driving a truncated, maize optimized Cry1Ab gene, and the Nos terminator sequence. The truncated insect control gene Cry1Ab was used to evaluate all the enhancer elements of the present disclosure. For cloning convenience, enhancer sequences were synthesized as fragments flanked with SanDI (KflI) and Acc65I restriction sites; these restriction sites were removed from other elements within the construct if present. Components of the double or chimeric enhancers were separated by a XhoI restriction site inserted between individual enhancers for cloning purposes.

The unique structures of the constructs are made explicit through the example of vector 25356.

It will be appreciated that while the constructs described above contain a maize ubiquitin-1 promoter, this is not meant to be limiting, and that similar constructs having similar or higher expression profiles may be generated using other promoters, such as other plant promoters as well as viral promoters, and other heterologous promoters. Likewise, while the constructs are used to describe the transcription enhancing effect of the chimeric enhancers on Cry1Ab, in other constructs, the chimeric enhancers may be similarly used to augment the transcription of an alternate gene of interest imparting a desired characteristic on a plant transformed with the construct.

Example 3: Characterization of Constructs Comprising Chimeric Enhancer Sequences Methods Vectors comprising the enhancer sequences were initially screened by transient transformation. Expression levels of all vectors were compared to average expression levels of a reference vector comprising a baseline positive control dual viral enhancer (eFMV+e35S, SEQ ID NO: 81). All vectors containing enhancer sequences were transformed into *Agrobacterium tumefaciens* strain EHA101 using Multi-well Electroporation 96 well format (www.harvardapparatus.com). Transformed *Agrobacterium* was grown for the in-planta corn leaf transient assay as described by Azhakanandam et al., (2007). In planta corn transient assay was performed with modification as described by Azhakanandam (U.S. Pat. No. 8,642,839: Method for the transient expression of nucleic acids in plants). Transient transformation was performed using 9-day old maize plants. Plants were cut off above the second node and damaged using a wire brush. Three plants were infiltrated per test construct. One milliliter of *Agrobacterium* suspension containing the test construct in addition to an internal control construct at a 1:1 ratio was pipetted on the top of the damaged stem tissue. Each *Agrobacterium* was adjusted to OD=1.0 at 600 nm. The infected plants were placed into a growth chamber for 3-4 days after which the infiltrated leaves were harvested in a 96 well block for a quantitative sandwich ELISA assay. A maximum of 8 data points was collected per construct based on the available tissue. The ELISA employed a monoclonal and a polyclonal antibody which had been produced against the Cry1Ab protein. High-binding polystyrene plates (Nunc Maxisorp #430341) were coated at 4° C. overnight with 1 ug/ml anti-Cry1Ab MAb in 25 mM borate, 75 mM NaCl, pH 8.5. Plates were washed five times with Phosphate Buffered Saline+0.05% Tween-20 (PBST). Standards (80, 40, 20, 10, 5, 2.5, 1.25 and 0 ng/ml of purified Cry1Ab protein) were prepared in ELISA diluent. One hundred microliters of each appropriately diluted sample or standard was added to the plate, incubated for 1 hr at ambient temperature with shaking at 200 rpm, and washed five times. Rabbit anti-Cry1Ab serum (100 ul/well) diluted 1/50,000 in ELISA diluent was then added to the plate, incubated for 1 hour at ambient temperature with shaking at 200 rpm, and washed as before. Donkey anti-rabbit serum conjugated to alkaline phosphatase (Jackson ImmunoResearch, West Grove, PA) at 1 ug/ml in ELISA diluent was added to the plate (100 ul/well), incubated at ambient temperature with shaking at 200 rpm, and washed. Substrate p-nitrophenyl phosphate (Surmodics, Eden Prairie, MN) was added and allowed to develop for 15-30 min at ambient temperature. The absorbance was measured at 405 nm using a microplate reader (BioTek Powerwave XS2, Winooski, VT). The standard curve used a four-parameter curve fit to plot the concentrations versus the absorbance. To normalize for extraction efficiency, the concentration of the analyte (Cry1Ab) was divided by the concentration of the total soluble protein (TSP). TSP was measured using the Pierce™ BCA (bicinchoninic acid) protein assay (ThermoFisher Scientific).

Results 80 vectors correspondingly comprising 80 different enhancer sequences were tested in a transient transformation assay. Of these 80 vectors, 48 vectors contained single enhancers (SEQ ID NOs: 1-48) and 32 contained dual enhancers (SEQ ID NOs: 49-80). Of the 80 tested vectors, 23 were found to have expression levels comparable to or higher than the positive control (eFMV+e35S, SEQ ID NO: 81) comprising dual enhancers (Table 1). The majority of tested expression cassettes exhibiting expression levels higher than the positive control were those containing dual enhancers. Three viral enhancers eMMV (SEQ ID NO: 30), eCsVMV (SEQ ID NO: 26), and ePCISV (SEQ ID NO: 32), were present in dual enhancer combinations in most of the constructs exhibiting highest expression levels.

Expression cassettes were ranked based on their expression levels relative to the baseline positive cassette. The top performing cassettes were selected for further experiments using stable transformants (Table 2). As seen in the table, the dual transcriptional enhancer combination of plant enhancer eZm18 and viral enhancer eMMV (construct 25356) more than doubled the expression level of truncated Cry1Ab in leaf tissue relative to the positive control cassette (construct 25078). This result is unexpected due to the lower expression levels observed with the corresponding individual plant and viral enhancers (constructs 25370 and 25491). Additionally, expression cassettes comprising chimeric enhancers having other combinations of plant and viral enhancers, such as constructs with the combination of plant enhancer eZm19 and viral enhancer ePCISV (construct 25361), and plant enhancer eZm18-n1 and viral enhancer eMMV-n1 (construct 25356), exhibited expression levels which exceeded that of the dual enhancer positive control construct (25078).

TABLE 1

Enhancer transient transformation expression assay results

| Enhancer Name | Enhancer SEQ ID NO | Avg Cry1Ab/ CFP | % of 25078 |
|---|---|---|---|
| eZm00001d052734 (eZm18): eMMV | 77 | 189.1 | 195% |
| eCmYLCV: ePCISV | 58 | 179.1 | 185% |
| eMMV: eScBV | 56 | 166.2 | 172% |
| eZm00001d002338 (eZm1): eMMV | 67 | 161.7 | 167% |
| ePCISV: eCsVMV | 62 | 158.7 | 164% |
| eMMV: eCsVMV | 57 | 158.1 | 163% |
| eCsVMV: eMMV | 52 | 157.2 | 162% |
| eZm00001d053090 (eZm19): ePCISV | 79 | 153.7 | 159% |
| eZm00001d015463 (eZm22): eCmYLCV | 78 | 148.3 | 153% |
| eCsVMV | 26 | 142.2 | 147% |
| eCmYLCV: eScBV | 59 | 133.3 | 138% |
| eCvi: eCsVMV | 54 | 130.7 | 135% |
| eZm00001d041480 (eZm14): eCsVMV | 75 | 125.1 | 129% |
| ePCISV: eScBV | 61 | 125.1 | 129% |
| eCsVMV: eScBV | 51 | 125.0 | 129% |
| eFMVsg: ePCISV | 64 | 123.7 | 128% |
| eZm00001d005179 (eZm3): eMMV | 68 | 123.6 | 128% |
| ePCISV | 32 | 121.3 | 125% |
| eZm00001d030618 (eZm8): eScBV | 70 | 112.2 | 116% |
| ePCISV: eCvi | 63 | 111.6 | 115% |
| eFMV | 28 | 106.6 | 110% |
| eMMV: eNOS | 55 | 102.6 | 106% |
| eZm00001d002338 (eZm1): eCsVMV | 65 | 98.4 | 102% |
| eFMV: e35s (positive control) | | 165.1 | 100% |
| eFMV: e35s (positive control) | | 96.7 | 100% |
| eCmYLCV: eCvi | 60 | 95.6 | 99% |
| eCsVMV: eNOS | 50 | 91.4 | 95% |
| eZm00001d017850 (eZm5): eScBV | 72 | 89.0 | 92% |
| eZm00001d050403 (eZm21): eScBV | 80 | 84.1 | 87% |
| eScBV | 34 | 83.2 | 86% |
| eCsVMV: eZm00001d002338 (eZm1) | 66 | 77.0 | 80% |
| eMMV | 30 | 76.6 | 79% |
| eScBV: eZm00001d030618 (eZm8) | 71 | 75.6 | 78% |
| e35S: eFMV | 49 | 70.1 | 72% |
| eCmYLCV | 31 | 69.1 | 71% |
| eScBVIM | 35 | 65.4 | 68% |
| eMMV: eZm00001d005179 (eZm3) | 69 | 64.2 | 66% |
| e35S | 25 | 56.7 | 59% |
| eFMV | 24 | 28.9 | 30% |
| eZm00001d035657(eZm11): eFMV | 74 | 23.1 | 24% |
| eFMVsg | 29 | 17.9 | 18% |
| eZm00001d035657 (eZm11) | 11 | 28.3 | 17% |
| eMDV | 48 | 27.8 | 17% |
| eCERV-L | 38 | 24.9 | 15% |
| eNOS | 23 | 14.3 | 15% |
| eDCMV_p2 | 40 | 22.9 | 14% |
| eZm00001d035693 (eZm12) | 12 | 19.5 | 12% |
| eZm00001d005179 (eZm3) | 3 | 17.8 | 11% |
| 25189 baseline without enhancers | | 11.3 | 7% |
| eCoYMV | 39 | 9.4 | 6% |
| eZm00001d034223 (eZm9) | 9 | 7.1 | 4% |
| eZm15: eCvi | 76 | 4.1 | 4% |
| eZm00001d045635 (eZm15) | 15 | 5.2 | 3% |
| eCvi: eNOS | 53 | 2.9 | 3% |
| eZm00001d030618 (eZm8) | 8 | 4.3 | 3% |
| eMSV6 | 46 | 4.1 | 2% |
| eMSV3 | 43 | 3.9 | 2% |
| eCERV-s | 37 | 3.8 | 2% |
| eMSV5 | 45 | 2.4 | 1% |
| eRTBV | 33 | 1.3 | 1% |
| eMSV7 | 47 | 2.2 | 1% |
| eZm00001d004841 (eZm2) | 2 | 2.1 | 1% |
| eZm00001d015463 (eZm22) | 22 | 1.8 | 1% |
| eCvi | 27 | 1.0 | 1% |
| eMSV1 | 41 | 1.6 | 1% |
| eZm7: eNOS | 73 | 0.8 | 1% |
| eZm00001d017850 (eZm5) | 5 | 1.3 | 1% |
| eMSV4 | 44 | 1.1 | 1% |
| eZm00001d002338 (eZm1) | 1 | 0.0 | 0% |

TABLE 1-continued

Enhancer transient transformation expression assay results

| Enhancer Name | Enhancer SEQ ID NO | Avg Cry1Ab/CFP | % of 25078 |
|---|---|---|---|
| eZm00001d005798 (eZm4) | 4 | 0.0 | 0% |
| eZm00001d020804 (eZm6) | 6 | 0.0 | 0% |
| eZm00001d029426 (eZm7) | 7 | 0.0 | 0% |
| eZm00001d034223 (eZm10) | 10 | 0.0 | 0% |
| eZm00001d039526 (eZm13) | 13 | 0.0 | 0% |
| eZm00001d041480 (eZm14) | 14 | 0.0 | 0% |
| eZm00001d046472 (eZm16) | 16 | 0.0 | 0% |
| eZm00001d048707 (eZm17) | 17 | 0.0 | 0% |
| eZm00001d052734 (eZm18) | 18 | 0.0 | 0% |
| eZm00001d053090 (eZm19) | 19 | 0.0 | 0% |
| eMSV8 | 20 | 0.0 | 0% |
| eZm00001d050403 (eZm21) | 21 | 0.0 | 0% |
| eBBRV | 36 | 0.0 | 0% |
| eMSV2 | 42 | 0.0 | 0% |

TABLE 2

Enhancer stable transformation assay results (T0 events V2 stage leaf tissue)

| Construct ID | Cassette | # of single copy events | Cry1Ab ng/mg (TSP) Low-High | Average | Median | X-fold increase over enhancer-less construct |
|---|---|---|---|---|---|---|
| 25356 | 1. eZm18-n1, eMMV-n1, prZm061393-01, cCry1Ab-09, tZm061393-01 | 10 | 526-967 | 792 | 781 | 205 |
| 25365 | ePCISV-n1, prZm061393-01, cCry1Ab-09, tZm061393-01 | 10 | 235-714 | 541 | 498 | 131 |
| 25361 | eZm19-n1, ePCISV-n1, prZm061393-01, cCry1Ab-09, tZm061393-01 | 10 | 203-470 | 328 | 354 | 93 |
| 25370 | eMMV-n1, prZm061393-01, cCry1Ab-09, tZm061393-01 | 10 | 137-464 | 342 | 326 | 86 |
| 25362 | eCsVMV-n1, eMMV-n1, prZm061393-01, cCry1Ab-09, tZm061393-01 | 10 | 144-574 | 351 | 312 | 82 |
| 25078 (positive control) | eFMV-06, e355-11, prZm061393-01, cCry1Ab-09, tZm061393-01 | 7 | 4-471 | 224 | 284 | 75 |
| 25368 | eZm8-n1, eScBV-n2, prZm061393-01, cCry1Ab-09, tZm061393-01 | 10 | 94-654 | 287 | 259 | 68 |
| 25369 | eScBV-n2, prZm061393-01, cCry1Ab-09, tZm061393-01 | 7 | 146-1442 | 412 | 248 | 65 |
| 25366 | eCsVMV-n1, prZm061393-01, cCry1Ab-09, tZm061393-01 | 8 | 127-231 | 179 | 173 | 46 |
| 25367 | eFMV-06, prZm061393-01, cCry1Ab-09, tZm061393-01 | 10 | 63-151 | 101 | 99 | 26 |
| 25491 | eZm18-n2, prZm061393-01, cCry1Ab-09, tZm061393-01 | 14 | 2.4-18 | 6 | 4.4 | 1.1 |
| 25189 (base promoter with no enhancers) | prZm061393-01, cCry1Ab-09, tZm061393-01 | 10 | 1.4-7.7 | 3.6 | 3.8 | 1 |

Example 4: Characterization of Tissue-Specific Expression of Constructs Comprising Chimeric Enhancer Sequences Expression of trCry1Ab was evaluated for tissue specificity in the events comprising expression cassettes described in Example 3. Additional samples were collected at V8 stage from tissue types including root, silk, husk, pollen, and kernel and assayed via ELISA (Table 3). Surprisingly, the constructs with chimeric enhancers maintained low expression of trCry1Ab in pollen, despite higher expression in other tissues such as leaf, root, and husk. In the majority of constructs the expression levels in pollen were lower than that of construct 25189 with no enhancer element.

TABLE 3

Tissue specific expression analysis for maize events comprising enhancer expression cassettes

| | | An average Cry1Ab ng/mg (TSP) in T0 single copy events | | | | | |
|---|---|---|---|---|---|---|---|
| Construct ID | Enhancers | Leaf 10 | Root 8 | Silk 10 | Husk 10 | Pollen 9 | Kernel 20 |
| 25189 | No enhancer | 3.61 | 37.10 | 1.51 | 23.48 | 1.52 | 907.65 |
| 25078 | eFMV + 35S | 224.79 | 562.21 | 75.50 | 393.04 | 0.53 | 177.45 |
| 25356 | eZm18 + eMMV | 792.98 | 754.46 | 374.55 | 902.78 | 1.39 | 355.44 |
| 25361 | eZm19 + ePCISV | 328.94 | 1142.31 | 221.51 | 646.17 | 0.88 | 666.97 |
| 25368 | eZm8 + eScBV | 287.98 | 660.32 | 67.21 | 486.41 | 5.57 | 139.51 |
| 25367 | eFMV-06 | 101.08 | 162.76 | 46.43 | 220.96 | 0.51 | 1208.04 |
| 25370 | eMMV | 342.92 | 771.21 | 335.08 | 558.39 | 0.98 | 338.58 |
| 25365 | ePCISV | 541.21 | 1151.53 | 366.84 | 531.14 | 1.24 | 429.32 |
| 25369 | eScBV | 412.73 | 1623.68 | 158.96 | 1283.01 | 27.04 | 2312.07 |
| 25368 | eZm8 | 289 | 660 | 67 | 86 | 5.5 | 139 |
| 25489 | eZm11 | 6 | 73 | 7 | 37 | 8.8 | 153 |
| 25490 | eZm12 | 7.3 | 74 | NA | 29 | 23 | 161 |
| 25491 | eZm18 | 6.3 | 35 | 4.2 | 34 | 1.8 | 221 |
| 25492 | eZm19 | 5 | 38 | 4.6 | 23 | 8.5 | 247 |

Example 5: Identification and Characterization of Novel Intron Sequences

Methods

Candidate intron sequences were selected based on potential to enhance gene expression. First, genes with relatively high stable expression across various tissues and conditions were selected from available transcript and proteomics data. Transcript level data was analyzed to identify gene isoforms with high, stable expression across all samples tested (data not shown). Genes with high transcript expression were then filtered using maize proteomics data from multiple tissues. The top 50 most abundant proteins were selected. The first introns for 44 of the genes were analyzed using IMEter v2.1 (http://korflab.ucdavis.edu/cgi-bin/IMEter_2014/web-imeter2.1.pl). Ten introns were selected based on high transcript, high protein, and highest IMEter scores. Introns iBdUbi10, iBdEF1a (Coussens, et al 2012) and iPvUbi1 (Mann, et al 2011) were selected based on strong constitutive activities of their corresponding promoters and the prediction that they would have the same enhancing capabilities as iUbi1 (positive control). Intron sequences were annotated from their promoter sequences provided by reference papers. iZmABP3, iZm061393, and iZm009722 were identified from internally tested plant promoters, with annotation checked/confirmed by Persephone. iZmHSP70 was identified based on its use in the art for multiple events (Mann et al 2011). iUbi1-V31 is a truncated version of the positive control iUbi1 that displayed an enhanced effect. Both introns iZmGRMZM2G149768 and iZmGRMZM2G088088 were identified using bioinformatics.

Vectors were designed for individual intron sequences, each of which contained a maize ubiquitin-1 promoter driving a truncated, maize optimized Cry1Ab gene, and the Nos terminator sequence. The truncated insect control gene Cry1Ab was used to evaluate all the elements in the invention. Intron sequences, often with short flanking promoter sequences on both ends to ensure proper splicing, were synthesized as fragments flanked with AvrII and NcoI sites for cloning convenience. These restriction sites were removed from other tested elements within the construct if present.

The vectors were then stably transformed into maize plants, validated at T0 events, and compared to control events. A. tumefaciens strain LBA4404 (pAL4404, pVGW7) was used for maize transformation. Detailed information about the pAL4404 and pVGW7 helper plasmid and the virulence region is described by Imayama et al (U.S. Pat. No. 10,266,835), Ishida et al. (Nat. Biotechnol., 1996, 14:745-750) and Negrotto et al. (Plant Cell Rep., 2000, 19:798-803). A. tumefaciens strains containing the binary vectors containing all test constructs were prepared as described by Li et al. (Plant Physiol., 2003, 133:736-47). For maize transformation, immature embryos from greenhouse grown maize inbred line NP2222 were used as explants (Zhong, et al., 2018, Methods Mol. Biol., 1676:41-59). Immature embryo isolation, Agrobacterium inoculation and co-cultivation of Agrobacterium with the immature embryos were performed as described by Li et al. (reference incorporated above) with modifications (Sivamani, et al., 2019, Mol. Biol. Rep., 46:3009-3017) Transformed tissues and putative transgenic events were generated on media using mannose selection as described earlier.

Cultivation of maize inbred NP2222 occurred in the greenhouse to generate immature embryos for transformation. Seeds were sown in pots containing Fafard® Redi-Earth media. Two-week old seedlings are transplanted to 3-gallon pots with Fafard® 3 media. Stock plants were grown in 14-hour photoperiod at 27° C. day/21° C. night and irrigated systematically with fertilizer water. Emerged ear shoots were covered with pollination bags to prevent contamination. Controlled pollinations were carried out manually and immature ears with developing kernels were harvested at 9-10 days after pollination for immature embryo extraction.

Events were generated through transformation and returned to the greenhouse when rooted in an agar media. Plantlets were transferred to pots with Fafard® Redi-Earth media for 10 to 14 days. Plantlets were sampled for Taqman copy number analysis and ELISA analysis (Example 1) prior to transplantation. Specifically, real-time PCR was set up in 384-well plates. Reactions were multiplexed to simultaneously amplify the target gene and endogenous control gene. For each sample, the Taqman Assay was setup by combining 3 μl of extracted genomic DNA with 3 μl master mix containing Jumpstart Taq ReadyMix (Sigma) supplemented with primers to a final concentration of 300 nM each and probes to a final concentration of 100 nM each. The 384-well plates were heat sealed, and the real-time PCR was carried out in either the ABI 7900 Real-time PCR machine or the Life Technologies Quant Studio Flex 7 instrument, using the following parameters: 95° C. for 5 minutes, 40 cycles of 95° C. for 5 seconds and 60° C. for 30 seconds. Post-run data analysis was performed according to the manufacturer's instructions. Single copy events were transplanted to 3-gallon pots with Fafard® 3 media, maintained in 14-hour photoperiod at 27° C. day/21° C. night and irrigated systematically with fertilizer water. During the vegetative life cycle, leaf tissue and reproductive tissues were collected at various timepoints for ELISA protein expression analysis as described in Example 1. During reproductive stage, silk and pollen were collected and stored at −80° C. until sample plates were prepared for lab delivery. Events were self-pollinated and/or outcrossed to a tester inbred to create T1/F1 hybrids for further expression analysis.

Results 10 vectors containing 10 different candidate introns were tested in stable maize transformants. The data revealed that the intron-mediated enhancement is more prominent for some introns than others. For example, iBdUbi10-v2 enhanced expression 4× more compared with iZmGRMZM2G088088. Of those 10 introns tested, 4 expression cassettes were found to have expression levels of truncated Cry1Ab that were comparable or better in stable transformants than the cassette containing positive control intron iUbi1-30, which is one of the strongest enhancing introns as currently reported in the literature (SEQ ID NO: 92) (Table 4).

TABLE 4

Expression of reporter, cCry1Ab-09, in leaf tissue

| Genie ID | Cassette details | Average ELISA (ng/mg TSP) |
|---|---|---|
| 24832 | prUbi1-44, iBdUbi10-v2, cCry1Ab-09, tNOS-05-01 | 568 |
| 24833 | prUbi1-44, iBdEF1a-v1, cCry1Ab-09, tNOS-05-01 | 337 |
| 24835 | prUbi1-44, iUbi1-v31, cCry1Ab-09, tNOS-05-01 | 312 |
| 24838 | prUbi1-44, iPvUbi1, cCry1Ab-09, tNOS-05-01 | 302 |
| 24310 (Positive control) | prUbi1-44, iUbi1-30, cCry1Ab-09, tNOS-05-01 | 277 |
| 24834 | prUbi1-44, iZmABP3-02, cCry1Ab-09, tNOS-05-01 | 220 |
| 24837 | prUbi1-44, iZmGRMZM2G149768, cCry1Ab-09, tNOS-05-01 | 197 |
| 24839 | prUbi1-44, iZm061393-v3, cCry1Ab-09, tNOS-05-01 | 136 |
| 24836 | prUbi1-44, iZm009722-01, cCry1Ab-09, tNOS-05-01 | 128 |
| 24846 | prUbi1-44, iZmHSP70-V2, cCry1Ab-09, tNOS-05-01 | 127 |
| 24840 | prUbi1-44, iZmGRMZM2G088088, cCry1Ab-09, tNOS-05-01 | 112 |

Example 6: Identification and Characterization of Novel Terminator Sequences

Methods

Candidate terminator sequences were selected from internal data as well as from literature which were used for overexpression of different proteins in monocots. tSoUbi4 (Wei et al 2003), tBdEF1a (Coussens et al 2012), tOsAct1 (McElroy et al 1990), tOsRubiq2 (Wang et al 2000), and tPvUbi1 (Mann et al 2011) were selected based on strong constitutive expression of their associated genes and the assumption that they contributed to the expression levels. The sequences were selected based on annotation of their corresponding gene models in their specific genomes. tZmUGTBx9 and tZmABP1 were also selected based on their performance when evaluated with internally identified genes.

Vectors were designed for individual terminator sequences, each of which contained a maize ubiquitin-1 promoter driving a truncated, maize optimized Cry1Ab gene, and the unique terminator sequence. The truncated insect control gene Cry1Ab was used to evaluate all the elements in the invention. Terminator sequences were synthesized as fragments flanked with SacI and RsrII sites for cloning convenience; these restriction sites were removed from other tested elements within the construct if present.

The vectors were then stably transformed into maize plants, validated at T0 events, and compared to control events. The transformation and analysis methods are the same as those described in Example 2.

Results 8 vectors containing 8 different candidate terminators were tested in a stable maize transformants. The data revealed that the terminator-mediated enhancement is prominent for most of the terminators tested. Terminator-mediated enhancement was at a maximum 6-fold increase with tOsRubiq2. Of those 8, 6 expression cassettes were found to have expression levels of truncated Cry1Ab comparable or better in stable transformants than the cassette containing the positive control terminator tNos-05-01 (SEQ ID NO: 101) (Table 5).

TABLE 5

Expression of reporter, cCry1Ab-09, in leaf tissue

| Genie ID | Cassette details | Average T0 expression ng/mg (TSP) |
|---|---|---|
| 24824 | prUbi1-44, cCry1Ab-09, tOsRubiq2 | 842 |
| 24826 | prUbi1-44, cCry1Ab-09, tZmABP-01 | 779 |
| 24827 | prUbi1-44, cCry1Ab-09, tZmUGTBx9 | 480 |
| 24825 | prUbi1-44, cCry1Ab-09, tPvUbi1 | 404 |
| 24831 | prUbi1-44, cCry1Ab-09, tOsAct1-V1 | 368 |
| 24830 | prUbi1-44, cCry1Ab-09, tUbi1-04 | 322 |
| 24310 (positive control) | prUbi1-44, cCry1Ab-09, tNOS-05-01 | 277 |
| 24823 | prUbi1-44, cCry1Ab-09, tSoUbi4 | 242 |
| 24822 | prUbi1-44, cCry1Ab-09, tBdEF1a | 131 |

Example 7 Maize In-Planta Transient System

Prepare *Agrobacterium* containing a binary vector containing an expression cassette for s gene of interest. Cut off top of maize plant (8-12 days after germination) from the second extended leaf. Cut off the bottom leaf as well. Only the stem is remaining. 7.5.2

Treat the maize stem with a wire brush and a wood board by pushing the wire brush against the wood board; make sure the wires go through maize stem. Release the wire brush gently, avoiding severe damage to maize stem.

Option 1. Infiltration by pipetting Agrobacteria from top of the stem: Take 1 mL of infiltration medium with 1 mL fresh tip, gently apply the Agrobacteria from the top of stem with pipetting force. Infiltration media will leak through the tiny holes created by wire brush damage. This will be enough for infiltration, change new tip for infiltration of the second plant. Make sure to pipette up and down several times to mix when taking from infiltration medium.

Option 2. Infiltration by Dipping: Cover the pot with a 3-D printed lid or similar device in order to avoid soil contamination of the infiltration medium. Immerse the treated stem into the infiltration medium containing the bacterial suspension for 10 seconds while swirling the stem in the bacterial suspension.
Option 3. Vacuum infiltration: this method will only be conducted when higher expression level of protein is desired. Cover the pot with a 3-D printed lid or similar device in order to avoid soil contamination of the infiltration medium. Immerse the treated stem into the infiltration medium containing the bacterial suspension under vacuum condition for 10 seconds.
Place the infiltrated plants in a tray and maintain in the growth chamber around 25° C. with a photoperiod of 16 h light and 8 h dark for 4 days (based on the objectives, harvesting time may be extended). Monitor plants in the growth chamber (maintain proper water supply for plant needs, void of any insects/bugs in the chamber). Harvest only the tissue which shows clear wire damage of the new leaf in 96 well blocks and submit for ELISA, qRT-PCR or other analysis.

Example 8 Sugarcane In-Planta Transient Expression System

Prepare *Agrobacterium* containing a binary vector containing an expression cassette for genes of interest. Remove all the leaves from sugarcane plants. Press wire brush against a wood board and push through the plant stem. This will create minor damages on meristem, short tip Apex and leaf roll inside the stem. 4.4 Vacuum infiltration conditions for sugarcane: Cover the pot with 3D lid, secure it with tape and dip wire brush treated stem into agro infiltration media in 50 ml tube. The plant inserted into the 50 ml tube containing the constructs in infiltration media then will be put into vacuum dome for infiltration. Stop vacuum pump 1 minute after see bubbling in agro infiltration media. Remove infiltrated plants from infiltration media. 4.5 Plant care after infiltration and sample collection: Put infiltrated plants into well watered tray then move tray with plants in growth chamber for 4 days. New leaves will appear from stem and wire brush treated holes will be seen clearly. Cut the leaf tissue with small holes from the newly appearing leaf tissue for ELISA assay at day 4 after infiltration. (see picture below for infiltrated sugarcane plants 4 days after infiltration).

Example 9 Soybean In-Planta Transient Expression System

Prepare *Agrobacterium* containing a binary vector containing an expression cassette for s gene of interest. Cut off all the leaves except the tri-foliate leaf for infiltration. Remove one or two of the tri-foliate leaves, depending on the experiment. Gently damage the leaf by placing a piece of wood board on adaxial (top) side of the leaf and gently pressing against the abaxial (bottom) side of the leaf with a wire brush. To prepare soil-less plants, remove plants from small pots by cutting off the side roots using scissors, keeping main root undamaged. Rinse off the soil with water. Dip the pre-treated plants in approximately 30 ml of agro solution in a 50 ml tube or similar container. Place plants in a vacuum chamber and apply vacuum approximately for 3 minutes after bubbling appears. Gently release the vacuum and put the infiltrated plants into a 50 ml labeled tube with 30-40 ml water. Place all the infiltrated plants in a tray with clear plastic lid to maintain the humidity. 7.6.1 Infiltrated tissue can be harvested between 3 to 6 days after infiltration, but harvesting samples between day 4 to 5 results in best protein expression.

Example 10 Needle Matrix Method for Expressing Protein Compared to Existing Syringe Infiltration Method

TABLE 6

| Vector used for protein expression | |
|---|---|
| Vector ID | Expression cassette |
| 20791 | eNOS-01/prCMP-04/cMOV3Aa-08/tNOS-05-01 prSoUbi4-01/cCry1Ba-05/tSbUbi3-01 |
| 22238 | prUbi1-10/cMOV3Aa-06/iPEPC9-01/t35S-08 prSoUbi4-02/cCry1Ba-05/tSbUbi3-01 |
| 18515 | prCMP-01/cAmCyan-03/tNOS-05-01 |

Figure 3:
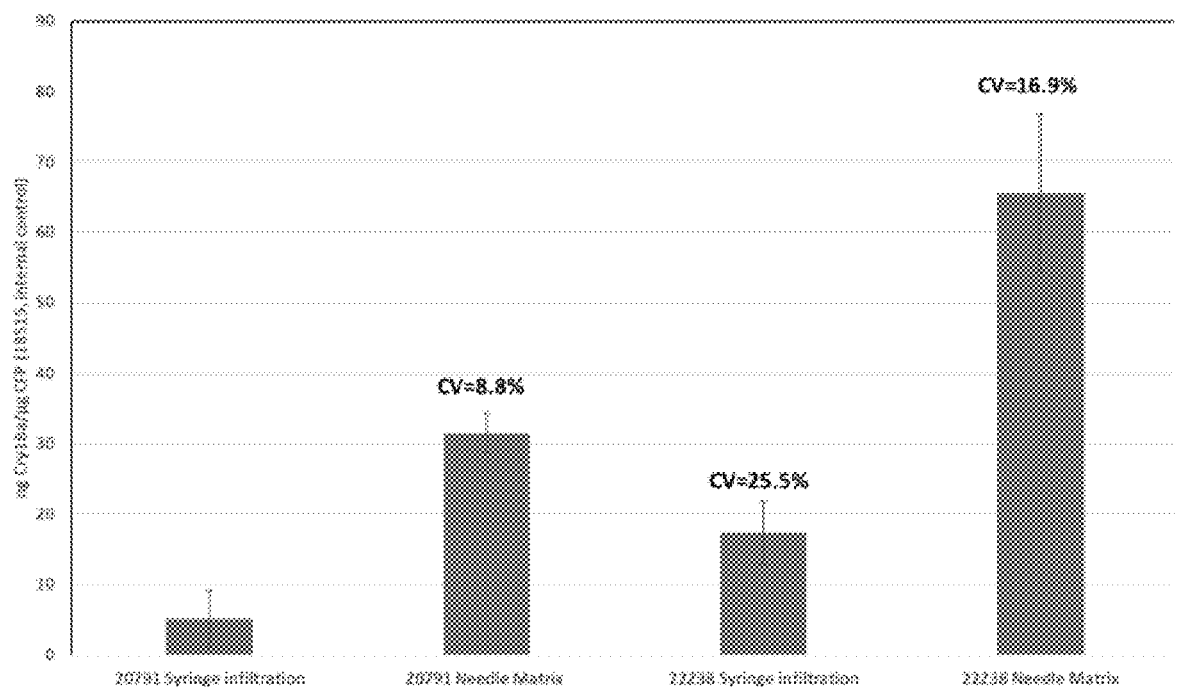
FIG. 3. shows that the needle matrix method greatly reduced assay coefficient of variation and increased detected protein expression level as compared to the syringe method described in U.S. Pat. No. 9,862,960. Two Cry1Ba vectors (20791 and 22238 were co-infiltrated with internal control vector 18515 at 1:1 ratio.

A) Preparation of Infiltration Media:
Vectors 20791, 22238 and 18515 were transformed into Agrobacteria strain LBA4404. Re-streaked the plate on a fresh YP plate with appropriate antibiotics for growth at 28° C. for 2 days. Re-suspend cells and mix with the internal control vector at 1:1 ratio.
B) Preparation of Plant Materials being Used
Maize plants were grown until 8 days after germination in a growth chamber around 25° C. with a photoperiod of 16 h light and 8 h dark.
C) Treatment of Pant for Needle Matrix Infiltration:
The top of maize plant from bottom leaf was cut off so that only the stem is remaining. The stem was wounded by pushing a needle matrix (use a wire brush as alternative option) against to a wood board; make sure the needles go through maize stem. Release the wire brush gently, avoiding severe damage to maize stem. A nascent leaf still inside the stem was also wounded.
Syringe infiltration does not need any pre-treatment for maize plant.
D) Needle Matrix Infiltration:
The plant was infiltrated by pipetting Agrobacteria from top of the stem by taking 0.6 mL of infiltration medium with 1 mL pipette and gently applying the agrobacteria from the top of stem. Infiltration media entered the stem and nascent leaf through the tiny holes created by wire brush damage. This will be enough for infiltration. Make sure to pipette up and down several times to mix when taking from infiltration medium. Two stems were infiltrated for one testing vector.
E) Syringe Infiltration
Maize leaves were infiltrated by delivering *Agrobacterium* media into leaf tissue using syringe without needle as described in US patent publication U.S. Pat. No. 9,862,960.
F) After Infiltration Care and ELISA Submission:
Infiltrated plants were placed in a growth chamber around 25° C. with a photoperiod of 16 h light and 8 h dark for 4 days. Tissue was harvested which showed clear wire and submitted for ELISA analysis.
G) Data Assay
Protein expression was normalized using internal control vector. Protein levels and coefficient of variation between samples is shown in FIG. 3. The needle matrix method produce more protein expression and had less variation between samples.

Example 11 Infecting Emerging Nascent Leaf

As described above. the plant was infiltrated by pipetting agrobacteria from the top of the stem by taking 0.6 mL of infiltration medium with 1 mL pipette and gently applying the agrobacteria from the top of stem. Infiltration media entered the stem and nascent leaf through the tiny holes created by wire brush damage. This will be enough for infiltration. Make sure to pipette up and down several times to mix when taking from infiltration medium. Two stems were infiltrated for one testing vector. Infiltrated plants were placed in a growth chamber around 25° C. with a photoperiod of 16 h light and 8 h dark for 4 days. Tissue was harvested which showed clear wire and submitted for ELISA analysis.

Figure 4:
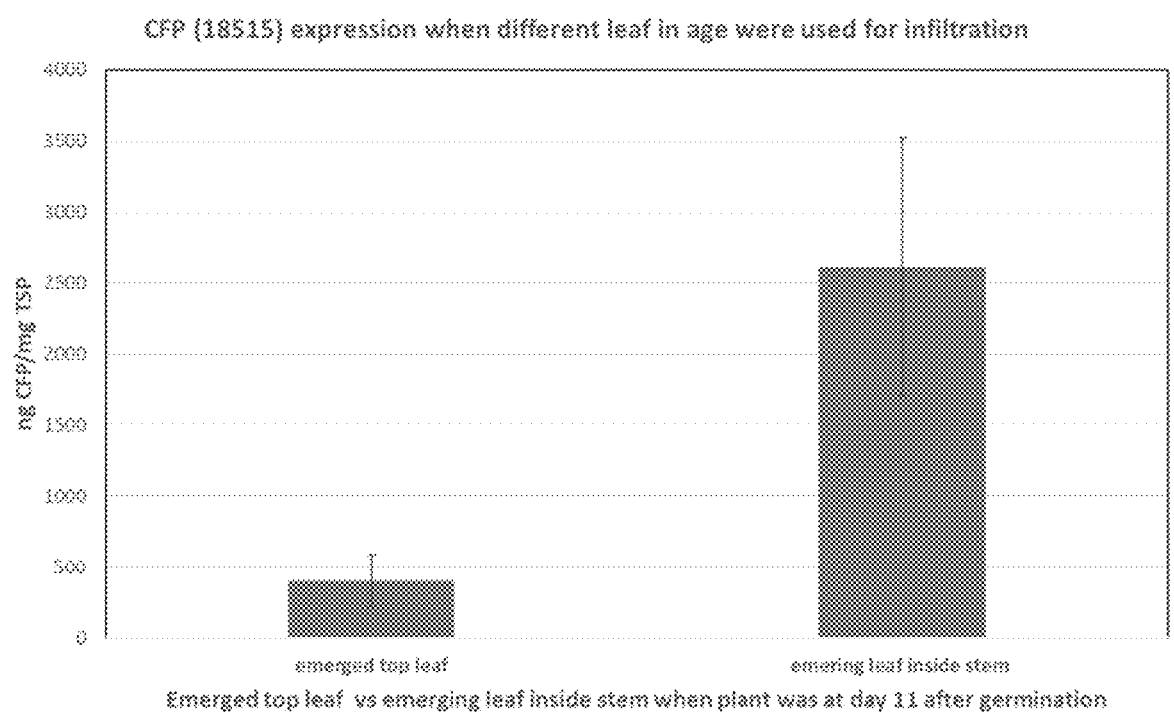
FIG. 4. Shows protein expression in an emerging leaf which was wounded and infiltrated with agrobacteria inside the stem compared to an emerged leaf which was wounded and infiltrated with agrobacteria after emergence from the stem.

The nascent leaf emerging from the stem was assayed for protein expression. Protein expression in the emerging leaf was compared to an emerged top leaf which was wounded and infiltrated with agrobacteria outside of the stem (see FIG. 4). This experiment shows the advantage of wounding and infiltrating a nascent leaf inside the stem.

What is claimed is:

1. A method of transiently expressing a nucleotide sequence in a plant part in planta comprising the steps of: a) wounding a plant part; b) *Agrobacterium*-infiltrating of an expression cassette comprising at least one nucleotide sequence operably linked to a promoter into the plant part in planta, and c) transiently expressing said at least one nucleotide sequence in the plant part, wherein *Agrobacterium*-infiltrating comprises cutting the plant stem above the second node and pipetting agrobacteria onto the cut site and, wherein the Agrobacteria enter the leafroll and infect a wounded nascent leaf.

2. The method of claim 1, wherein the plant is a monocot.

3. The method of claim 1, wherein the plant is a dicot.

4. The method of claim 1, wherein the plant is selected from the group of maize, sugarcane, and soybean.

5. The method of claim 1, wherein a plant comprising the plant part is 8-10 days old.

6. The method of claim 1, wherein the wounding a plant part is performed with a needle matrix.

7. The method of claim 1, wherein the needle matrix has 2 mm in distance spacing between each needle.

8. The method of claim 7, wherein the needle spacing produces assays with equal distances between wound sites in order to generate equal damage on leafroll to reduce assay variation.

9. The method of claim 6, wherein the needle matrix has 0.2 mm diameter needles.

10. The method of claim 1, wherein the increased transiently expressed protein level is 3 fold higher compared the method of syringe infiltration.

* * * * *